Figure 1A:
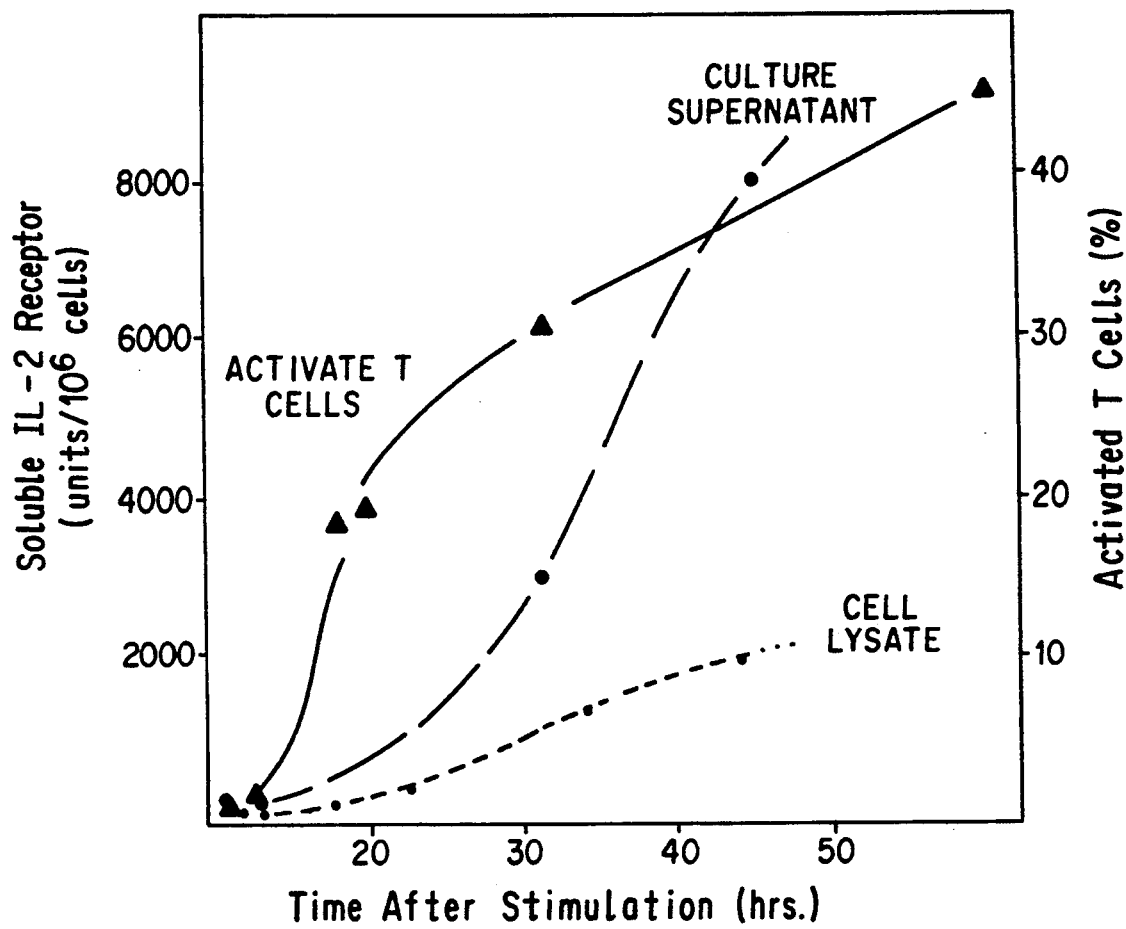

United States Patent [19]
Kung et al.

[11] Patent Number: 5,292,636
[45] Date of Patent: Mar. 8, 1994

[54] THERAPEUTIC AND DIAGNOSTIC METHODS USING SOLUBLE T CELL SURFACE MOLECULES

[75] Inventors: Patrick C. Kung, Lexington; Stephen H. Ip, Sudbury; Michael C. Brown, Wayland, all of Mass.; Linda A. MacKeen, Elkins Park, Pa.

[73] Assignee: T Cell Diagnostics, Inc., Cambridge, Mass.

[21] Appl. No.: 434,398

[22] Filed: Nov. 9, 1989

Related U.S. Application Data

[63] Continuation-in-part of Ser. No. 254,551, Oct. 6, 1988, abandoned, which is a continuation-in-part of Ser. No. 20,819, Mar. 2, 1987, Pat. No. 5,006,459, which is a continuation-in-part of Ser. No. 846,230, Mar. 19, 1986, abandoned.

[51] Int. Cl.$^5$ ............... G01N 33/543; G01N 33/564; G01N 33/574; G01N 33/577
[52] U.S. Cl. ...................... 435/5; 435/7.23; 435/7.24; 435/7.9; 435/7.94; 435/34; 435/974; 435/975; 436/506; 436/518; 436/536; 436/548; 436/811; 436/813
[58] Field of Search ............... 435/5, 7.23, 7.24, 7.94, 435/28, 975, 974, 34, 7.9; 436/506, 518, 548, 811, 813, 536; 935/110; 530/388, 75

[56] References Cited

U.S. PATENT DOCUMENTS

| | | | |
|---|---|---|---|
| 4,299,916 | 11/1981 | Litman et al. | 435/6 |
| 4,350,683 | 9/1982 | Galfre et al. | 424/85 |
| 4,376,110 | 3/1983 | David et al. | 436/513 |
| 4,391,904 | 7/1983 | Litman et al. | 435/7 |
| 4,472,500 | 9/1984 | Milstein et al. | 435/68 |
| 4,645,738 | 2/1987 | Knowles et al. | 435/7 |
| 4,707,443 | 11/1987 | Nelson et al. | 435/7 |
| 4,845,026 | 7/1989 | Kung et al. | 435/5 |

FOREIGN PATENT DOCUMENTS

| | | |
|---|---|---|
| 0162699 | 11/1985 | European Pat. Off. |
| 0202975 | 11/1986 | European Pat. Off. |
| 8705912 | 10/1987 | World Int. Prop. O. |
| 8801304 | 2/1988 | World Int. Prop. O. |

OTHER PUBLICATIONS

Berger et al., *Proc. Natl. Acad. Sci. USA*, 85, 2357–2361, 1988.
Sattentau et al., *Jour. Exp. Med.*, 170, 1319–1334, 1989.
Gay et al., Nature 328:626–629, (1987).
Dagleish et al., Immunol. Today 7:142–143, (1986).
Sattentau et al., Cell 52:631–633, (1988).
Fisher et al., Nature 331:76–78, (1988).
Germain et al., Cell 54:4411–444, (1988).
Weiss et al., Nature 331:15, (1988).
Siliciano et al., Cell 54:561–575, (1988).

(List continued on next page.)

*Primary Examiner*—David Saunders
*Attorney, Agent, or Firm*—Pennie & Edmonds

[57] ABSTRACT

The present invention is directed to the measurement of soluble T cell growth factor receptors, soluble T cell differentiation antigens, or related soluble molecules or fragments thereof, and the use of such measurements in the diagnosis, staging, and therapy of diseases and disorders. Specific embodiments involve the diagnosis and monitoring of therapy using absolute values of such soluble molecules. Further embodiments involve detecting a change in the levels of such soluble molecules, in the diagnosis and therapy of diseases and disorders. In specific embodiments, measurements of interleukin-2 receptor levels can be made to detect lung cancer, or to stage squamous cell lung carcinoma. In other embodiments, detection of increases in both soluble IL2R and creatinine in the body fluid of a transplant patient can be used to differentially diagnose renal allograft rejection from infection. The invention is also directed to methods for measurement of soluble CD4 antigens, which measurements can be used, in a specific embodiment, to diagnose a state of immune activation, to diagnose rheumatoid arthritis, to monitor therapeutic efficacy (e.g. of AIDS treatments), or to stage adult T cell leukemia in a patient. In another aspect, the invention relates to the detection, staging, and monitoring of therapy of diseases and disorders by measuring a plurality of soluble T cell markers.

37 Claims, 28 Drawing Sheets

OTHER PUBLICATIONS

Hussey et al., Nature 331:78–81, (1988).
Madden et al., Cell 42:93–104, (1985).
Littman et al., Nature 325:453–455, (1987).
Traunecker et al., Nature 331:84–86, (1987).
Smith et al., Science 328:1704–1707, (1987).
Deen et al., Nature 331:82–84, (1988).
Doyle et al., Nature 330: 256–259, (1987).
Booth et al., News & Comment, Science 239:341–343, (1988).
Meuer et al., Proc. Natl. Acad. Sci USA 79:4395–4399, (1982).
Kung et al., Monoclonal Antibodies in Clinical Investigations, Clinical Biochemistry-Contemporary Theories and Techniques, vol. 3, Academic Press pp. 89–115, (1984).
Biddison et al., J. Exp. Med. 159:783, (1984).
Hoxie et al., J. Immunol, 137:1194–1201, (1986).
Snow et al., J. Biol. Chem. 258:14675–14681, (1983).
Doumerc et al., 1986 6th Intl. Congress of Immunology, Toronto, Ontario, Canada, Jul. 1986, Abstr. 5.54.6., p. 768.
Kung et al., Clin. Chem. 34:1340 (1988).
Swain et al., Proc. Natl. Acad. Sci. U.S.A. 78:7101–7105 (1981).
Francus et al., J. Immunol. 140:1823–1829 (1988).
Greene et al., Ann. Intern. Med. 105:560–572 (1986).
Rubin et al., in Leukocytes and Host Defense, Oppenheim, J. J., and D. M. Jacobs, eds., Alan R. Liss, Inc., New York, pp. 95–102, (1986).
Yasuda et al., Blood 71:1021–1026 (1988).
Steis et al., Blood 71:1304–1309 (1988).
Pui et al., Blood 71:1135–1137 (1988).
Wolf et al., Arth. Rheum. 31:729–735 (1988).
Stolc et al., Diag. Clin. Immunol. 5:171–174 (1987).
Sethi et al., Immunol. Lett. 13:179–184 (1986).
Tomkinson et al., J. Immunol. 139:3802–3807 (1987).
Tomkinson et al., 1987, Released CD8 levels in immune activation, 2nd Annual Conference on Clinical Immunology, Washington, D.C.
Carpenter et al., Assessment of soluble CD8 and IL-2 receptor in the serum and synovial fluid from rheumatoid arthritis, 52nd Ann. Mtg., Am. Rheum. Assoc., Abstr., (1988).
Rubin et al., Chem. Abstr. vol. 104 No. 21, p. 489 abstract No. 184611, (May 26, 1986).
Rubin et al., (1985), Federation Proceedings, 69th Annual Mtg., Anaheim, California, vol. 44, No. 4, Apr. 21–26, 1985, Abstract 3131, pp. 946, Mar. 5, 1985.
Fujimoto et al., J. Exp. Med. 160:116–124, Jul. 1984.
Snow et al., The Journal of Biological Chemistry 260:2700–2708 (1985).
Snow et al., The Journal of Immunology 135:3172–3177, (1984).
Rubin et al., The Journal of Immunology 135:3172–3177, Nov. 1985.
Rubin et al., Clin Research, vol. 33, No. 2, p. 388A, (Apr. 1986).
Osawa et al., Eur. J. Immunol., 467–469, (1986).
Nelson et al., Journal of Clinical Immunology 6:114 120, (1986).
Mackeen et al., Fed. Proc., 45:457, Ab. No. 1746, (1986).
Nelson et al., Fed. Proc., vol. 45, No. 3, Abs. 1294, (Mar. 1, 1986).
Rubin et al., Clin. Res., 33, 457A, Apr. 1986.
Saadeh et al., Fed. Proc., vol. 45, No. 3, Abs. 1298 (1986).
De Moyos et al., FASEB Abstract Form Received at Society Office by Tuesday, Dec. 8, 1987.
Greaves et al., Int J. Immunopharmac. 3(3):283–300, (1981).
Rao et al., Cell Immunol. 80:310, (1983).
Baldwin et al., Monoclonal Antibodies for Cancer Detection and Therapy, p. 20, Karl Erik Hellstrom and Hellstron, (1985).
Kung et al., Science 206:347–349 (1979).
Reinherz et al, Proc. Natl. Acad. Sci. U.S.A. 76:4061–4065 (1979).
Reinherz et al., Proc. Natl. Acad. Sci. U.S.A. 77:1588–1592 (1980).
Verbi et al., Eur. J. Immunol. 12:81–86 (1982).
Kanellopoulos et al., The EMBO J. 2:1807–1814 (1983).
Kung et al., Int. J. of Dermatol. 22:67–74 (1983).
Krensky and Clayberger, Transplantation 39:339–348 (1985).
McDougal et al., Science 231:382–385 (1986).
Miller et al., Blood 58(1):78–86 (1981).
Falcao et al., J. Clin. Lab. Immunol. 13:141–143 (1984).
Oh et al., Scan. J. Immunol. 22:51–60 (1985).
Acuto et al., Cell 34:717–726 (1983).
Brenner et al., J. Exp. Med. 160:541–551 (1984).
Meuer et al., Proc. Natl. Acad. Sci. U.S.A. 81:1509–1513. (1984a).

(List continued on next page.)

OTHER PUBLICATIONS

Meuer et al., Ann. Rev. Immunol. 2:23–50 (1984b).
McKenzie and Parrish, J. Exp. Med. 144:847–851 (1976).
Parish et al., Immunogenetics 3:129–137 (1976).
Parish and McKenzie, Cellular Immunol. 33:134–144 (1977).
Parish et al, Infection and Immunity 26:422–426 (1979).
Wilson et al., J. Immunol. 122:1967–1971 (1979).
Sandrin et al., J.N.C.I. 66:279–283 (1981).
Mier and Gallo, Proc. Natl. Acad. Sci. U.S.A. 77:6134–6138 (1980).
Smith, Immunol. Rev. 51:337–357 (1980).
Arya et al., Science 223:1086–1087 (1984).
Lotze et al., J. Immunol. 135:2865–2875 (1985).
Touw et al., Blood 66:556–561 (1985).
Robb et al., J. Exp. Med. 154:1455–1474 (1981).
Uchiyama et al., J. Immunol. 126:1393–1397 (1981).
Leonard et al., Nature 300:267–269 (1982).
Korsmeyer et al., Proc. Natl. Acad. Sci. U.S.A. 80:4522–4526 (1983).
Depper et al., J. Immunol. 133:1691–1695 (1984).
Sugamura et al., Proc. Natl. Acad. Sci. U.S.A. 81:7441–7445 (1984).
Tsudo et al., J. Exp. Med. 160:612–617 (1984).
Waldmann et al., J. Exp. Med. 160:1450–1466 (1984).
Dower et al., J. Exp. Med. 162:501–515 (1985).
Ebert et al., Clin Immunol. and Immunopathol. 37:283–297 (1985).
Rubin et al., Hybridoma 4:91–102 (1985).
Uchiyama et al., J. Clin. Invest. 76:446–453 (1985).
Greene and Leonard, Ann. Rev. Immunol. 4:69–95 (1986).
Gupta, Clin. Immunol. and Immunopathol. 38:93–100 (1986).
Mutsuoka et al., Leukemia Res. 10:597–603 (1986).
Tsudo et al., Blood 67:316–321 (1986).
Tuow et al., Blood 68:1088–1094 (1986).
Chilosi, et al., Int. J. Biological Markers 2:101–104 (1986).
Durno et al., Blood 68 Suppl. #1,124a (1986).
John et al., Sixth Int. Cong. Immunol. Toronto, Canada (1986).
Keller et al., Am. Diabetes Assoc. (1986).
Nelson et al., Pediatric Res. 20:136–139 (1986).
Pizzolo et al., Blood 68 Suppl. #1, 228a (1986).
Reuben et al., Blood 68 Suppl. #1, 213a (1986).
Rubin et al., J. Immunol. 137:3841–3844 (1986).
Treiger et al., J. Immunol. 136:4099–4105 (1986).
van Es et al., Transplantation 37:65–69 (1984).
Austen and Cosimi, N. Engl. J. Med. 311:1436–1438 (1984).
Hancock et al., Transplantation 39:430–438 (1985).
Magrath et al., Blood 63:1102–1111 (1984).
Pui et al., Blood 66:778–782 (1985).
Murphy et al., J. Clin. Oncol. 4:1732–1739 (1986).
Arseneau et al., Am. J. Med. 58:314–321.
Nelson et al., Fed. Proc., vol. 145, No. 3, Abstract 1746, Mar. 1, 1986.

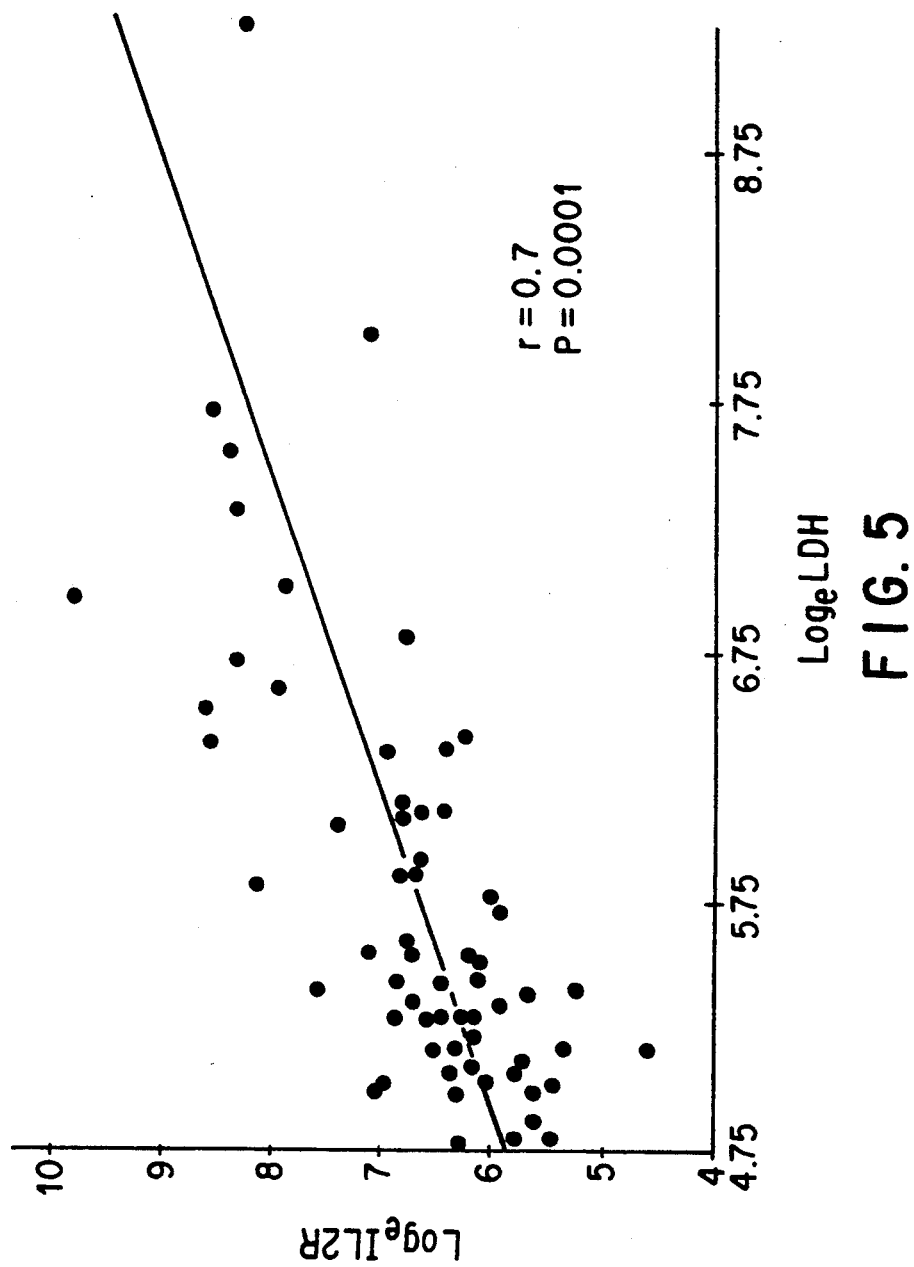

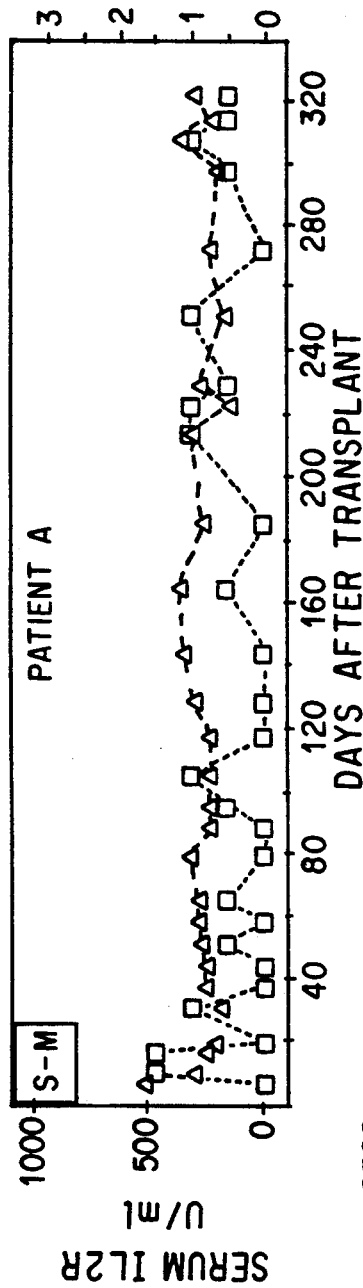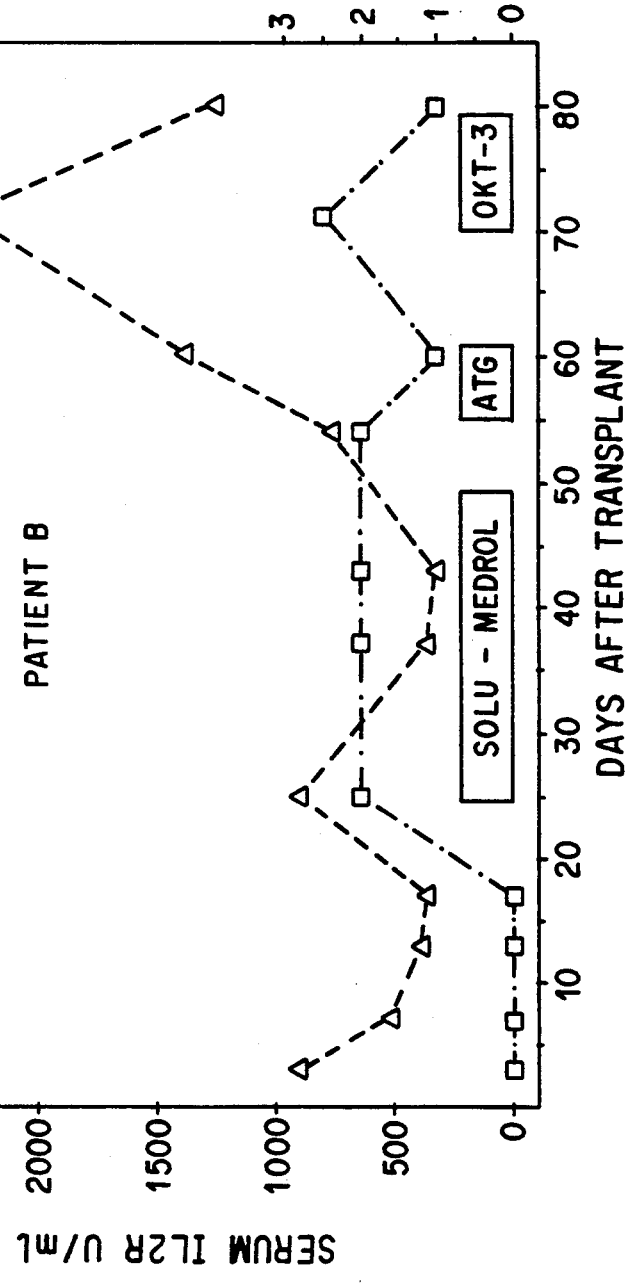

THERAPEUTIC AND DIAGNOSTIC METHODS USING SOLUBLE T CELL SURFACE MOLECULES

The present application is a continuation-in-part of application Ser. No. 264,551 filed Oct. 6, 1988, now abandoned which is a continuation-in-part of application Ser. No. 020,819 filed Mar. 2, 1987, now U.S. Pat. No. 5,006,459, issued May 9, 1991 which is a continuation-in-part of Ser. No. 846,230 filed Mar. 31, 1986, now abandoned, each of which is incorporated by reference herein in its entirety.

TABLE OF CONTENTS

1. Introduction
2. Background of the Invention
   2.1. T Cell Growth Factors and Receptors
   2.2. T Cell Surface Molecules
   2.3. Soluble Immune Cell Surface Molecules
   2.4. Hairy Cell Leukemia
3. Summary of the Invention
   3.1. Definitions
4. Description of the Figures
5. Detailed Description of the Invention
   5.1. Monitoring the Effect of a Therapeutic Treatment
   5.2. Detecting and/or Staging a Disease in a Subject
   5.3. Differential Diagnosis of a Physiological Condition
   5.4. Soluble T Cell Growth Factor Receptors, T Cell Differentiation Antigens, and Related Molecules
      5.4.1. Kits and Assays for Measurement
      5.4.2. Formulation of an Immunoassay for the Preferential Detection of Soluble Forms of T Cell Surface Markers over Solubilized Forms
      5.4.3. Soluble CD4 and Assay for its Detection
      5.4.4. Detecting or Staging of Disease or Monitoring of Response to Treatment in Patients by Measurement of a Plurality of Soluble T Cell Surface Markers
6. Soluble IL2R Detection in Patients
   6.1. Monoclonal Antibodies
   6.2. Soluble IL2R Assay
      6.2.1. Procedure
      6.2.2. IL2R Control Standards
      6.2.3. Flow Cytometric Methods
7. There is No Correlation Between Soluble IL2R Level and IL2R Bearing Lymphocytes In Vivo
8. Serum Measurement of Soluble IL2R May be Used for Staging Leukemia or Monitoring a Therapeutic Treatment
9. High Serum IL2R Levels are Related to Advanced Disease and a Poor Outcome in Childhood Non-Hodgkin's Lymphoma
   9.1. Patients and Methods
      9.1.1. Patients
      9.1.2. Treatment
      9.1.3. Determination of Soluble IL2R Levels
      9.1.4. Determination of Serum Lactic Dehydrogenase
      9.1.5. Statistical Analysis
   9.2. Results
      9.2.1. Soluble IL2R Levels Show a Clear Relationship to Disease Stage
      9.2.2. Soluble IL2R Levels Show a Linear Relationship with Serum LDH Levels
      9.2.3. Higher Soluble IL2R Levels are Associated with a Poorer Treatment Outcome
10. Serum CD8 Antigen and Interleukin-2 Receptor Levels in Childhood Hodgkins's Disease
11. Elevated Soluble IL2R Level in Serum of Cancer Patients Under Therapeutic Treatment with IL-2
    11.1. Serum IL2R Levels in Cancer Patients Treated with IL-2
    11.1. Elevated Serum IL2R Levels in Cancer Patients Responding to IL-2 Therapy
12. Serum Level of Soluble IL2R May be Used to Differentially Diagnose Between Transplant Rejection and Therapeutic Toxicity and to Monitor Therapeutic Toxicity
13. Plasma IL2R Levels in Renal Allograft Recipients
    13.1. Patients and Methods
    13.2. Plasma Contains Elevated Levels of Soluble IL2R During Episodes of Renal Allograft Rejection
14. A Comparison of Serum IL2R Levels and Endomyocardial Biopsy Grades in the Monitoring of Cardiac Allography Rejection
    14.1. Methods
    14.2. Normal IL2R Levels Indicate the Absence of Cardiac Allograft Rejection Whereas Elevated IL2R Levels Strongly Indicate Rejection
15. Serum Measurement of Soluble IL2R May be Used for Staging Viral Infections
16. CELLFREE ® Enzyme Immunoassay for the Detection of Soluble, Released IL2R
    16.1. Principles of the Method
    16.2. CELLFREE ® Test Kit Components and Suggestions
       16.2.1. Reagents Supplied
       16.2.2. Materials Required But Not Provided
       16.2.3. Reagents Precautions
       16.2.4. Specimen Collection and Handling
       16.2.5. Reagent Preparation
       16.2.6. Suggested Plate Coating Protocol
       16.2.7. Suggested Assay Protocol
       16.2.8. Construction of a Standard Curve
       16.2.9. Patient Samples
       16.2.10. Limitations
    16.3. CELLFREE ® Reagents
       16.3.1. Monoclonal Antibodies
       16.3.2. Standards
       16.3.3. Patient Sera
       16.3.4. Purified IL2R
       16.3.5. Interleukin-2
    16.4. CELLFREE ® IL2R Assay
       16.4.1. Standardization
       16.4.2. Precision
       16.4.3. Accuracy
       16.4.4. Specificity of Assay and Effects of Interleukin-2
       16.4.5. IL2R Levels in Human Sera
17. Soluble IL2R Measurement as an Indication of the Extent of Bone Marrow Leukemic Infiltration in Hairy Cell Leukemia Patients
    17.1. Procedures and Definitions
       17.1.1. Assay for Soluble IL2R
          17.1.1.1. Specimen Collection and Handling
          17.1.1.2. Assay Procedure
          17.1.1.3. Calculation of Assay Results
       17.1.2. Description of Bone Marrow Cytopathology/Histopathology Procedures
          17.1.2.1. Bone Marrow Sampling Procedures
          17.1.2.2. Preparation of Specimens for Microscopic Evaluation 17.1.2.3. Light Microscopic Evaluation of Bone Marrow Specimens
17.1.2.4. Sensitivity and Specificity of the Procedure
17.1.2.5. Criteria for Response to Treatment with Alpha-Interferon
17.1.2.6. Definitions of Treatment Phase
17.2. Clinical Trial Design
17.3. Results
  17.3.1. Correlations Between Serum IL2R and Leukemic Indices
  17.3.2. Serum IL2R Expression: Hairy Cell Leukemia and Blood Donor Sera
  17.3.3. Association Between Serum IL2R and Bone Marrow Biopsy Leukemic Index
  17.3.4. Association Between Serum IL2R and Major Clinical Response Outcomes
17.4. Conclusions
18. Soluble IL-1 Binding Protein Detection in Patient Serum
  18.1. Monoclonal Antibodies
  18.2. Soluble IL-1 Binding Protein Assay
  18.3. Results
19. Soluble CD8 Detection in Patients
  19.1. Monoclonal Antibodies
  19.2. Soluble CD8 Assay
  19.3. CD8 Control Standards
  19.4. Enzyme Immunoassay for the Quantitation of Cell-Free Human T Cell CD8-Like Molecule
    19.4.1. Evaluation of Anti-CD8 Monoclonal Antibodies as a Capture Antibody
20. Serum CD8 Levels in Evaluation of Disease and Disorders
  20.1. Differential Diagnosis of Rheumatoid Arthritis
  20.2. Serum CD8 Levels in a Renal Allograft Recipient
  20.3. Serum CD8 Levels in Children with Non-Hodkin's Lymphoma
  20.4. CD8 Levels in Infectious Disease
  20.5. Soluble CD8 Levels as a Measure of the Immune Response to Disease
21. Molecular Characterization of the Soluble CD8 Antigen
  21.1. Methods
  21.2. Anti-CD8 mAbs Recognize a Soluble CD8 Antigen of 52-55 Kilodaltons
22. Soluble CD2 Detection
23. Soluble CD4 Antigen
  23.1.1 Materials and Methods
    23.1.1.1. Antibodies
    23.1.2. Immunoassay Protocol
      23.1.2.1. Initial Assay
      23.1.2.2. Optimized Assay
    23.1.3. Cell Procedures
  23.2. Results
    23.2.1. Using Initial Assay Protocol
    23.2.2. Results Using Optimized Assay Protocol
  23.3. Discussion
24. Elevated Concentrations Of Soluble Interleukin-2 Receptors In Serum Of Smokers And Lung Cancer Patients
  24.1. Materials and Methods
    24.1.1. Patients
    24.1.2. Controls
    24.1.3. Serum Samples
    24.1.4. Soluble IL2R Assay
    24.1.5. Statistical Analysis
  24.2. Results
    24.2.1. Concentrations of Soluble IL2R in Normal Non-Smokers and Smokers
    24.2.2. Concentrations of Soluble IL2R in Lung Cancer
    24.2.3. Concentrations of Soluble IL2R in Serum of Patients with Squamous Cell Lung Carcinoma
    24.2.4. Concentrations of Soluble IL2R in Patients with Lung Adenocarcinoma
  24.3. Discussion
25. A critical Analysis of the Diagnostic Utilities of Immunoassays for Serum and Urine Interleukin-2 Receptor Levels in Renal Allograft Recipients
  25.1. Materials and Methods
    25.1.1. Patients
    25.1.2. IL2R Assay
    25.1.3. Data Analysis
  25.2. Results
  25.3. Discussion
26. Evaluation of the Role of Soluble CD8 Receptor and IL-2 Receptor in Patients With Human Immunodeficiency Virus Infections
  26.1. Methods
    26.1.1. Sample Selection
    26.1.2. HIV p24 Antigen Assay
    26.1.3. CD4/CD8 Ratio
  26.2. Results
27. Deposit of Hybridomas

1. INTRODUCTION

The present invention is directed to the measurement of soluble T cell surface molecules, such as soluble T cell growth factor receptors and T cell differentiation antigens or fragments thereof, and the application of such measurements in the diagnosis and therapy of diseases and disorders. The measurement of such molecules, and preferably a plurality of such molecules, can be used in monitoring the effect of a therapeutic treatment, detecting and/or staging disease or in differential diagnosis of a physiological condition.

2. BACKGROUND OF THE INVENTION

2.1. T Cell Growth Factors and Receptors

T cells secrete a variety of polypeptides affecting immunoregulation of hematopoietic cells and are themselves subject to regulation by hormone peptides interacting with specific receptors on their cell surface. Interleukin 2 (IL-2), originally termed T cell growth factor, is synthesized and secreted by antigen- or lectin-activated T lymphocytes in the presence of macrophage-derived interleukin-1 and must interact with specific high-affinity membrane receptors to exert its biological effects (Smith, K. A., 1980, Immunol. Rev., 51:337-357; Leonard, W. J., et al., 1983, Proc. Natl. Acad. Sci. U.S.A. 80:6957-6961). The interleukin 2 receptor (IL2R, Tac antigen) is not present on the surface of resting T or B lymphocytes. Upon activation by specific antigens or mitogens, T cell proliferation is mediated by an autocrine mechanism whereby activated cells secrete IL-2 and also express cell surface receptors for IL-2 (IL2R) (Leonard, W. J., et al., 1982, Nature, 300:267; Meuer, S. C., et al., 1984, Proc. Natl. Acad. Sci. U.S.A. 81:1509). In addition to T cells, B cells (Mingari, M. C., et al., 1984, Nature 312:641-3; Pike, B. L., et al., 1984, Proc. Natl. Acad. Sci. U.S.A. 81:7917-21; Saiki, O., et al., 1988, J. Immunol. 140:853-8), NK cells (Ortaldo, J. R., et al., 1984, J. Immunol. 133:779-83; Kehrl, J. H., et al., 1988, J. Clin.. Invest, 81:200-5) and possibly monocytes (Herrmann, F., et al., 1985, *J. Immunol.* 162:1111-6; Holter, W., et al., 1986, *J. Immunol.* 136:2171-75) express a membrane-bound IL2R.

Current evidence suggests that both chains of the IL-2 heterodimer receptor expressed on the surface of activated T cells, are encoded by a single gene on human chromosome 10 (Leonard, W. J., et al., 1984, *Nature* 311:626:31). The high affinity IL2R that functions to signal T cell cycle progression is composed of two distinct polypeptide chains, each of which contains an IL-2 binding site (Teshigawara, K., et al., 1987, *J. Exp. Med.* 165:223). The larger IL-2 binding protein (75 kD molecular weight) is designated as the beta chain, whereas the smaller protein (55 kD molecular weight) is termed the alpha chain (Smith, K. A., 1988, *Adv. Immunol.* 42:165-78). The alpha chain was the first IL-2 binding protein to become recognized as an "activation antigen" on the surface of activated T cells (hence the name anti-Tac for "T activated") (Uchiyama, T., et al., 1981, *J. Immunol.* 126:1393-7).

Interaction of IL-2 with its cell surface receptor results in a continuous T cell proliferation (Greene, W. C. and Leonard, W. J., 1986, *Ann. Rev. Immunol.* 4:69-95; Smith, K. A., 1984, *Ann. Rev. Immunol.* 2:319-333). Measurement of IL2R provides information on the state of immune activation of the lymphoid population. This has been accomplished by measuring IL2R on cell surfaces using flow cytometry or fluorescence microscopy. Using monoclonal antibodies which define the IL-2 receptor, altered IL-2 receptor expression has been reported in a number of immune abnormalities (Greene and Leonard, supra; Depper, J. M., et al., 1984, *J. Immunol.* 133:1691-1695). Membrane IL2R has been found on certain B- or T-cell malignancies including Burkitt's lymphoma (Waldmann, T. A., et al., 1984, *J. Exp. Med.* 160:1450-1466), hairy cell leukemia (Waldmann et al., supra; Korsmeyer, S. J., et al., 1983, *Proc. Natl. Acad. Sci. U.S.A.* 80:4522-4526), and human T cell leukemia virus (HTLV)-I-associated adult T cell leukemia (Depper, J. M., et al., 1984, *J. Immunol.* 133:1691-1695). The function of cellular IL2R in lymphoid malignancies has not been fully elucidated. Several cases of common, pre-B or T cell acute lymphoblastic leukemia (ALL) have been induced to express IL2R after in vitro activation (Touw, I., et al., 1985, *Blood* 66:556-561; Touw, I., et al., 1986, *Blood* 68:1088-1094; Matsuoka, M., et al., 1986, *Leuk. Res.* 10:597-603) and, in some cases, interleukin 2 stimulated subsequent colony formation of neoplastic progenitor cells in vitro (Touw, 1985, supra; Touw, 1986, supra).

Leukemia cells from some patients with T cell chronic lymphocytic leukemia were shown to have the receptors and a good proliferative response to exogenous interleukin 2 (Uchiyama, T., et al., 1985, *J. Clin. Invest.* 76:446-453; Tsudo, M., 1986, *Blood* 67:316-321). However, HTLV-1 associated adult T cell leukemia constitutively expressed high levels of cell surface IL2R but had no or very poor proliferative responses to interleukin 2 (Uchiyama, 1985, supra; Arya, S. K., et al., 1984, *Science,* 223:1086-1087). Ebert et al. (1985, Clin. Immunol. Immunopathol. 37:283-297) have reported that T cells from patients with AIDS virus lack the ability to express IL2R on their surface even when the cell is activated.

Utilizing immunohistochemical staining, Kurnick reported high numbers of IL2R and HLA-DR positive cells in lung tumor infiltrating lymphocytes (Kurnick, J. T., et al., 1986, *Clin. Immunol. Immunopath.* 38:367-380).

2.2. T Cell Surface Molecules

Clusters of differentiation (CD) have been established which define human leukocyte differentiation antigens (Bernard and Boumsell, 1984, *Hum. Immunol.* 11:1-10), by the comparison of reactivities of monoclonal antibodies directed against the differentiation antigens. The T cell surface antigens, their classification into epitope-defined subgroups, and their distributions on T cells have been studied by use of monoclonal antibodies directed against human T cells (Clark et al., 1983, *Immunogenetics* 18:599-615; Hansen et al., 1984, in *Leucocyte Typing,* Bernard, A., et al., eds., Springer-Verlag, New York, pp. 195-212). Some of the T cell clusters of differentiation and other T cell surface molecules are listed in Table I.

TABLE I

| | T CELL SURFACE MARKERS | | | |
|---|---|---|---|---|
| T Cell Surface Marker | Molecular Weight (kd) | Expression | Detection Monoclonal Antibody | Reference |
| T Cell Antigen Receptor | 90 | All T Cells | T40/25 | Brenner, M. B., et al., 1984, J. Exp. Med. 160: 541-551 |
| CD8 | 30/43 | Suppressor/ cytotoxic (subset of T cells) | OKT8 Leu 2 | Reinherz, E. L., et al., 1979, PNAS USA 76:4061-4065; Ledbetter, J. A., et al., 1981 Monoclonal Antibodies and T Cell Hybridoma Elsevier/ North Holland, N.Y., pp. 16-22. |
| T6 | 49 | Thymocytes & Langerhans Cells Leukemia Cells | OKT6 NAI/34 | Reinherz, 1979, supra. |
| CD4 | 62 | Helper/Inducer Cells (subset of T cells) | OK4 Leu 3a | Kung, P. C., et al., 1979, Science 206: 347-349 |
| CD3 | 19 | Pan T Cell | OKT3 | Kung, id. |
| TAC | 50 | IL-2 Receptor (Activated T | Anti-TAC | Uchiyawa, T., et al., 1981, J. |

TABLE I-continued

T CELL SURFACE MARKERS

| T Cell Surface Marker | Molecular Weight (kd) | Expression | Detection Monoclonal Antibody | Reference |
|---|---|---|---|---|
| | | Cells) | | Immunol. 126(4):1393-1397 |
| T9 | 94 | Transferrin Receptor (Activated T Cells) | OKT9 | Reinherz, E. L., et al., 1980, PNAS USA 77:1588-1592 |
| CD2 | 50 | All T Cells | OKT11 Leu 5 | Verbi, W., et al., 1982, Eur. J. Immunol. 12:81-86 |
| VLA-1 | 130/165/210 | Late Activated T Cells | VLA-1 | Helmer, M. E., et al., 1984, J. Immunol. 132:3011-3018 |

These T cell surface markers serve as markers of the cell lineage, the identity of the functional T cell subset to which the T cell belongs, and the activation state of the T cell. Several of the cell surface molecules have been studied in great detail and have been found to be important in initiating and regulating immune functions, and are critical to communication processes between immune cells. T cell antigen receptor, a surface molecule which comprises a disulfide-linker dimer of approximately 90 kilodaltons (kd), recognizes specific antigens and is responsible for initiating a complex series of biochemical events which constitute the T cell activation process (Meuer, S. C., et al., 1984, *Ann. Rev. Immunol.* 2:23-50; Acuto, O., et al., 1983, *Cell* 34:717-726). The CD3 structure is a three-chain complex associated with the T cell receptor (Kannellopoulos, J. M., et al., 1983, *EMBO J.* 2:1807; Borst, J., et al., 1983, *Eur. J. Immunol,* 13:576; Van Den Elsen, P, et al., 1984, *Nature* 312:413; Meuer, S. C., et al., 1983, *J. Exp. Med.* 157:705). Lymphokine receptors, e.g. interleukin 2 (IL-2) receptor and interleukin 1 (IL-1) receptor, are essential for the activation and proliferation of T cells (Smith, K. A., 1984, *Ann. Rev. Immunol.* 2:319-333; Dower, S. K., et al., 1985, *J. Exp. Med.* 162:501-515). CD8 is a T cell specific surface glycoprotein expressed on the surface of approximately 30% of T lymphocytes associated with suppression and cytotoxic functions and the ability to recognize antigen in the context of class I MHC antigens (Swain, S. L., 1983, *Immunol. Rev.* 74:129-42) CD4 (OKT4 antigen) is a 55 kd glycoprotein expressed on the surface of approximately 60% of all T lymphocytes and is associated with helper function (Reinherz et al., 1979, *Proc. Natl. Acad. Sci. U.S.A.* 76:4061-4065) and the ability to recognize antigens in the context of type II MHC antigens (Swain, supra; Meuer, S. C., et al., 1982, *Proc. Natl. Acad. Sci. U.S.A.* 79:4395-99). CD4 has also been identified as the receptor for the HTLV-III virus associated with acquired immune deficiency syndrome (AIDS) (McDougal, J. S., et al., 1986, *Science* 231:382-385). These various cell surface markers have enormous clinical application potentials for the identification of lymphocyte populations and their functional status (Krensky, A. M. and Clayberger, C., 1985, *Transplant.* 39(4):339-348; Kung, P. C., et al., 1984, Monoclonal Antibodies in Clinical Investigations, Clinical Biochemistry-Contemporary Theories and Techniques, vol. 3, Academic press, pp. 89-115; Kung, P. C., et al., 1983, *Int. J. Dermatol.* 22(2):67-73).

Existing clinical methods of T cell typing involve the use of monoclonal antibodies which define T cell surface markers to detect the presence of specific cell surface markers on the T cell surface. Measuring the total numbers of T cells by surface markers has been useful for the characterization and classification of lymphoid malignancies (Greaves, M., et al., 1981, *Int. J. Immunopharmac.* 3(3):283-300). Changes in the relative percentage of T helper and T suppressor/cytotoxic cells were found to be associated with immune events in renal transplantation due to viral infection (Colvin, R. B, et al., 1981, Proc. 8th Int. Congr. Nephrol., Athens, pp. 990-996), autoimmune E. M., et al., 1981, *Int. J. Immunopharmac.* (3):313-319), and AIDS (Gupta, S., 1986, *Clin. Immunol. Immunopathol.* 38:93-100; Ebert, E. C., et al., 1985, *Clin. Immunol. Immunopathol.* 37:283-297).

The expression of T cell surface markers has also been used for the assessment of the immune status of patients. It has been established that by measuring the relative number of distinct, functional T cell subsets, and/or the relative number of activated T cells in peripheral blood or tissues, an assessment of the immunological condition of a patient is possible. The activation antigens (e.g. IL-2 receptor) appear to be involved in T cell growth and differentiation processes.

Antibodies to CD4 have been widely described (Kung, P. C., et al., 1979, *Science* 206:347-349) and are commercially available. A series of such antibodies reacting with non-competing epitopes on the CD4 molecule have been described. Such a set has been termed OKT4, OKT4A, OKT4B, OKT4C, OKT4D, OKT4E, and OKT4F (Rao, P. E., et al., 1983, *Cell. Immunol.* 80:310).

Antibodies directed against the CD4 or CD8 antigens have been shown to block cell function. Antibodies against CD4 block most helper T functions, mixed lymphocyte reactions and induction of T helper activity (Biddison, W. E., et al., 1984, *J. Exp. Med.* 159:783). Antibodies against CD8 block the cytotoxic activity of CD8 positive cytotoxic T lymphocytes (Swain, S L., 1981, Proc. Natl. Acad. Sci. U.S.A. 78:7101-7105). Antibodies against CD4 have also been described that are capable of activating CD4-positive T cells. CD4 is internalized upon treatment of the cells with phorbol esters and resulting phosphorylation (Hoxie, J. A., et al., 1986, *J. Immunol.* 137:1194-1201).

The cloning of the gene encoding CD4 reveals that it, like CD8, is a member of the immunoglobulin supergene family, containing both amino acid (32%) and structural ($\beta$ sheets held together by disulfide bridges) homology at the V (variable)-like domain of CD4 to the V region of immunoglobulin (Maddon, P. J., et al., 1985, Cell 42:93-104). This V-like region of the molecule is followed by a stretch of 263 amino acids with no known homology to other molecules, followed by a transmembrane domain and highly charged cytoplasmic tail, containing serines which are phosphorylated upon activation (Littman, D. R., et al., 1984, *Nature* 325:453-55)

Homology between CD4 and CD8 is quite low. CD8 exists on the cell surface as dimeric or multimeric structures composed of a 33 kD monomer (Snow, P. M., et al., 1983, *J. Biol. Chem.* 258:14675-14681).

2.3. Soluble Immune Cell Surface Molecules

Several immune cell surface markers have been detected in the serum. The molecules of the human major histocompatibility complex (HLA molecules) are sets of cell surface glycoproteins involved in immune recognition. These macromolecular antigens have also been found to be present in body fluids such as serum (Pellegrino, M. A., et al., 1984, *Meth. Enzymol.* 108:614-624). The serum levels of Class I HLA-A and HLA-B have been shown to be present in sufficient quantity to perform HLA-typing in sera (Russo, C., et al., 1983, Transplant. Proc. 15(1):66-68; Pellegrino, M. A., et al., 1981, Transplant. Proc. 13(4):1935-1938). The presence of Class II HLA-DR in serum has also been detected (Sandrin, M. S., et al., 1981, *J. Natl. Cancer Inst.* 66(2):279-283; Russo, C., et al., 1983, *Transplant. Proc.* 15(1):57-59). The serum HLA-DR (Ia) has been shown to be markedly depressed in tumor patients.

A soluble form of IL2R has been detected (Rubin et al., 1985, *J. Immunol.* 135:3172-3177; Rubin et al., 1985, Fed. Proc. 44:946; U.S. Pat. No. 4,707,443 by Nelson et al.) that is released by activated normal peripheral blood mononuclear cells and synthesized in large amounts in vitro by HTLV-I-infected leukemic cell lines. A sandwich enzyme immunoassay was used to quantitate the soluble IL2R.

Little is known about the functional significance of soluble IL2R. Since soluble IL2R is capable of binding interleukin 2 (Rubin, L. A., et al., 1985, *J. Immunol.* 35:3172-3177), it may have an immunoregulatory role by competing with cellular IL2R for the ligand and thus down-regulating the immune response. In this regard, the soluble IL2R has been suggested to be a "blocking factor" produced by the malignant cells to inhibit the host's immune response to the tumor (id.).

Subsequent studies have disclosed comparable levels of soluble IL2R in cord blood and peripheral blood from normal adults (Nelson, D. L., et al., 1986, *Pediatr. Res.* 20:136-39). Increased serum levels of IL2R have been found in patients with certain B or T cell malignancies (Nelson, D. C., 1986, *Fed. Proc.* 45:377; Saadeh, C., et al., 1986, *Fed. Proc.* 45:378; MacKeen, L., et al., 1986, *Fed. Proc.* 45:454; Reuben, J. M., et al., 1986, *Blood* 68(5), Supp. 1:213a). Elevated levels of soluble IL2R have also been reported present in the serum of aged subjects (Saadeh, C., et al., 1986, *Fed. Proc.* 45:378), and in patients with AIDS (Saadeh, supra).

Several other cell surface markers which are primarily present on T cells have also been found in soluble form. CD2, a T cell surface molecule present in all normal T cells and a receptor for sheep red blood cells, has been detected at higher levels in the sera of certain cancer patients than those found in normal control patients (Falcao, R. P., et al., 1984, *Clin. Lab. Immunol.* 13:141-143; Oh. S.-K., et al., 1985, Scand. J. Immunol. 22:51-60). CD8 (Leu 2, OKT8), a surface marker found on the surface of suppressor/cytotoxic T cells and which may be involved in cellular recognition, has also been reported at highly elevated levels in the serum of patients with T cell leukemia (Fujimoto, J., et al., 1983, *J. Exp. Med.* 159:752-766). Leu-1, another T cell surface molecule, was measured in serum following anti-Leu-1 monoclonal antibody treatment (Miller, R. A., et al., 1982, *New Engl. J. Med.* 306:517-520). Oh et al. (1985, supra) reported that less than half of the patients with malignancies in their study presented elevated levels of soluble OKT11 receptor in their serum.

However, not all T cell surface molecules are released into the serum (Fujimoto, J., et al., 1983, *J. Exp. Med.* 159:752-766). Leu 1 antigen was not detectable in the serum of normal or leukemic patients who have not received antibody therapy. Leu 3 antigens were also not detectable in soluble form in T cell culture supernatants (id.).

Fujimoto et al. (1983, *J. Exp. Med.* 159:752-766) were unable to find evidence of released CD4 using a sandwich enzyme immunoassay based on Leu3b and Leu3a (Becton-Dickinson). This assay worked well with detergent lysates of cells but did not detect released CD4 in culture supernatants of CD4+ and CD8+ leukemic T cells which could be shown to release CD8, or in culture supernatants of CD4+ T cells.

Additionally, coassigned, pending U.S. patent application Ser. No. 804,289, filed Dec. 3, 1985 and now U.S. Pat. No. 4,845,026, entitled "Assay Systems for Detecting Cell Free T Cell Antigen Receptor Related Molecules and Clinical Utilities of the Assays" concerns methods for diagnosing diseases and for monitoring diseased conditions by measuring the amount of soluble T cell antigen receptor in a subject's body fluid.

2.4. Hairy Cell Leukemia

Hairy cell leukemia (HCL) is a distinct form of chronic leukemia. Believed to be of B cell lineage, HCL is characterized by a slow proliferation of morphologically unique mononuclear cells bearing irregular cytoplasmic projections. Progressive infiltration of the spleen, liver and bone marrow results in varying degrees of anemia, thrombocytopenia and leukopenia and moderate to severe immunologic deficiencies (Golomb, H. M. and Vardiman, J., 1978, *CA—A Cancer Journal for Clinicians* 28:265-277). Accurate diagnosis is essential as the natural course, prognosis and therapeutic options for HCL characteristically differ from those of other hematologic malignancies. A definitive diagnosis is based on the examination of biopsy material from the bone marrow.

The bone marrow is always involved in HCL, and its histology is diagnostic (Cawley, J. C., et al., 1980, *Hairy Cell Leukemia*, Springer-Verlag, New York). Although circulating hairy cells are sometimes found in the peripheral blood, examination of the bone marrow is generally regarded as the best way to confirm diagnosis (id.) The most frequently used procedure is the bone marrow biopsy/histopathology procedure involving a collection of a core biopsy, fixation and sectioning, hematoxylin and eosin staining, and a light microscopic evaluation (Bardawil, R. G., et al., 1986, *Am. J. Clin. Path.* 85:194; Golomb and Vardiman, 1978, *CA—A Cancer Journal for Clinicians* 28:265-277; Spiers et al., 1987, *N. Engl. J. Med.* 316:825). The marrow characteristically shows a diffuse or focal infiltrate of mononuclear cells, with strikingly uniform nuclei, surrounded by a region of relatively clear cytoplasm, giving the infiltrate a spongy appearance (Golomb and Vardiman, 1978, *CA—A Cancer Journal for Clinicians* 28:265-277). The life threatening cytopenias of the hairy cell patient are directly related to the extent of leukemic infiltration of this organ, although the precise mechanism for bone marrow failure has not been determined (Cawley, J. C., et al., 1980, *Hairy Cell Leukemia*, Springer-Verlag, New York).

Due to the indolent nature of this disease, no major quantitative changes may be observed in the bone marrow of untreated patients over prolonged periods of time (Cawley et al., 1980, supra). Disease progression does, however, result in a gradual increase in the extent of leukemic infiltration, with a related decrease in hematologic indices (hemoglobin, granulocyte count and platelet count). Conversely, hairy cell infiltration of the bone marrow has been reported to decrease in patients undergoing treatment (Quesada, J. R., et al., 1984, *N. Engl. J. Med.* 310:15; Bardawil, R. G., et al., 1986, *Am. J. Clin. Pathol.* 85:194).

The value of the bone marrow biopsy/histopathology procedure, however, is decreased by its potential for providing unreliable measurements. False negative or positive results may occur due to the obtainment of non-representative specimens from bone marrows with a focal distribution of hairy cells (Golomb and Vardiman, 1978, *CA—A Cancer Journal for Clinicians* 28:265-277). They can also result from decreased sensitivity of the procedure when evaluating marrows with a low level of hairy cell infiltration.

The use of microscopic evaluations of the bone marrow in the diagnosis of HCL had become common practice in the United States and in Europe by the mid-1970s (Catovsky, D., 1977, *Clinics in Haematol.* 6:245; Golomb and Vardiman, 1978, *CA—A Cancer Journal for Clinicians* 28:265-277; Burke, J. S., 1978, *Am. J. Pathol.* 70:876; Vyukoupil, Thiele and Georgii, 1976, *Virchows Archive of Pathology, Anatomy & Histology* 370:273). By this time, procedures were also in place for using this in vitro diagnostic procedure to measure bone marrow tumor burden: to investigate the natural course of the disease and to determine when to initiate and discontinue therapy (Bouroncle, B., et al., 1958, *Blood* 13:609; Schrek, R. and Donnelly, W. J., 1966, *Blood* 27:199; Trubowitz, S., et al., 1971, *Blood* 38:288; Naim and Smith, 1974, *Cancer* 34:1813-1821; Golomb and Vardiman, 1978, *CA—A Cancer Journal for Clinicians* 28:265-277). In the 1980s, with the discovery of effective systemic therapy (alpha-interferon and deoxycoformycin), it was established that complete hematologic remission may occur months prior to bone marrow remission (Quesada, J. R., et al., 1984, *N. Engl. J. Med.* 310:15; Bardawil, R. G., et al., 1986, *Am. J. Clin. Pathol.* 85:194).

Bone marrow specimens are obtained by either needle aspiration or by biopsy, using a trephine device or large bore needle. Due to the frequency of obtaining a "dry tap" by aspiration, the more invasive biopsy procedure has become the preferred method for obtaining a marrow sample for microsopic evaluation (Vykoupil, K. F., et al., 1976, *Virchows Archive of Pathology, Anatomy, and Histology* 370:273; Burke, J. S., 1978, *Am. J. Pathol.* 70:876; Golomb, H. M. and Vardiman, J., 1978, *CA—A Cancer Journal for Clinicians* 28:265-277; Bardiwil, R. G., et al., 1986, *Am. J. Clin. Pathol.* 85:194). Although procedures vary among institutions, examination of Wright's stained smears of successful aspirate samples and/or hematoxylin and eosin stained paraffin sections of biopsy material are common practice.

The basis for estimating tumor burden in the bone marrow specimen is a hairy cell count (%) and a measurement of marrow cellularity (%) (Golomb, H. M., 1978, *Cancer* 2:946). More recently, the Leukemic Index (*Hairy Cell Index*), a value calculated from the product of the hairy cell count and the marrow cellularity, has come into use as a basis for estimating bone marrow response to splenectomy (Golomb and Vardiman, 1983, *Blood* 61:349) and to systemic therapy (Retain et al., 1985, *Blood* 65:644).

3. SUMMARY OF THE INVENTION

The present invention is directed to the measurement of soluble T cell growth factor receptors, soluble T cell differentiation antigens, or related soluble molecules or fragments thereof, and the use of such measurements in the diagnosis and therapy of diseases and disorders. The measurement of such molecules can be valuable in monitoring the effect of a therapeutic treatment on a subject, detecting and/or staging a disease in a subject, and in differential diagnosis of a physiological condition in a subject. These measurements can also aid in predicting therapeutic outcome and in evaluating and monitoring the immune status of patients.

In specific embodiments, measurements of interleukin-2 receptor levels can be made, to detect or stage leukemia or lymphoma. In other embodiments, soluble IL2R levels, or soluble CD8 levels, can be used to differentially diagnose renal allograft rejection, as distinguished from Cyclosporin A nephrotoxicity. A rise in serum IL2R over time in a patient can be used to predict renal allograft rejection. A rise in both soluble IL2R and creatinine in a body fluid of a patient can be used to predict allograft rejection or to differentially diagnose renal allograft rejection from infection in a transplant patient. In another embodiment, a change in serum IL2R concentrations in serial samples can be more sensitive than the absolute level of serum IL2R for the diagnosis of rejection.

The invention is also directed to the measurement of serum (soluble) IL2R levels to stage non-lymphatic malignancies.

In yet other embodiments, soluble IL2R measurements can be used as indicators of the extent of bone marrow leukemic infiltration in hairy cell leukemia patients.

In another aspect of the invention, an increase in concentration of soluble IL2R can indicate a diseased or immune-activated condition caused by lung cancer or smoking. A decrease in the level of soluble IL2R is indicative of more advanced disease in a patient with squamous cell lung carcinoma.

The invention is also directed to immunoassays which preferentially detect soluble CD4 over the cell-surface CD4.

An increase in soluble CD4 antigen levels in a sample from a patient can be used to diagnose a state of immune activation. Such an increase in soluble CD4 antigen levels in synovial fluid can be used to diagnose rheumatoid arthritis. Soluble CD4 measurements can also be used to stage adult T cell leukemia, or determine the phenotype of a cell in culture. Soluble CD4 measurements can also be used to monitor AIDS patients undergoing therapy.

The invention also relates to the measurement of a plurality of T cell surface markers for the detection, staging, or monitoring of a disease or disorder. In particular embodiments, the measurement of a plurality of soluble T cell surface markers and their change relative to one another can be superior to the measurement of any soluble T cell surface marker alone, for the detecting, staging, or monitoring of treatment of a disease or disorder.

In particular embodiments, measurements of the soluble T cell surface molecules can be accomplished by sandwich enzyme immunoassays.

3 1. Definitions

As used herein, the following abbreviations will have the meanings indicated:

| | |
|---|---|
| Staging a disease = | assessing the degree of severity according to standard classifications |
| AC = | adenocarcinoma |
| AZT = | azido-deoxythymidine |
| B-cell ALL = | B-cell acute lymphoblastic leukemia |
| CsA = | cyclosporin A |
| HC = | hairy cell leukemia |
| HTLV III/LAV/HIV = | Human T Cell Leukemia Virus Type I/Lymphadenopathy Associated Virus/Human Immunodeficiency Virus |
| IL-1 = | interleukin-1 |
| IL-2 = | interleukin-2 |
| IL2R = | interleukin-2 receptor |
| mAb = | monoclonal antibody |
| NHL = | non-Hodgkin's lymphoma |
| PBMC = | peripheral blood mononuclear cell |
| PHA = | phytohemagglutinin |
| RF = | rheumatoid factor |
| SCLC = | squamous cell lung carcinoma |
| Spontaneous release = | release by normal or pathologic physiological processes of the cell |

4. Description of the Figures

FIG. 1. In vitro experiments in T cell activation.

FIG. 1A: plot of concentration of soluble IL2R assayed in culture supernatants, cell lysates or cell surface of PHA stimulated human peripheral blood cells in culture.

Figure 1B:
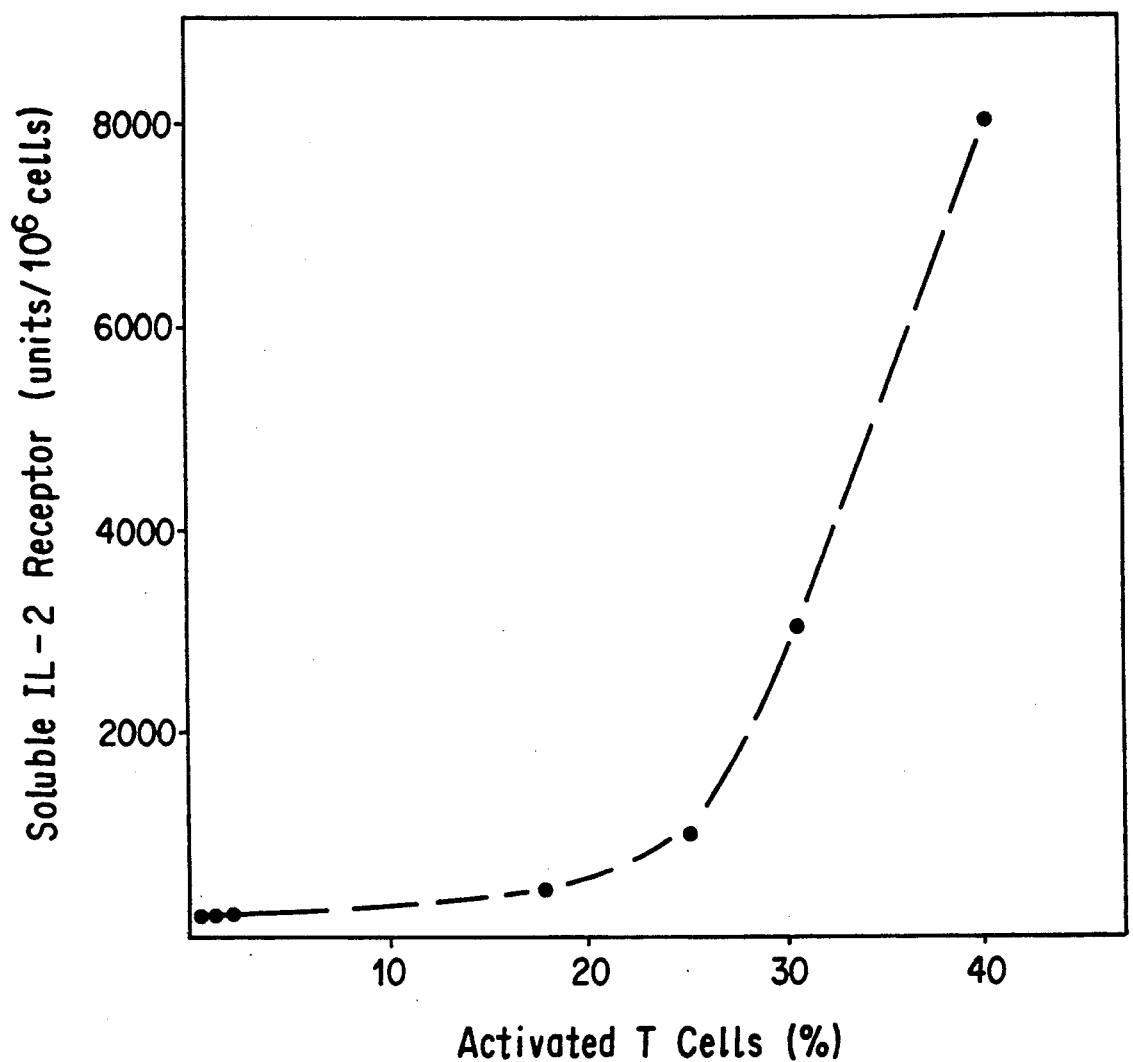

FIG. 1B: plot of concentration of soluble IL2R versus the percentage of activated T cells in culture.

Figure 2:
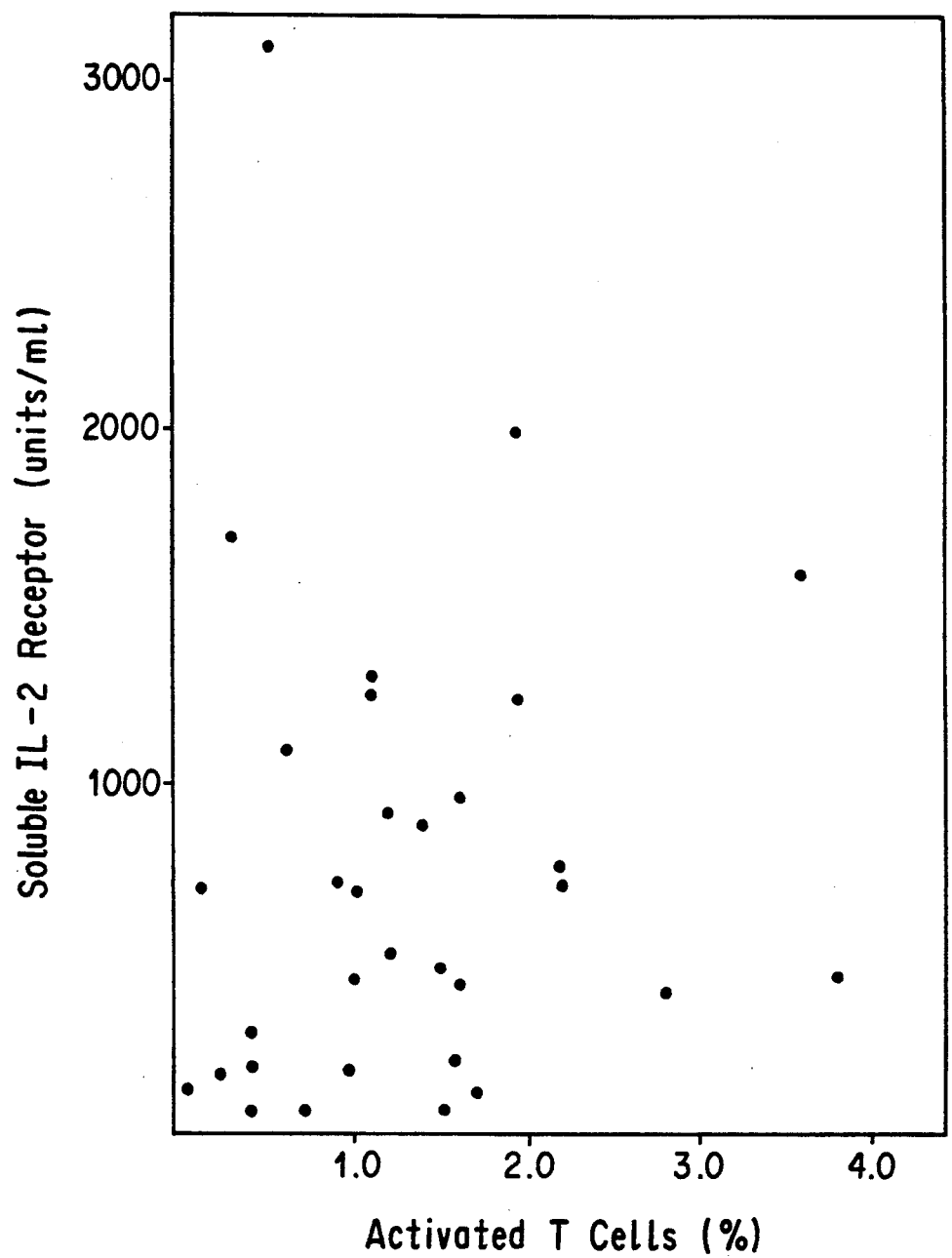

FIG. 2. Soluble (serum) IL-2 receptor versus cell surface IL-2 receptor in vivo.

Figure 3:
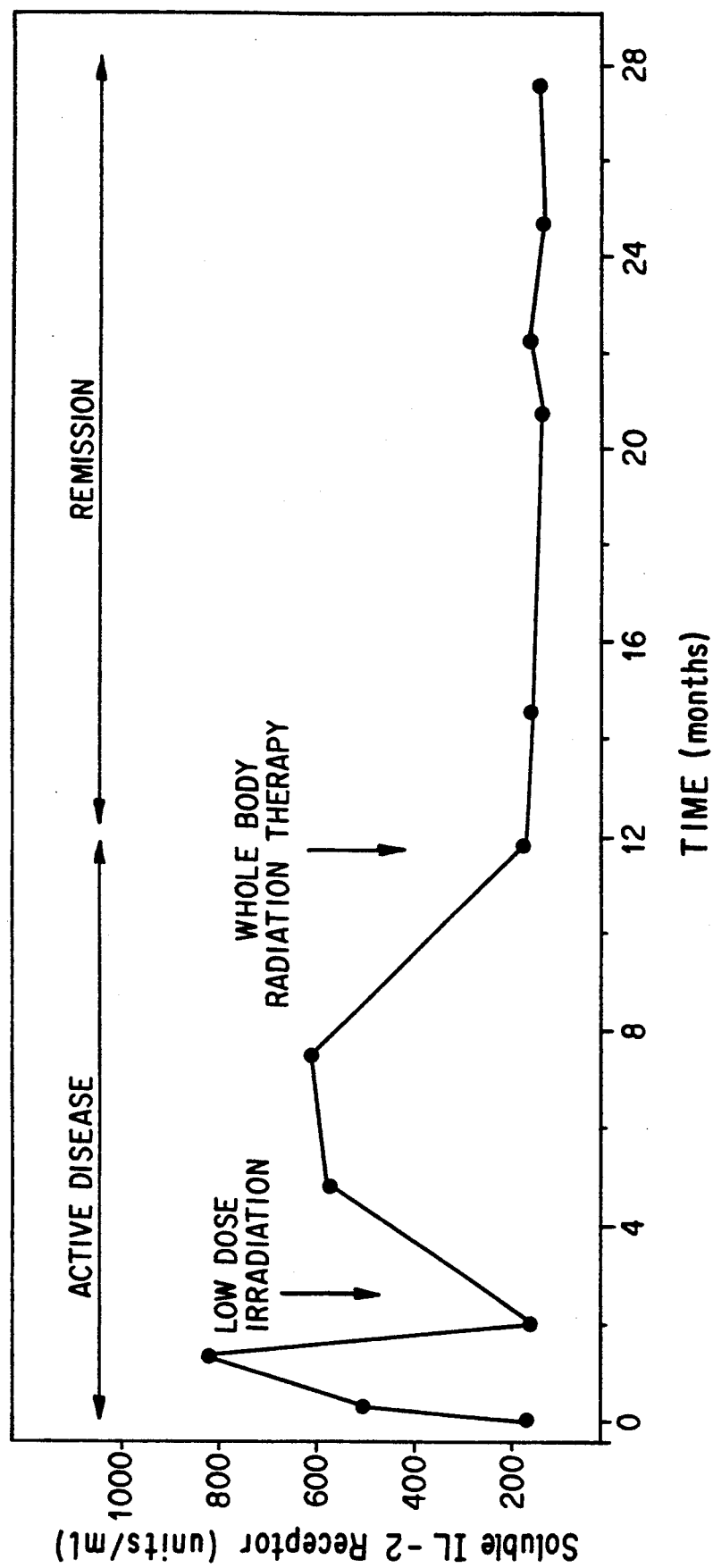

FIG. 3. Monitoring therapeutic treatment in cancer patients. Patient serum concentration of soluble IL2R is plotted against time. Time periods of active disease, treatment and remission are indicated.

Figure 4:
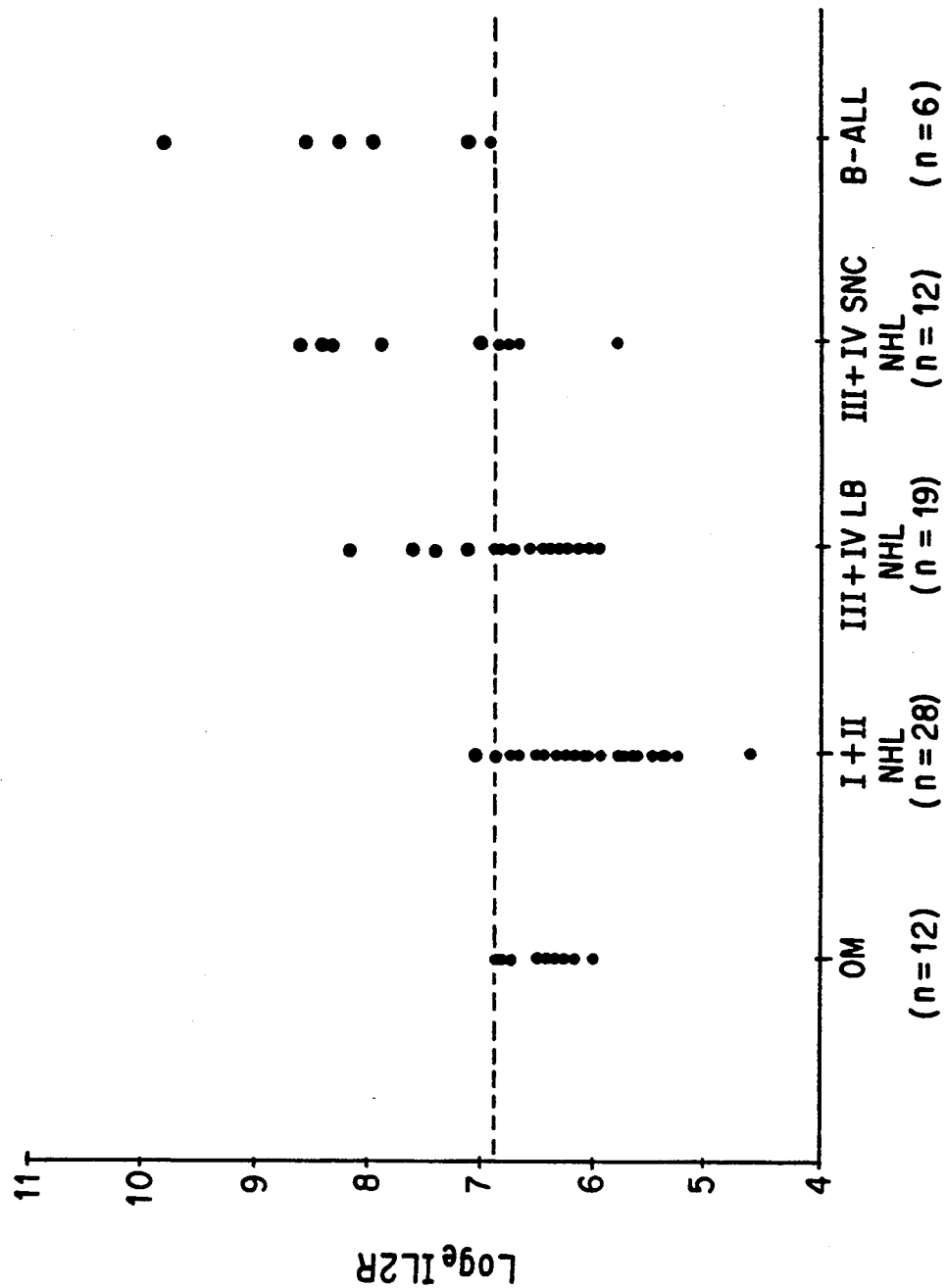

FIG. 4. Distribution of serum interleukin-2 receptor (IL2R) levels among children with otitis media (OM); stage I or II non-Hodgkin's lymphomas (NHL); stage III or IV lymphoblastic (LB) NHL; stage III or IV diffuse small noncleaved-cell (SNC) NHL; and B-cell acute lymphoblastic leukemia (B-ALL). The dashed line separates IL2R values above or below 1000 U/ml.

FIG. 5. Comparison of log serum interleukin-2 receptor (IL2R) levels and log serum lactic dehydrogenase (LDH) levels. The straight line represents the least-squares regression fit to the data.

FIG. 6. Comparison of time-to-failure rates according to serum interleukin-2 receptor levels (IL2R) for (A) all patients with non-Hodgkin's lymphoma and B-cell acute lymphoblastic leukemia; (B) patients with stage III or IV non-Hodgkin's lymphoma or B-cell acute lymphoblastic leukemia. Significantly worse treatment results were evident for patients with higher levels (greater than 1000 U/ml) in both comparisons.

Figure 7:
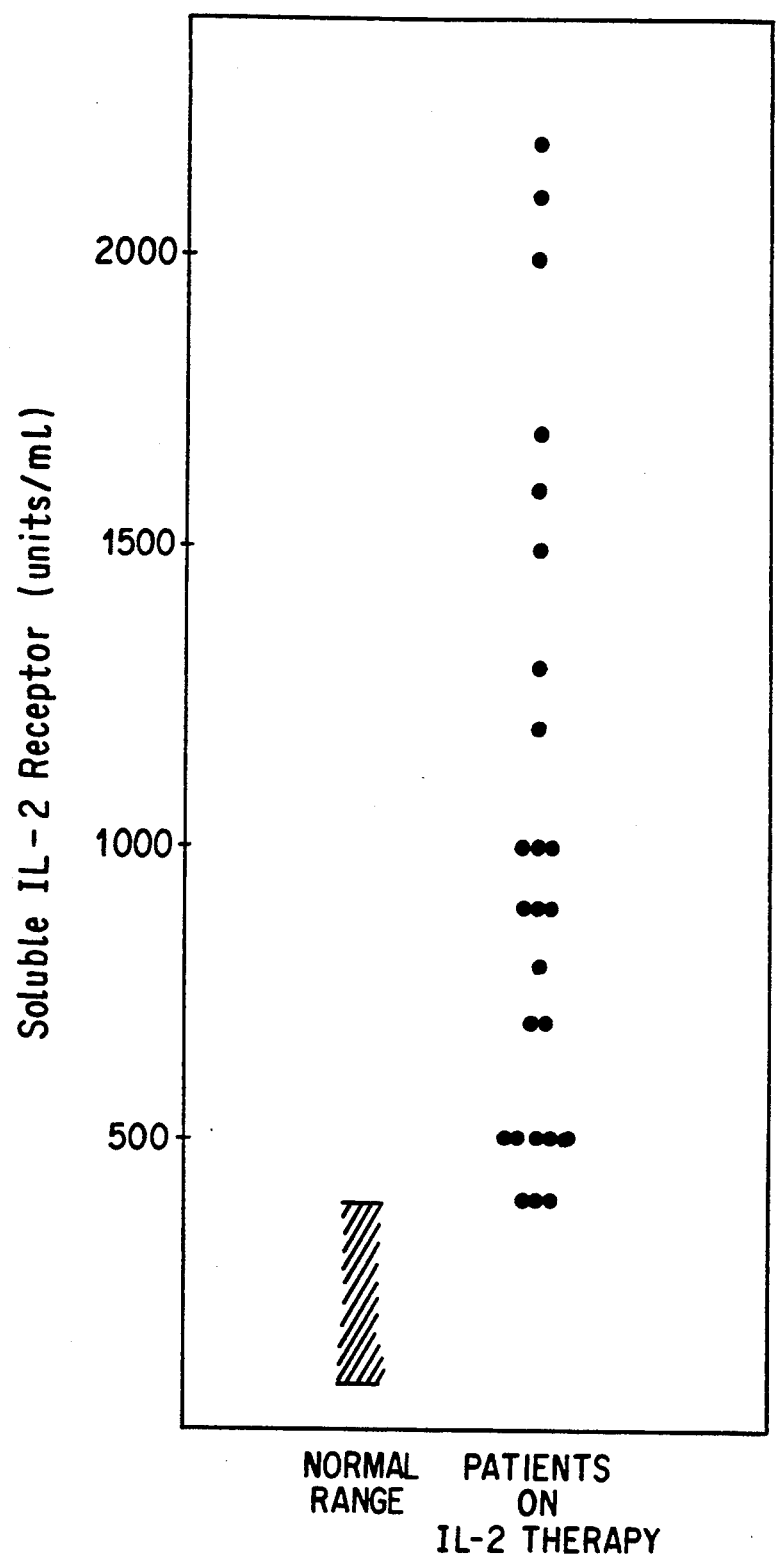

FIG. 7. Level of soluble (serum) IL-2 receptor in samples obtained from patients undergoing therapeutic treatment with IL-2.

Figure 8:
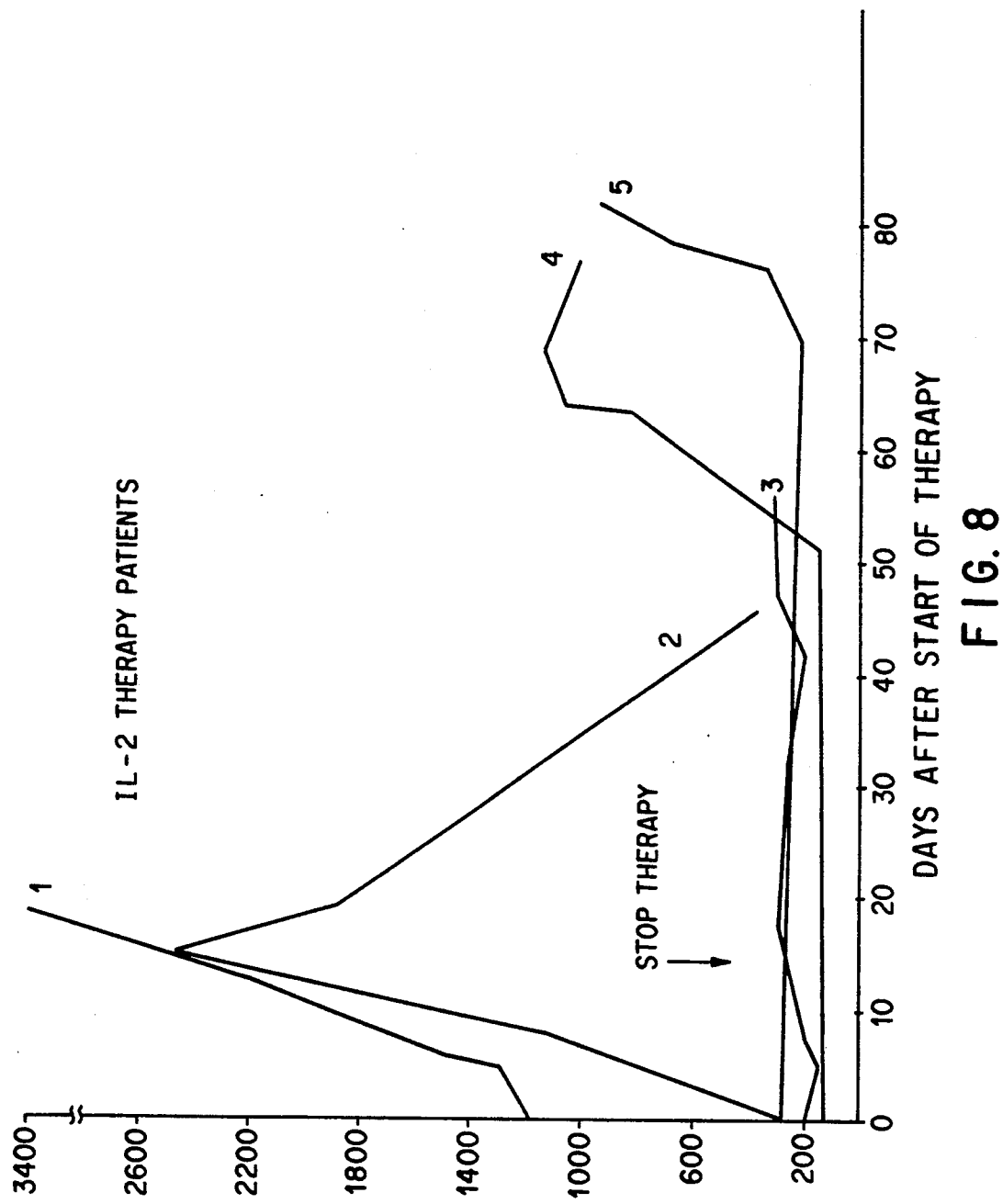

FIG. 8. Serum IL2R levels in patients with lung carcinoma receiving IL-2 therapy. All patients were infused continuously from day 0 to 14 with recombinant IL-2. Patients 1 and 2 received $3 \times 10^6$ U/ml whereas patients 3, 4 and 5 received $2 \times 10^6$ U/ml.

Figure 9:
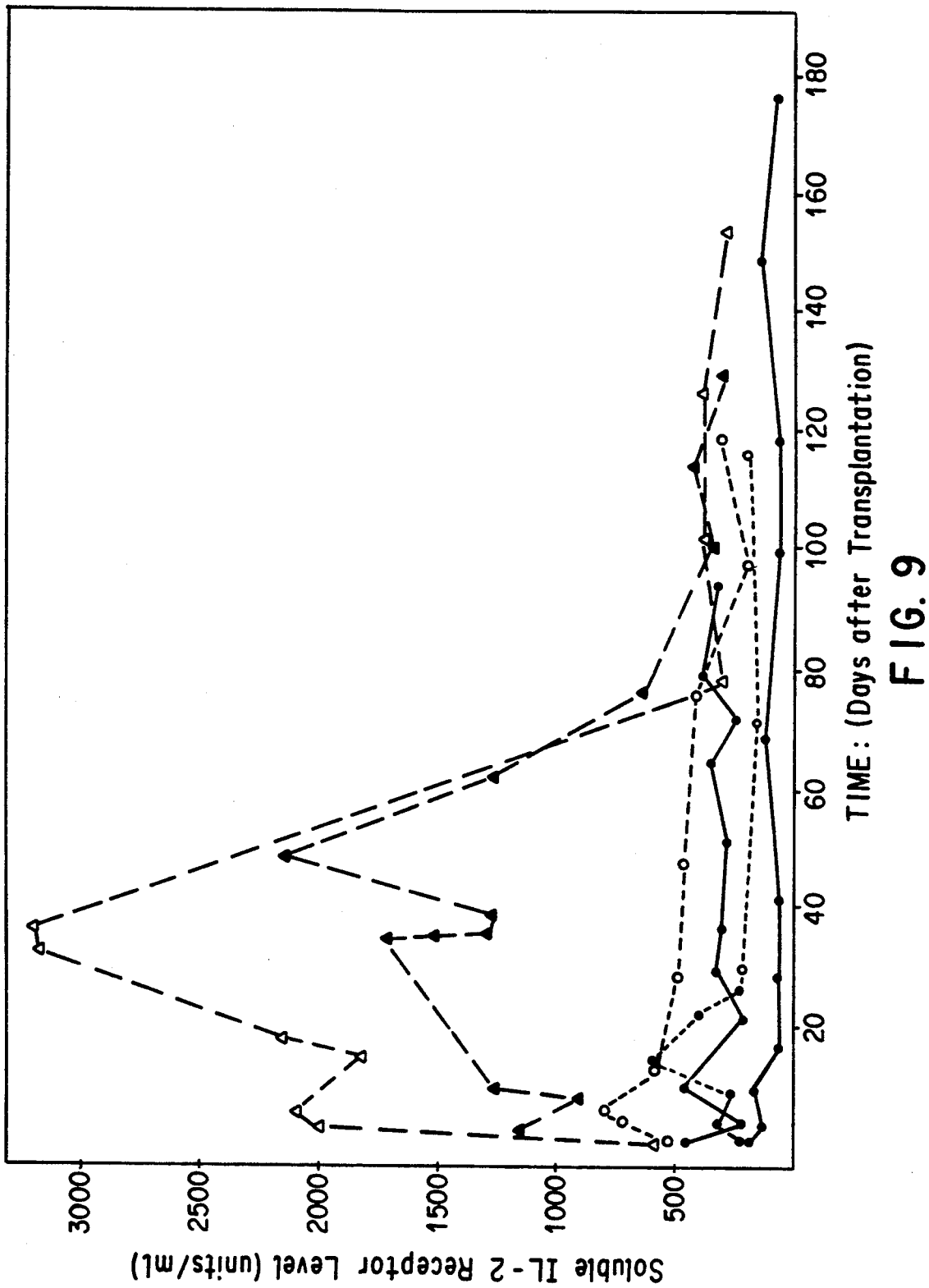

FIG. 9. Transplantation monitoring and differential diagnosis of immune-rejection from Cyclosporin A toxicity (open triangles=patients with rejection; open circles=patients with CsA toxicity; closed circles=stable renal transplant patients).

Figure 10:
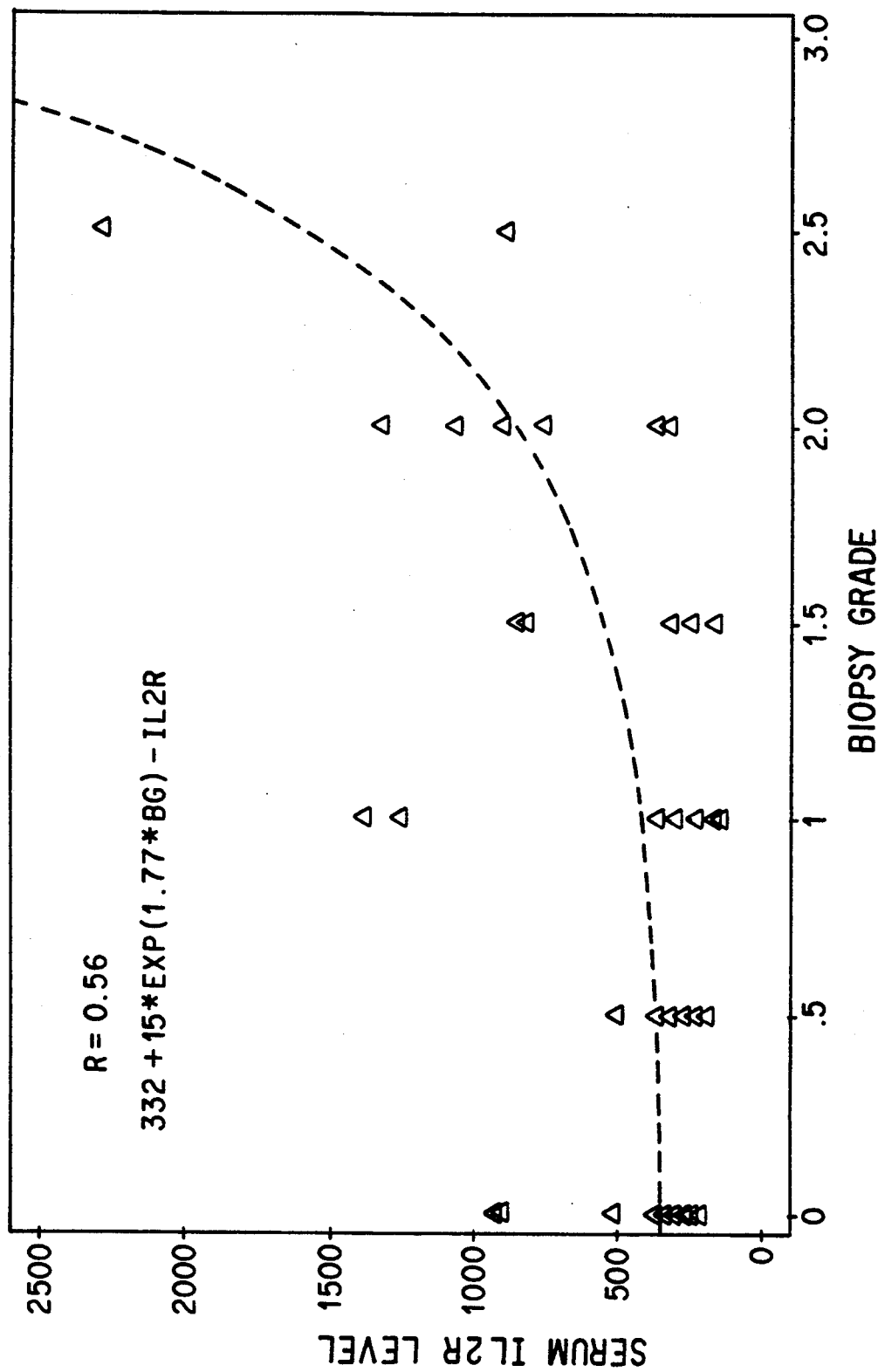

FIG. 10. Scatter plot of serum IL2R measurements (open triangles) versus histological grade of corresponding endomyocardial biopsy with superimposed non-linear regression plot (dashed curve). The equation for the regression is shown in the upper left of the plot below the linear correlation coefficient (R). EXP=exponent, BG=biopsy grade.

FIG. 11. Graph for patient A shows serum IL2R levels (open triangles) and biopsy grade (open squares) versus time for Patient A who has had an uneventful post transplant course. The patient was treated with additional steroids because of clinical signs of early rejection. Plot of data for Patient B shows correlations of IL2R levels and biopsy grade. This patient was transplanted during an episode of recurrent myocarditis perhaps resulting in the initial high value of IL2R. During rejection therapy with additional steroids, the biopsy grade remained at 2.0 (resolving rejection) but the IL2R fell to normal, i.e. below 545 units/ml. On day 60 post transplant, the biopsy grade fell to 1.0 but the IL2R level rose while the patient was receiving ATG. The biopsy grade 11 days later was 2.5 and the IL2R level was 2298 units/ml indicating recurrent rejection. S-M=Solumedrol. ATG=anti-thymocyte globulin, OKT-3=Orthoclone OKT3.

Figure 12:
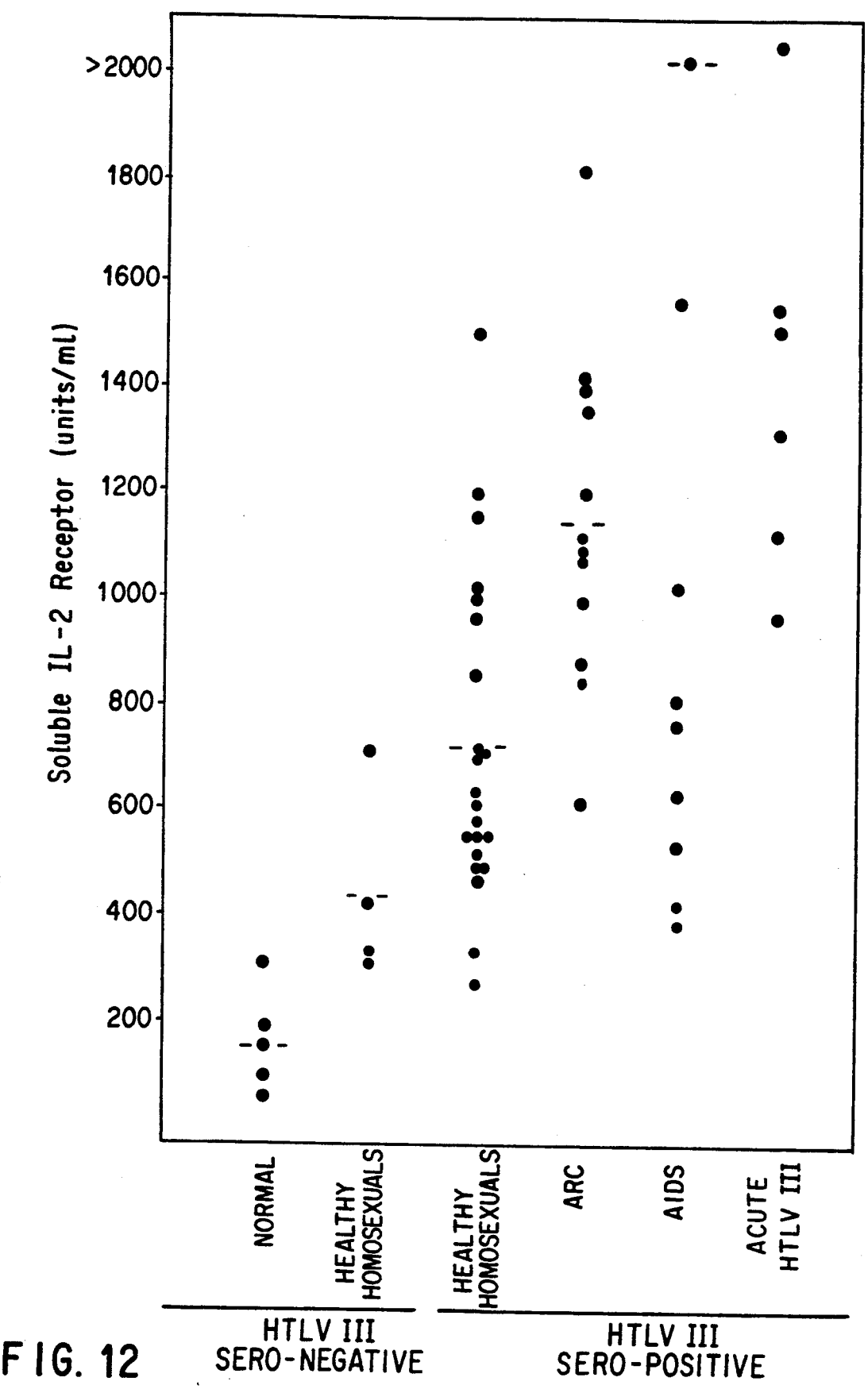

FIG. 12. Staging of viral infection. Plot of serum levels of soluble IL2R of AIDS patients clinically diagnosed as indicated.

Figure 13:
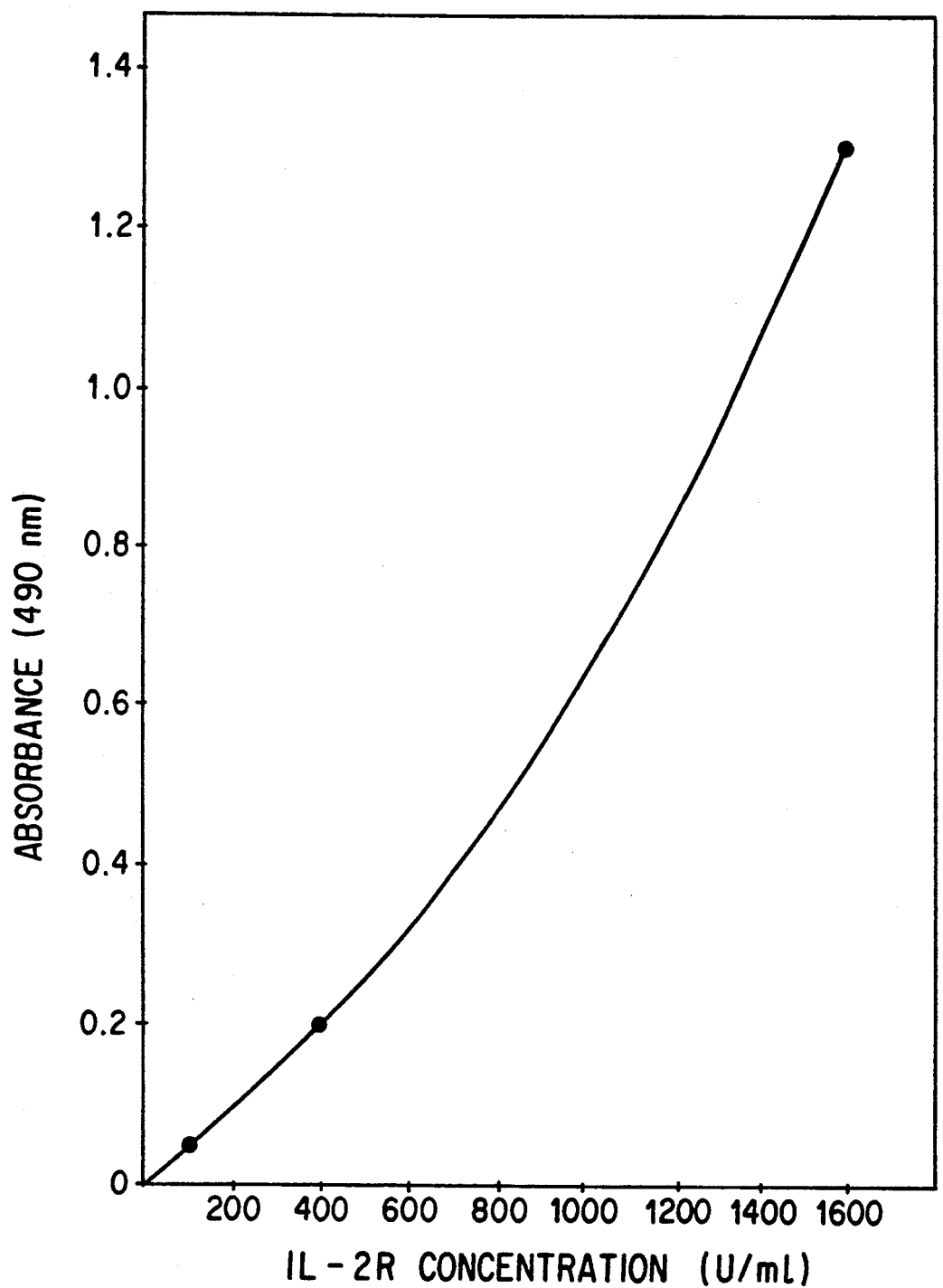

FIG. 13. Typical standard curve for measurement of soluble IL2R using the CELLFREE ® assay.

Figure 14:
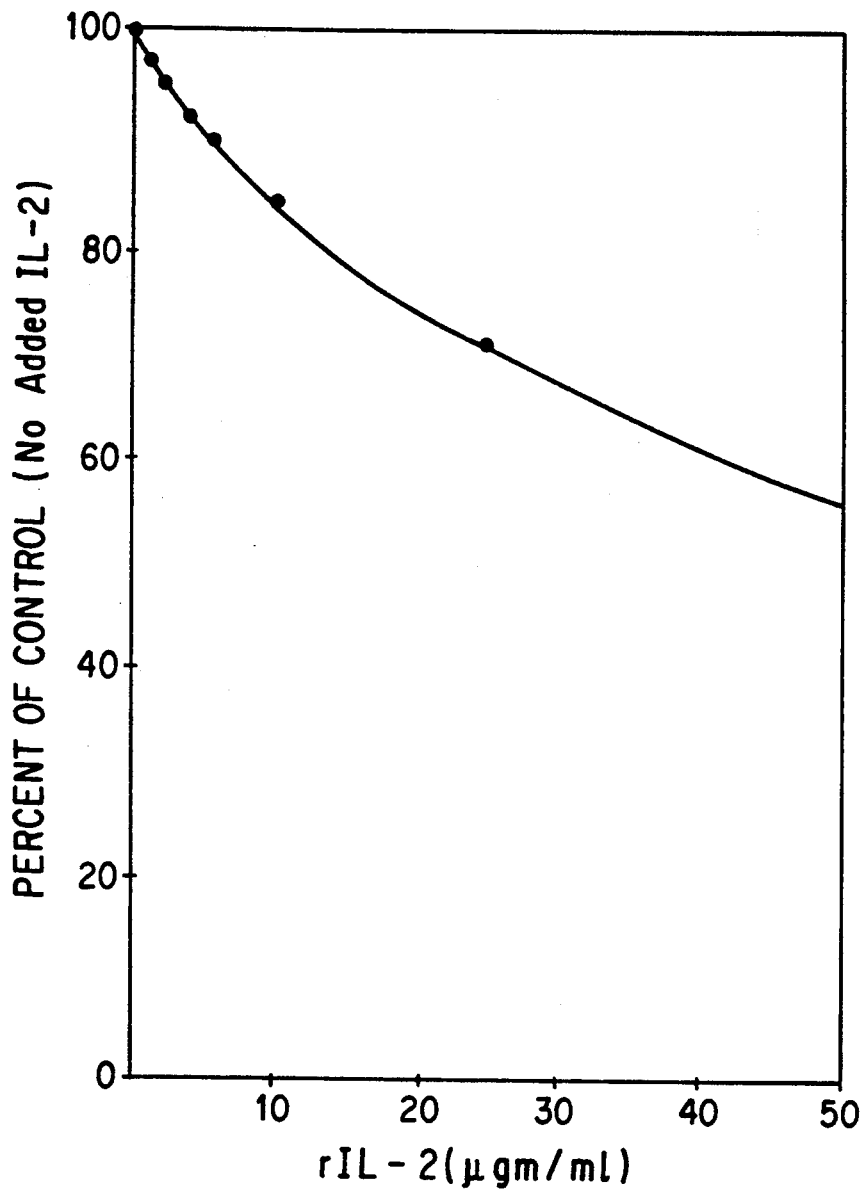

FIG. 14. Effects of addition of recombinant IL-2 on the CELLFREE ® serum assay kit performance.

Figure 15:
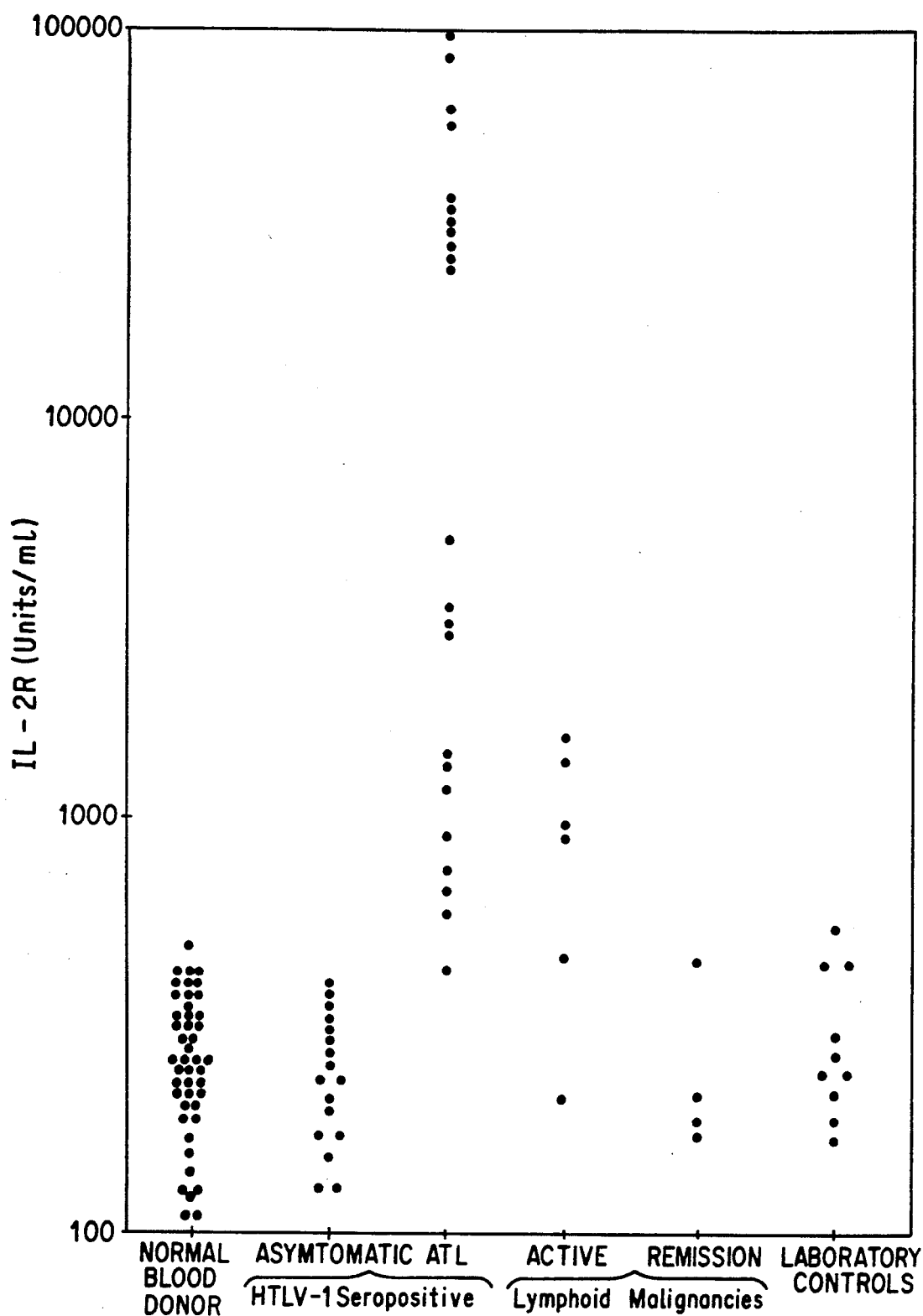

FIG. 15. Levels of serum IL2R in normal healthy donor and patients with diseases as measured using the IL2R CELLFREE ® assay.

Figure 16:
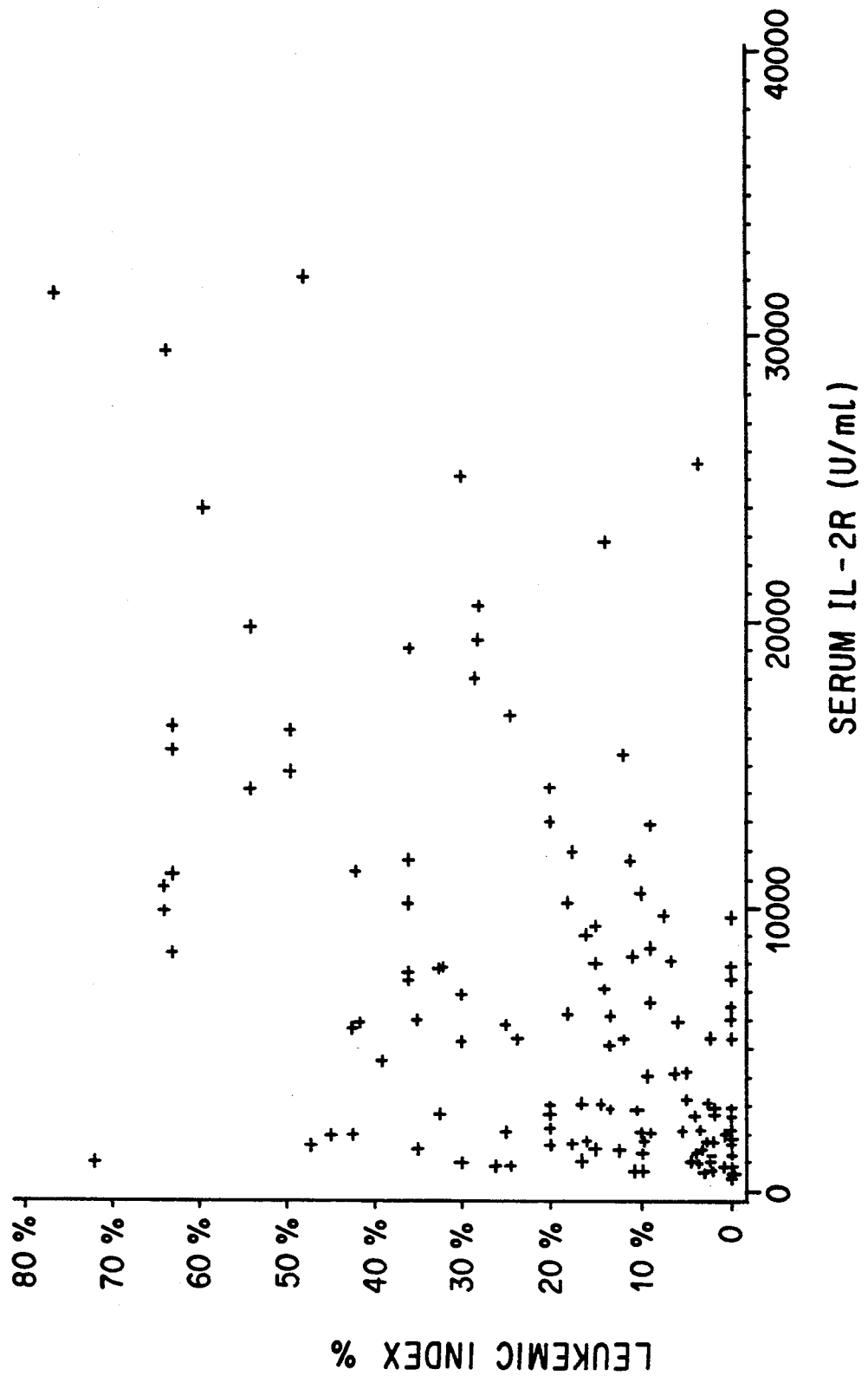

FIG. 16. Correlation (r) between serum IL2R (U/ml) and bone marrow % leukemic index, for observations on treatment.

Figure 17:
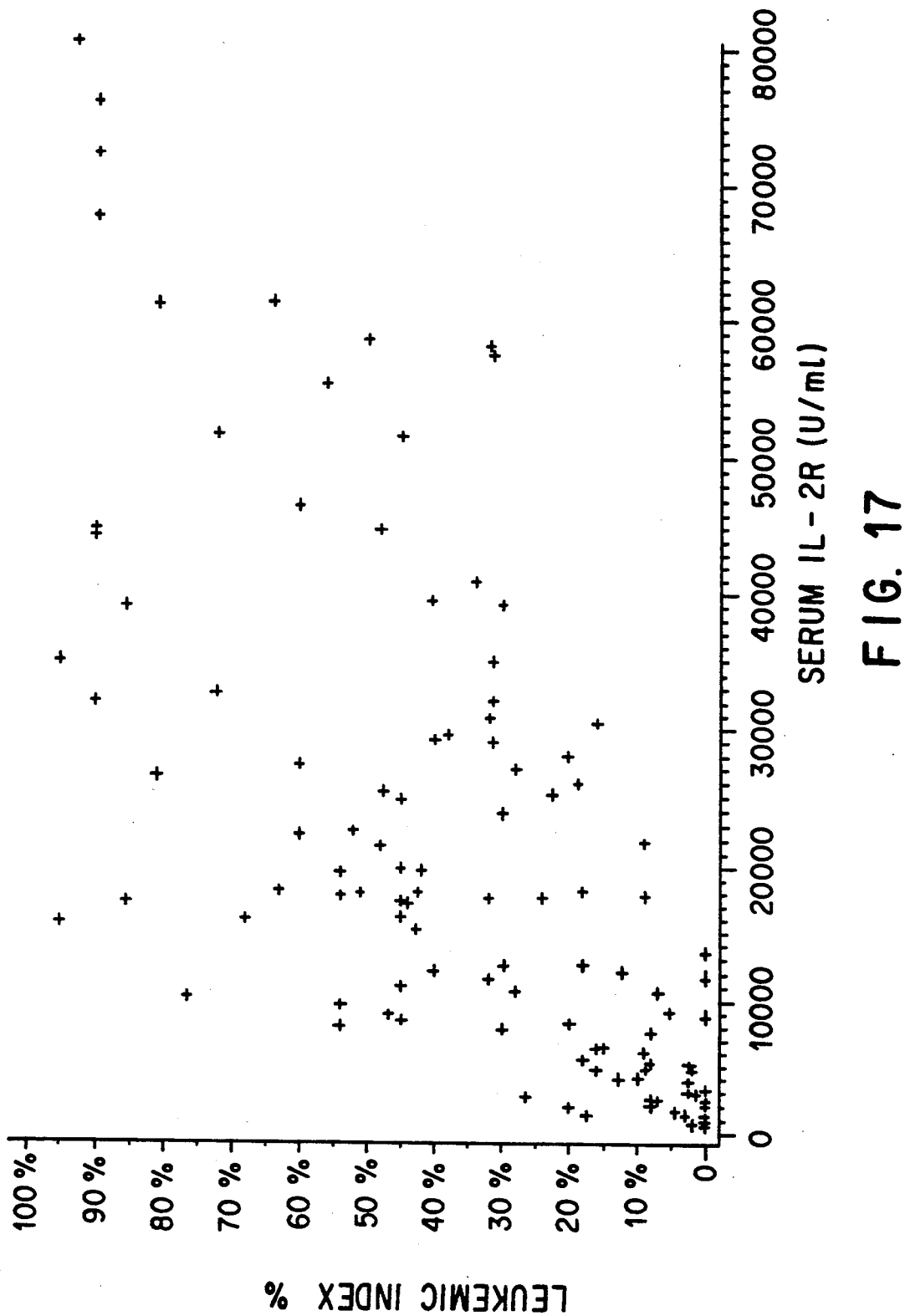

FIG. 17. Correlation (r) between serum IL2R (U/ml) and bone marrow % leukemic index, for observations off treatment.

Figure 18:
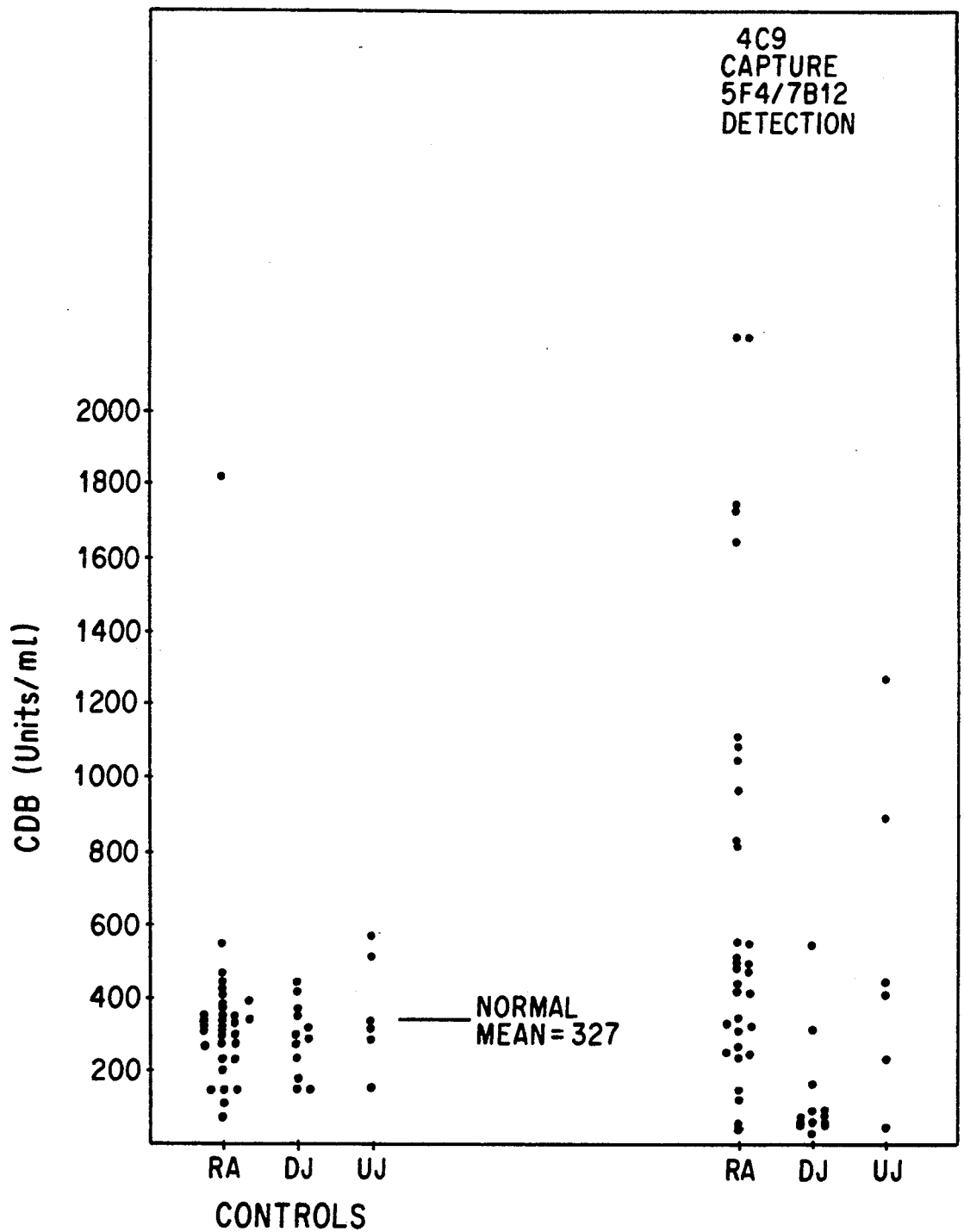

FIG. 18. Distribution of CD8 levels in serum and synovial fluids among patients with rheumatoid arthritis (RA), degenerative joint disease (DJ) and unclassified joint disease (UJ). Data at left indicate CD8 levels in control healthy patients for each series of assays.

Figure 19:
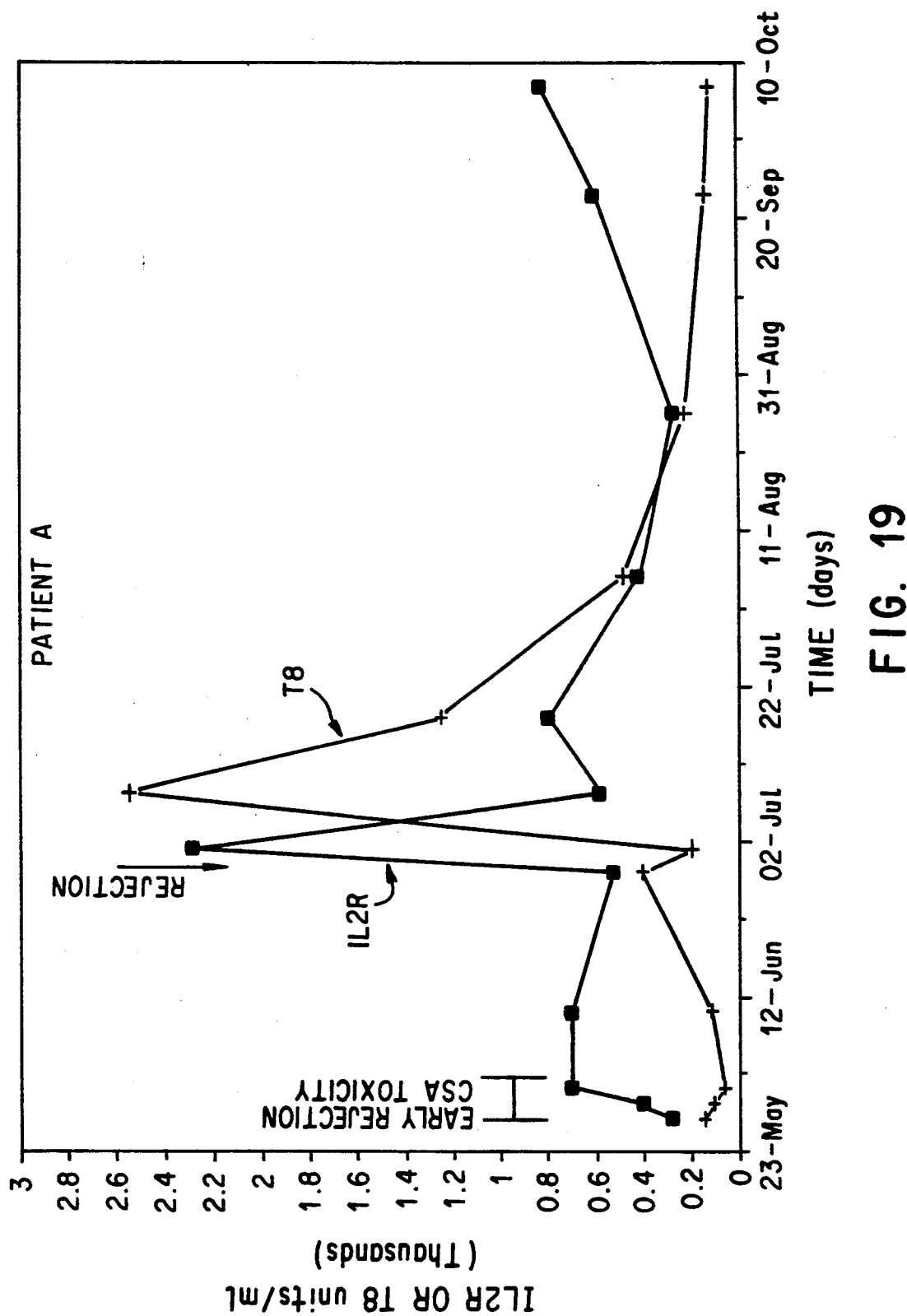

FIG. 19. Monitoring of a renal transplantation patient for serum CD8 and serum IL2R. Serum levels of either soluble IL2R or soluble CD8 are plotted against time. Episodes of CsA toxicity and rejection are indicated.

Figure 20:
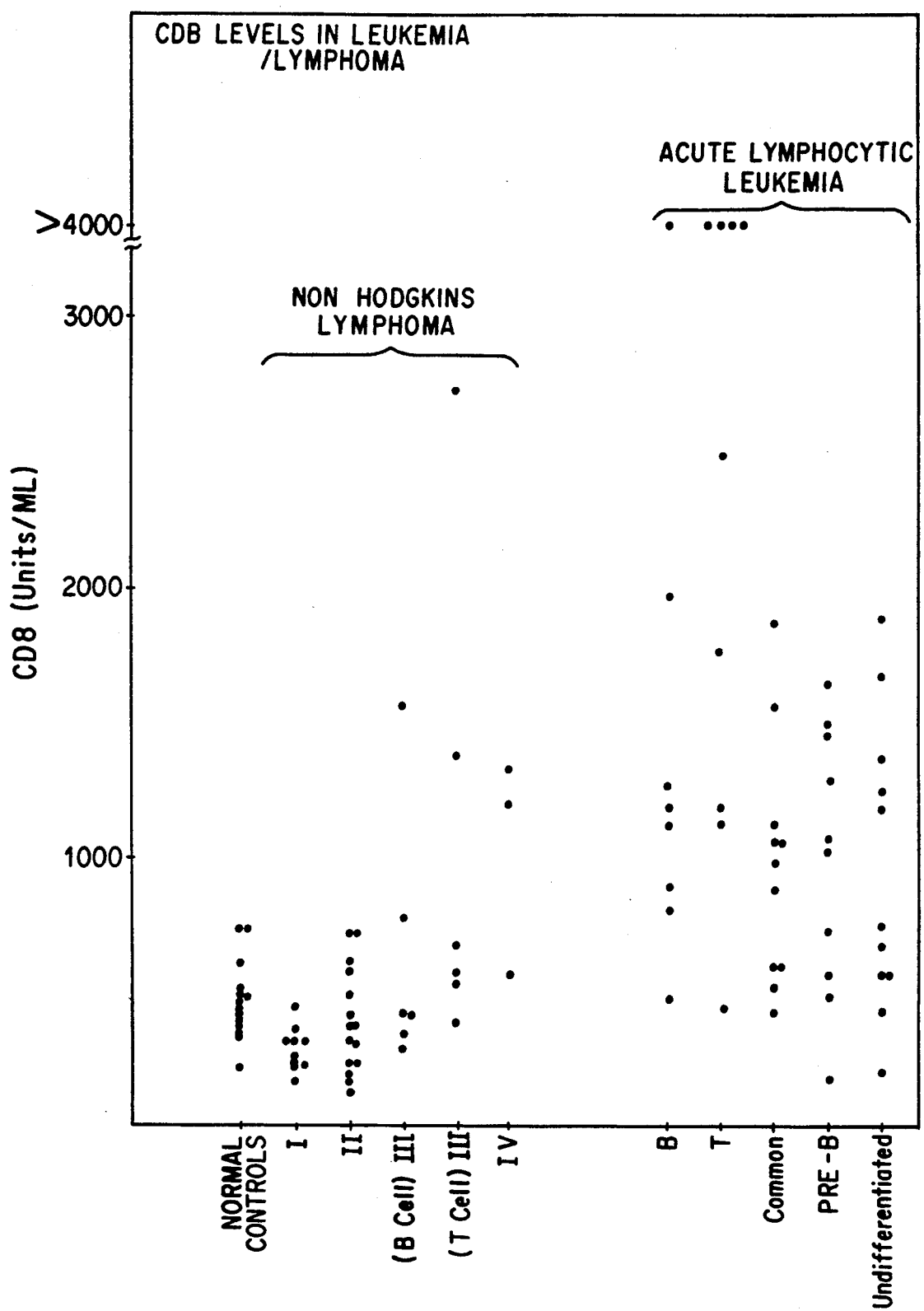

FIG. 20. Distribution of serum CD8 levels in children with non-Hodgkins lymphoma (NHL) and acute lymphoblastic leukemia (ALL). CD8 antigen was detected using mAb 4C9 as capture reagent and mAb 5F4/7B12 as detection reagent in a sandwich immunoassay.

Figure 21:
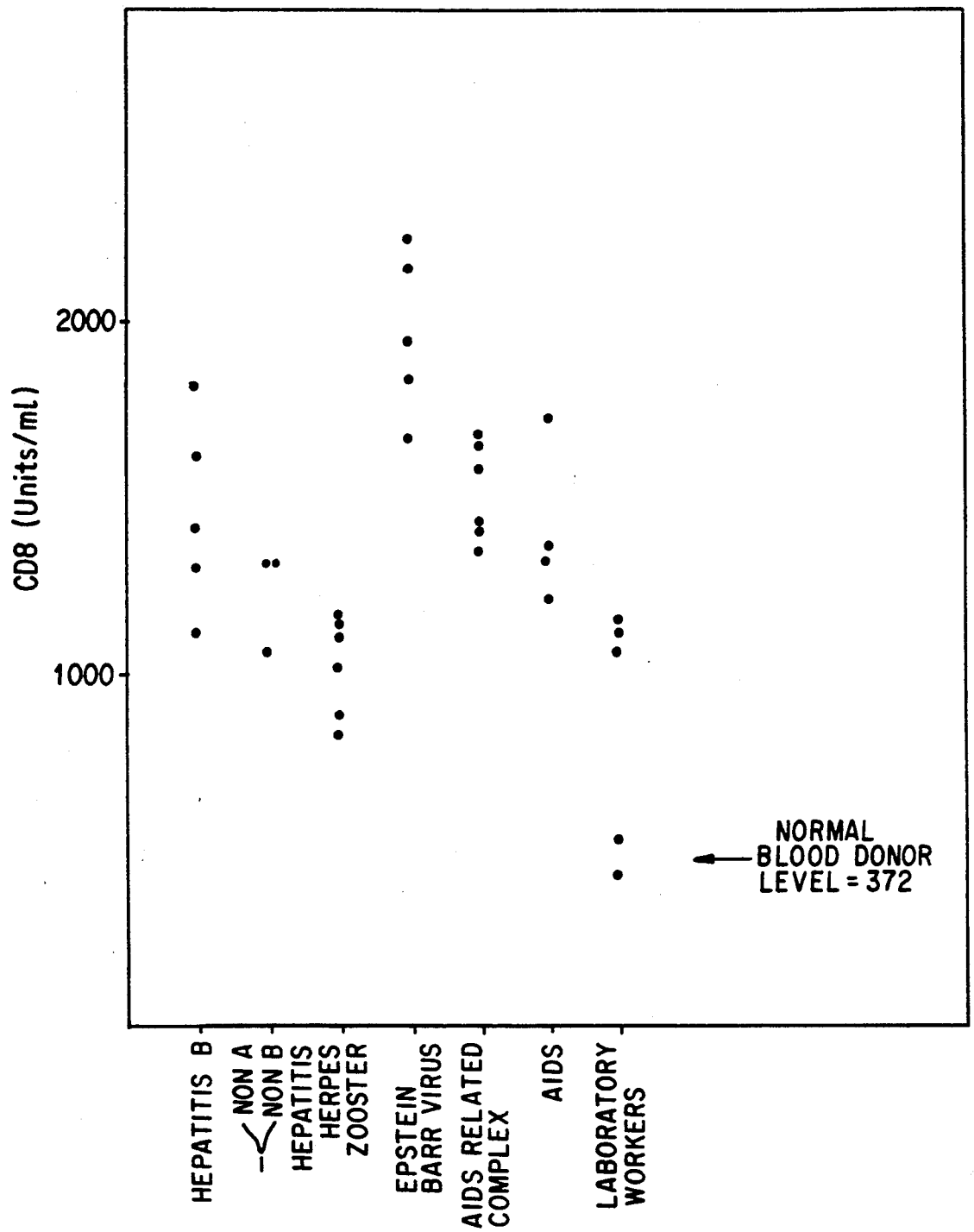

FIG. 21. Distribution of serum CD8 levels in patients with infectious disease. CD8 antigen was detected using mAb 4C9 as capture reagent and mAb 5F4/7B12 as detection reagent in a sandwich immunoassay.

Figure 22:
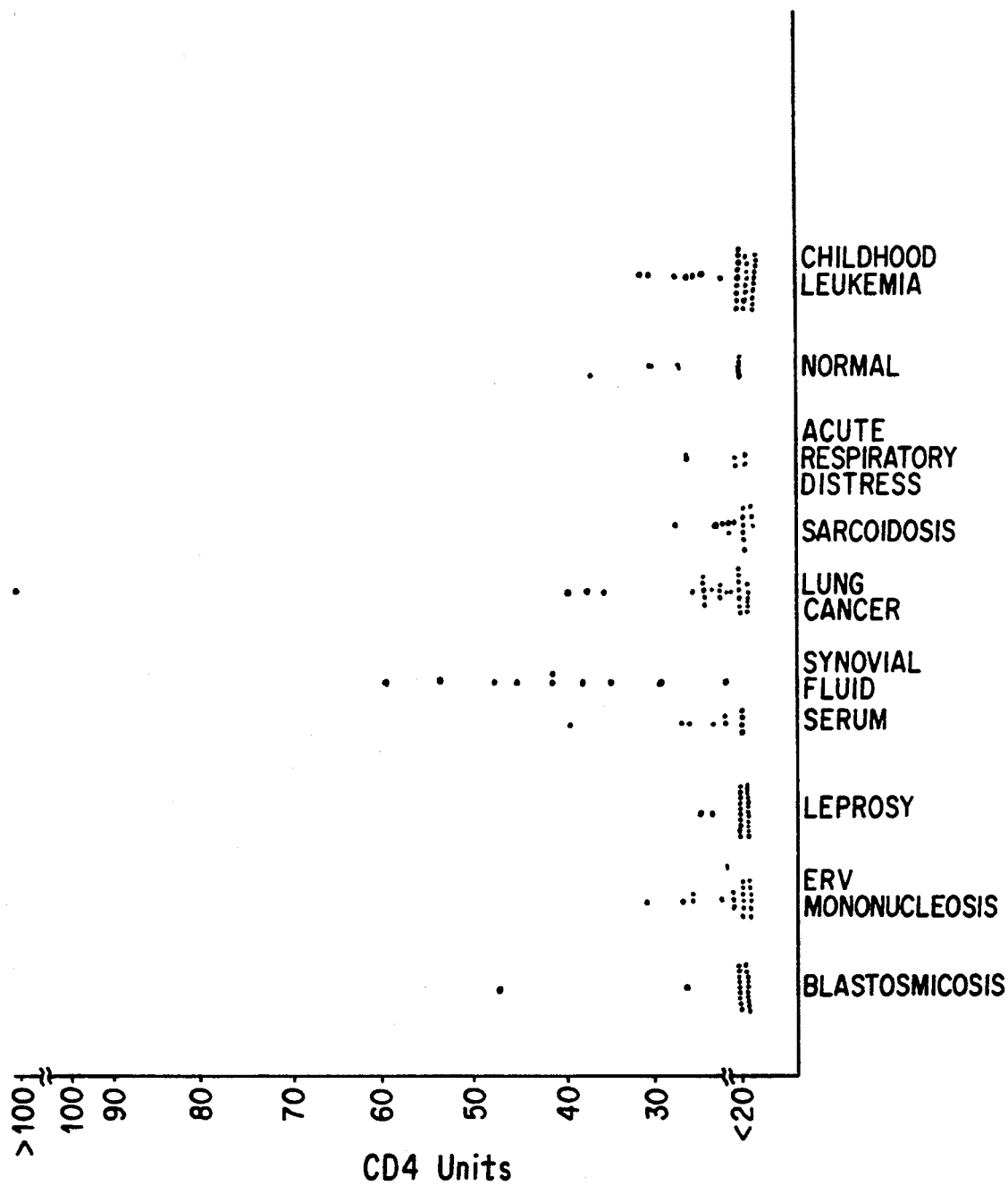

FIG. 22. Levels of soluble CD4 in sera of normal individuals and patients from a number of disease groups. The assay used was as described in Section 23.2.1, infra. CD4 antigen was detected using mAb 8F4 as capture reagent and mAb R2B7 as detection reagent in a sandwich immunoassay. The limit of sensitivity for the assay was 20 units.

Figure 23:
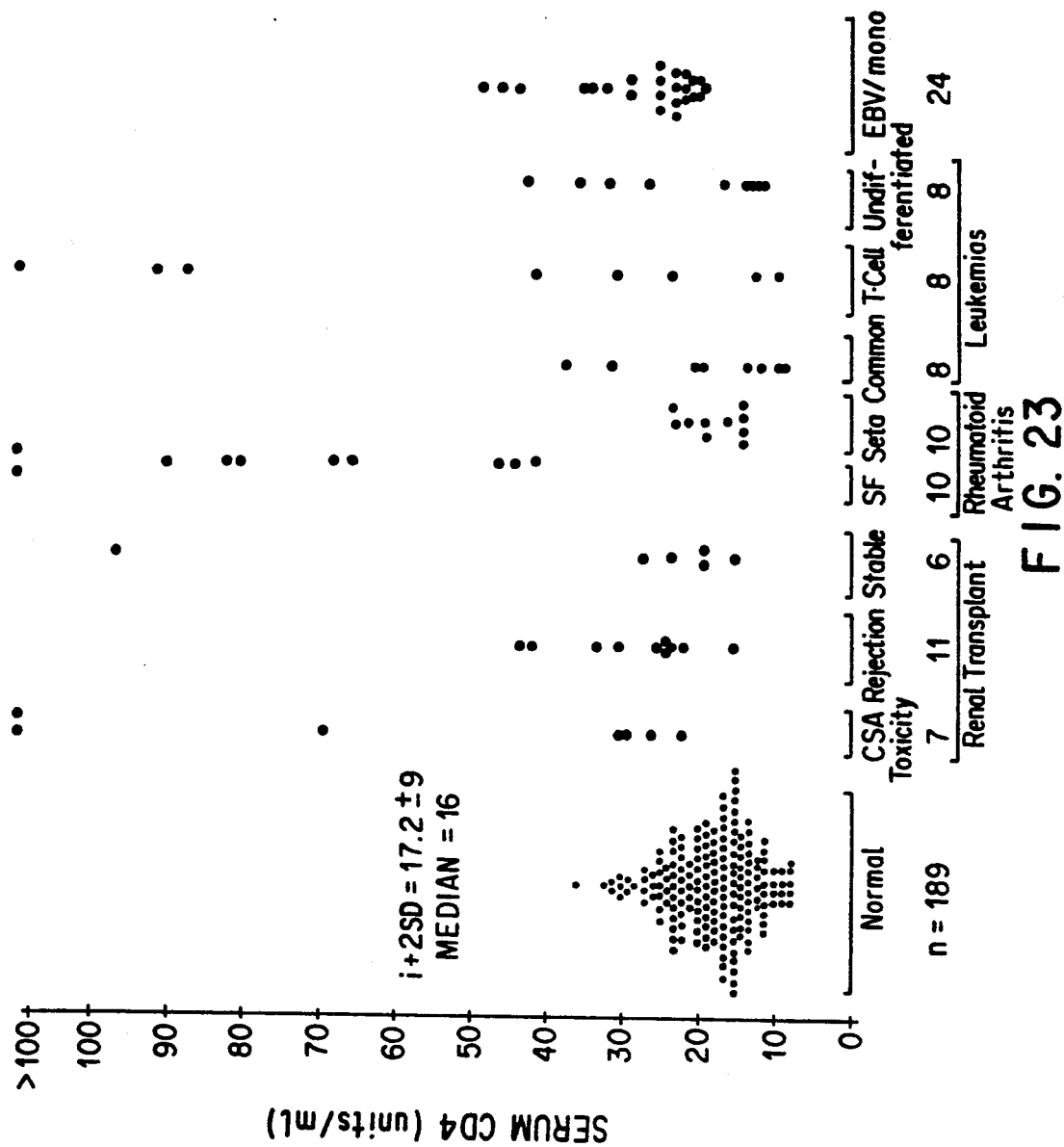

FIG. 23. Levels of soluble CD4 in sera of normal individuals and patients from a number of disease groups. The assay used was as described in Section 23.2.2, infra. SF: synovial fluid; EBV/mono: Epstein Barr Virus/mononucleosis.

Figure 24A:
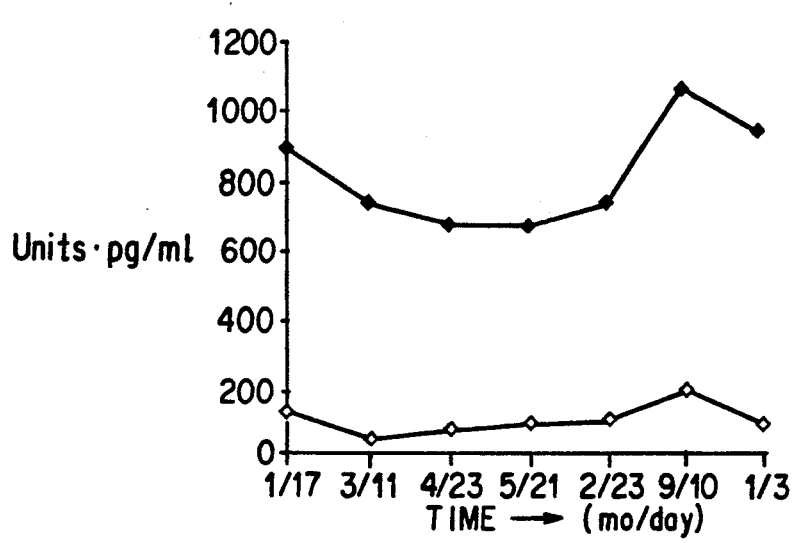
Figure 24B:
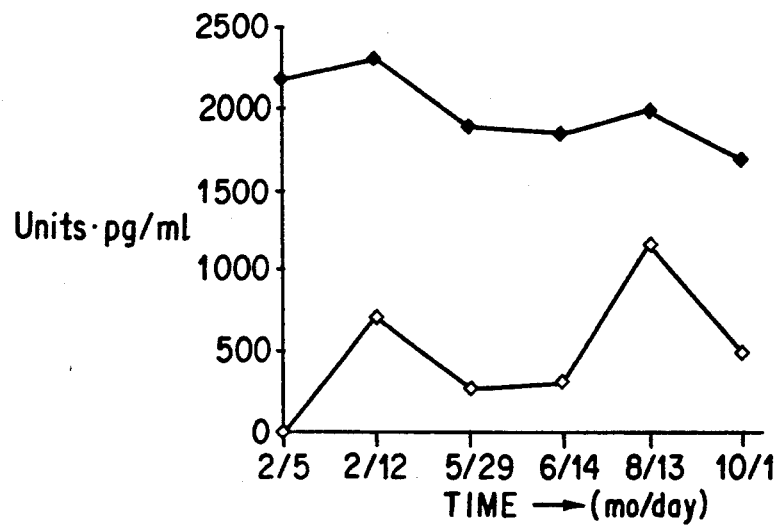
Figure 24C:
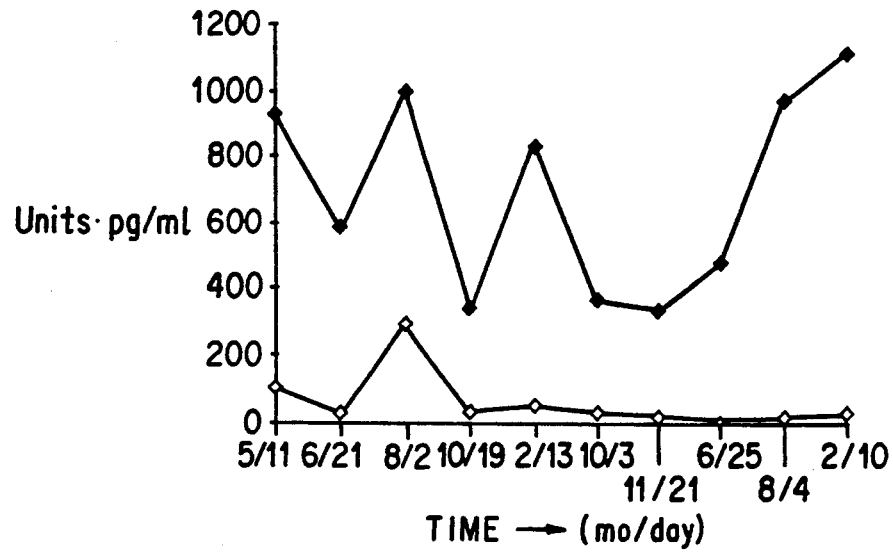

FIG. 24. Longitudinal studies of soluble CD8 levels in sera of patients with Kaposi's sarcoma (KS) or with AIDS-related complex (ARC). Closed diamonds: soluble CD8 levels (U/ml); Open diamonds: HIV p24 levels (pg/ml)×10.

Figure 25A:
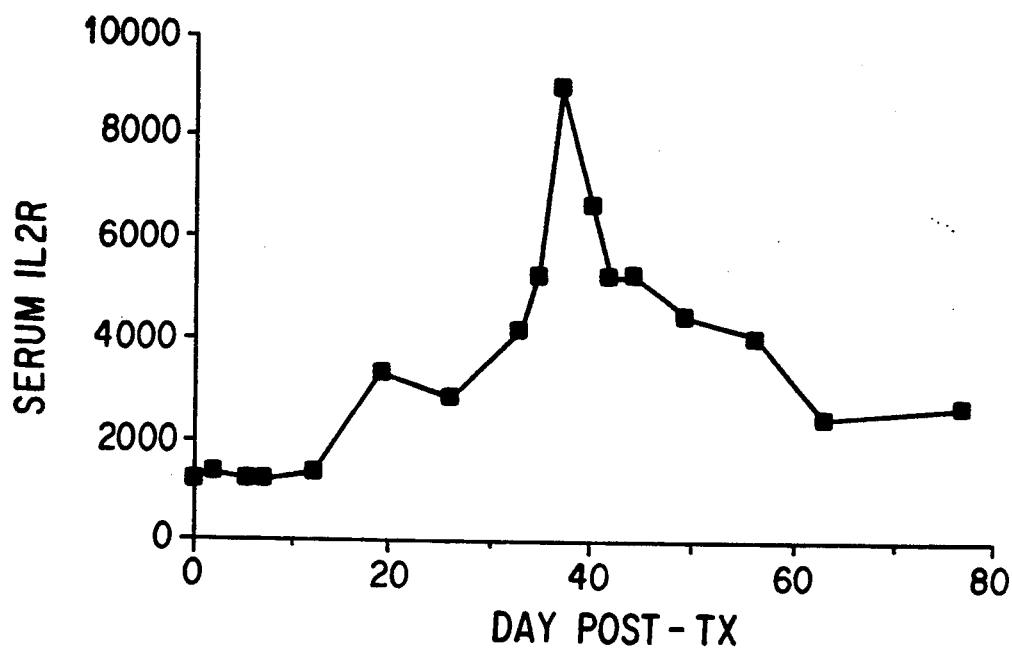
Figure 25B:
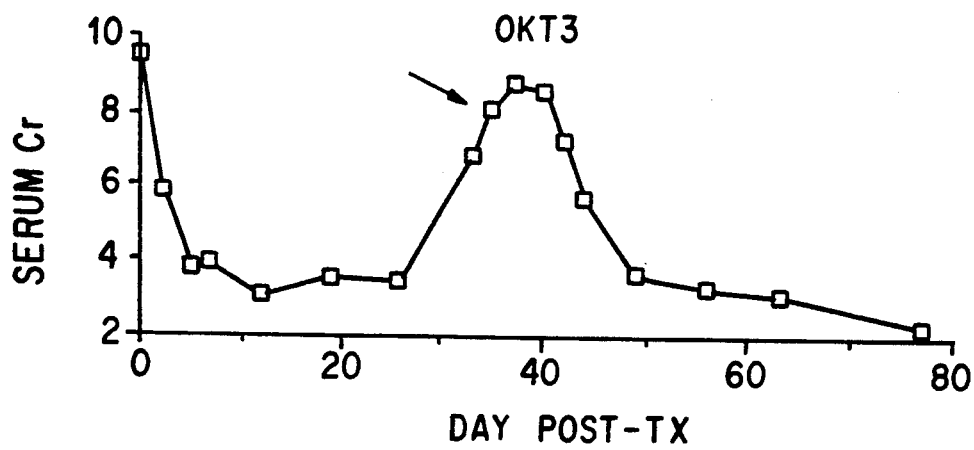

FIG. 25. Serial serum IL2R (units/ml) and creatinine (Cr) (mg/dl) levels in a renal allograft recipient who developed a rejection episode that responded to OKT3 antibody therapy (arrow marks day of biopsy diagnosis). The rise in serum IL2R accompanied and preceded the rise in serum creatinine.

Figure 26A:
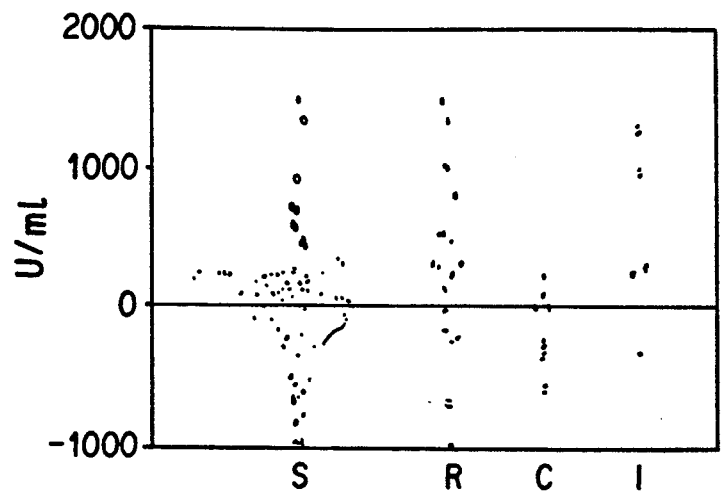
Figure 26B:
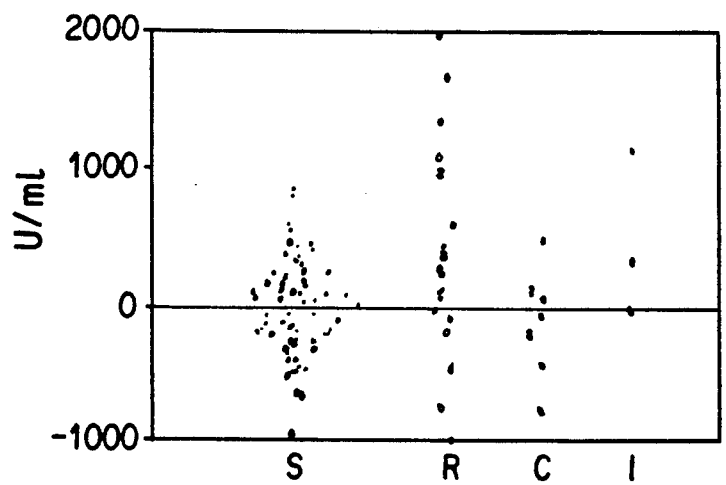
Figure 26C:
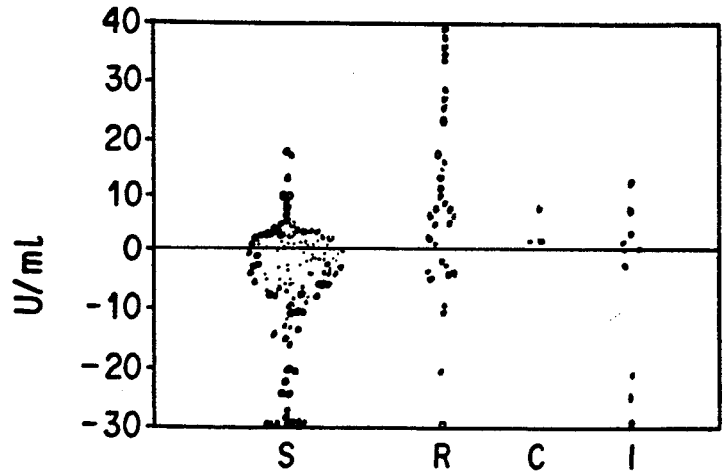

FIG. 26. Dot plots of the change in serum IL2R (A), urine IL2R (B), or serum creatinine (Cr) (C) concentrations by clinical status: stable (S), rejection (R), cyclosporine toxicity (C), and infection (I). Samples of rejection are from 2 days before the first rise in Cr to the time of institution of antirejection therapy.

Figure 27:
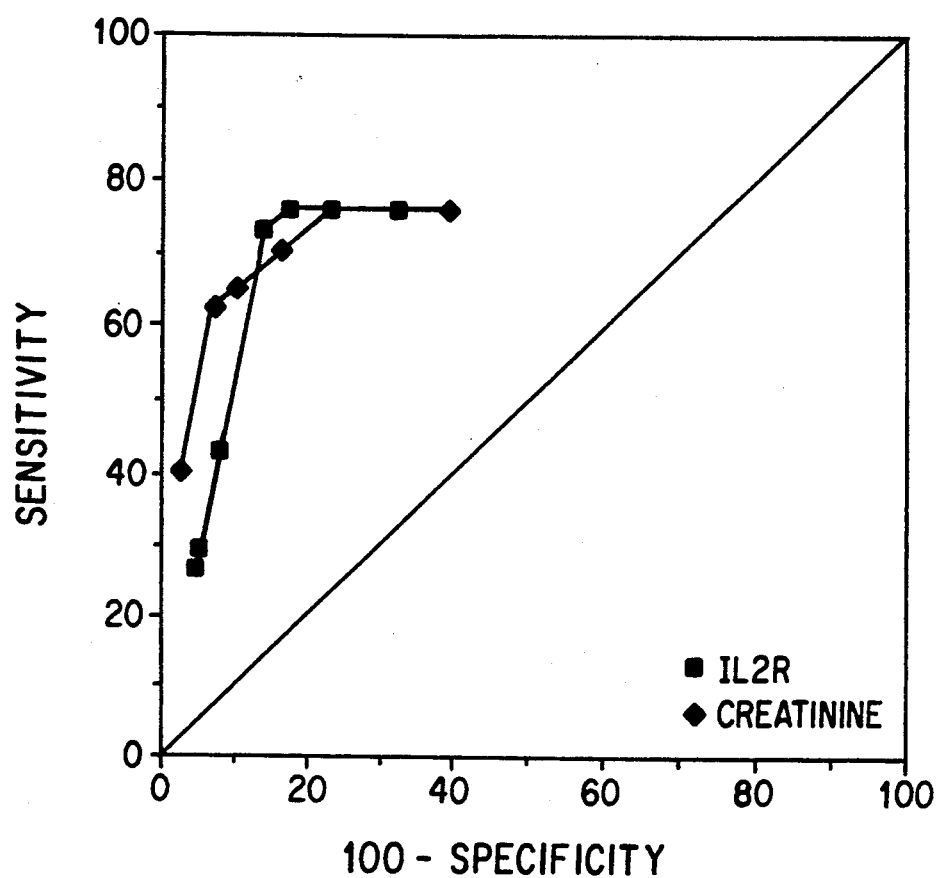

FIG. 27. A plot of the sensitivity and specificity of the serum IL2R assay and serum creatinine (Cr) for the diagnosis of rejection. The data from FIG. 26(a,c) are given in the form of receiver operating characteristic (ROC) curves. In this display, the threshold for a positive test is varied over a broad range (here from the 70th to the 99th percentile of stable patients). The further the curves are from the diagonal line (which represents chance alone), the better the discrimination of the test. The curves for IL2R and Cr are equivalent.

5. DETAILED DESCRIPTION OF THE INVENTION

The present invention is directed to the measurement of soluble T cell growth factor receptors, soluble T cell differentiation antigens, or related soluble molecules or fragments thereof, and the use of such measurements in the diagnosis and therapy of diseases and disorders.

As used herein, the term "soluble" shall mean those molecules that are "spontaneously released"; i.e., released by normal or pathologic physiological processes of the cell. Such molecules are to be distinguished from "solubilized" cell surface forms of the molecules, whose solubilization is brought about by in vitro manipulation such as cell lysis by detergent. The soluble T cell markers (antigens and receptors) of the invention are molecules which carry antigenic determinants of their cell-surface counterparts.

Proteinaceous molecules, or fragments thereof, derived from the surface of T cells, and proteinaceous molecules which have immunologically similar counterparts present on the surface of T cells or activated T cells, which are present in a body fluid and not associated with the surface of a T cell are soluble T cell surface molecules of the invention. These molecules can be either glycosylated or nonglycosylated and may be soluble by themselves or considered soluble by virtue of their association with other soluble molecules.

The measurement of the soluble molecules of the invention can be valuable in monitoring the effect of a therapeutic treatment on a subject, detecting and/or staging a disease in a subject, and in differential diagnosis of a physiological condition in a subject. These measurements can also aid in predicting therapeutic outcome and in evaluating and monitoring the immune status of patients. More than one type of soluble molecule can be measured. The soluble molecules can be measured in any body fluid of the subject including but not limited to serum, plasma, urine, and saliva.

5.1. Monitoring the Effect of a Therapeutic Treatment

The present invention provides a method for monitoring the effect of a therapeutic treatment on a subject who has undergone the therapeutic treatment. This method comprises measuring at suitable time intervals the amount of a soluble molecule or soluble fragment thereof which comprises, or is immunologically related to, a T cell growth factor receptor or T cell differentiation antigen. Any change or absence of change in the amount of the soluble molecule can be identified and correlated with the effect of the therapeutic treatment on the subject. In a specific embodiment of the invention, soluble molecules immunologically related to the interleukin-2 receptor (IL2R) can be measured in the serum of patients by a sandwich enzyme immunoassay (for an example, see Section 16, infra), in order to evaluate the therapeutic efficacy of, for example, administration of immunomodulators such as alpha-interferon, Cyclosporin A, and monoclonal antibody OKT3. In another embodiment, soluble molecules related to the interleukin-1 receptor can be measured. In yet another embodiment, soluble molecules immunologically related to the CD4 antigen can be measured. In particular, the levels of soluble CD4 molecules can be measured in the serum of AIDS patients in order to evaluate the therapeutic efficacy of treatments such as the administration of AZT, interferon, or CD4 itself.

The therapeutic treatments which may be evaluated according to the present invention include but are not limited to radiotherapy, drug administration, vaccine administration, immunosuppressive or immunoenhancive regimens, etc. The immunosuppressant regimens include, but are not limited to administration of drugs such as Cyclosporin A, chlorambucil, cyclophosphamide, or azathioprine, and anti-T cell antibody such as anti-T3 monoclonal antibody and anti-thymocyte globulin, etc. The immunoenhancive regimens include, but are not limited to administration of interleukin-1, interleukin-2, and other T cell growth factors.

5.2. Detecting and/or Staging a Disease in a Subject

In another embodiment of the present invention, measurement of a soluble molecule which comprises, or is immunologically related to, a T cell growth factor receptor or T cell differentiation antigen can be used to detect and/or stage a disease or disorder in a subject. The measured amount of the soluble molecule is compared to a baseline level. This baseline level can be the amount which is established to be normally present in the body fluid of subjects with various degrees of the disease or disorder. An amount present in the body fluid of the subject which is similar to a standard amount, established to be normally present in the body fluid of the subject during a specific stage of the disease or disorder, is indicative of the stage of the disease in the subject. The baseline level could also be the level present in the subject prior to the onset of disease or the amount present during remission of disease. Diseases or disorders which may be detected and/or staged in a subject according to the present invention include but are not limited to those listed in Table II, infra.

TABLE II

DISEASES AND DISORDERS WHICH MAY BE DETECTED AND/OR STAGED IN A SUBJECT ACCORDING TO THE PRESENT INVENTION

I. Infectious Diseases
   Induced by virus:
   Herpesvirus
   Cytomegalovirus
   Epstein-Barr Virus
   HTLV-I
   HTLV-III/LAV/HIV (AIDS)
II. Cancer
   T cell leukemia
   HTLV-I-associated adult T cell leukemia
   T cell lymphoma
   Burkitt's lymphoma
   Hairy cell leukemia
   Sezary syndrome
   Hodgkin's disease
   Chronic lymphocytic leukemia
   Non-Hodgkin's lymphoma
   B-cell acute lymphoblastic leukemia
   Solid tumors
III. Autoimmune Diseases
   Rheumatoid arthritis
   Diabetes
   Multiple sclerosis
   Systemic lupus erythematosis
IV. Organ Allograft Rejection In specific embodiments of this aspect of the invention, measurements of plasma or serum levels of the soluble IL2R or related molecules can be used in the detection of disease, or to determine disease stage and assign risk. For example, patients with lymphatic diseases and cancer such as non-Hodgkin's lymphoma, B cell acute lymphoblastic leukemia, Hodgkin's disease, or adult T cell leukemia can be monitored by measuring serum levels of soluble IL2R; elevated serum IL2R correlates directly with severity of the disease condition and indicates a poor response to therapy as well as a poor prognosis. In another example, the response of patients with non-lymphatic cancers to therapy with IL-2 can be monitored; in this case elevated serum levels of soluble IL2R indicates a positive response to IL-2 therapy. In another specific embodiment, detailed in the examples infra, measurement of soluble IL2R levels in the body fluid of a patient with hairy cell leukemia can be used to determine the extent of bone marrow infiltration. Detection of an increase in soluble IL2R levels can also be used to diagnose lung cancer in patients. Soluble IL2R measurements can also be used to stage squamous cell lung carcinoma, in which asymptomatic patients with relatively limited and moderately differentiated squamous cell carcinoma have higher levels of soluble IL2R than symptomatic patients with big tumors and advanced disease.

Responses to viral infections can also be monitored by measuring soluble IL2R levels in a patient. For example, patients infected with herpes virus or an AIDS virus present elevated serum levels of soluble IL2R. In another embodiment, plasma, serum, or urine IL2R levels can be measured in transplant patients; elevated levels of soluble IL2R is a diagnostic indication of allograft rejection.

In another specific embodiment, T cell CD8-like molecules may be measured; detection of increased levels of soluble CD8 (T8) antigen is associated with various diseases and disorders such as rheumatoid arthritis and infectious diseases such as EBV-induced mononucleosis. Detection of elevated levels of a CD8-like antigen can indicate the involvement of significant numbers of suppressor/cytotoxic T cells with a specific pathological event, distinct from immune activation as measured by a rise in cell-free IL2R. Soluble CD8 antigen can also be used in staging Hodgkin's disease, and in monitoring therapeutic efficacy.

In another embodiment of the invention, detection of an increase in soluble CD4 antigen in the body fluid of a patient can be used to diagnose a state of immune activation. Soluble CD4 measurements can also be used to detect and/or stage adult T cell leukemia. Elevation of CD4 antigen levels in the synovial fluid of a patient can indicate rheumatoid arthritis. In another embodiment, elevated levels of soluble CD4 in synovial fluid relative to serum is a diagnostic indication of rheumatoid arthritis. In yet another embodiment, the detection of soluble CD4 in cell culture supernatants can be relied on as an indication of the CD4+ phenotype of the lymphocytes present.

5.3. Differential Diagnosis of a Physiological Condition

In another embodiment of the invention, the measurement of soluble T cell growth factor receptors, T cell surface antigens, or immunologically related molecules can be used to differentially diagnose in a subject a particular physiological condition as distinct from among two or more physiological conditions. To this end, the measured amount of the soluble molecule is compared with the amount of the soluble molecule normally present in a body fluid of a subject with one of the suspected physiological conditions. A measured amount of the soluble molecule similar to to the amount normally present in a subject with one of the physiological conditions, and not normally present in a subject with one or more of the other physiological conditions, is indicative of the physiological condition of the subject.

In a specific embodiment of this aspect of the invention, measurement of soluble molecules can be used in the differential diagnosis of renal allograft rejection, especially in distinguishing Cyclosporin A nephrotoxicity or infection. Similar differential diagnosis of allograft rejection using the methods of the invention can be applied to other organ allografts, including but not limited to liver, heart, and pancreas. In a preferred embodiment, the measurement of changes in the levels of soluble molecules, as compared to the measurement of the absolute levels of the soluble markers, can be used to differentially diagnose renal allograft rejection. In a particular embodiment of this aspect of the invention, the soluble molecules can be IL2R or related molecules. In another particular embodiment of the invention, increases in both soluble IL2R and creatinine levels in a body fluid of a transplant patient can be used to differentially diagnose renal allograft rejection over infection.

In another specific embodiment, measurements of serum CD8 levels may be used in the differential diagnosis of rheumatoid arthritis, as distinguished from other joint diseases.

In yet another specific embodiment of the invention, lymphocytic leukemia may be differentially diagnosed, as distinguished from other leukemia, by measurement and detection of IL2R.

5.4. Soluble T Cell Growth Factor Receptors, T Cell Differentiation Antigens, and Related Molecules Any T cell surface molecule or immunologically related molecule which is present in soluble form in the body fluid at levels which correlate with a disease condition or disorder, or a stage thereof, may be used in the practice of the present invention. T cell surface markers which may potentially be used include but are not limited to those listed in Table I, supra.

In specific embodiments, the soluble form of the CD4 and/or CD8 cell surface molecules may be measured.

Other T cell surface molecules whose soluble forms may be measured in accordance with the present invention include but are not limited to T cell growth factor receptors or binding proteins, e.g. interleukin-2 receptor and interleukin-1 receptor or binding protein. In specific embodiments, serum IL2R measurements can be used to predict therapeutic outcomes and monitor the immune status of patients with cancer, immunodeficiencies, autoimmune diseases, or allograft rejection.

5.4.1. Kits and Assays for Measurement

Any procedures known in the art for the measurement of soluble molecules can be used in the practice of the instant invention. Such procedures include but are not limited to competitive and non-competitive assay systems using techniques such as radioimmunoassays, ELISA (enzyme linked immunosorbent assay), "sandwich" immunoassays, precipitin reactions, gel diffusion precipitin reactions, immunodiffusion assays, agglutination assays, complement-fixation assays, immunoradiometric assays, fluorescent immunoassays, protein A immunoassays, and immunoelectro-phoresis assays, to name but a few.

In a preferred embodiment, a sandwich enzyme immunoassay can be used. One description of such an embodiment follows: A monoclonal antibody (capture antibody, mAb 1) directed against the soluble antigen is adsorbed onto a solid substratum. The soluble antigen present in the sample binds to the antibody, and unreacted sample components are removed by washing. An enzyme-conjugated monoclonal antibody (detection antibody, mAb 2) directed against a second epitope of the antigen binds to the antigen captured by mAb 1 and completes the sandwich. After removal of unbound mAb 2 by washing, a substrate solution is added to the wells. A colored product is formed in proportion to the amount of antigen present in the sample. The reaction is terminated by addition of stop solution and absorbance is measured spectrophotometrically. A standard curve is prepared from known concentrations of the soluble antigen, from which unknown sample values can be determined. In particular embodiments, such an assay may be used to determine soluble IL2R levels or soluble T cell antigen levels. In a preferred embodiment for the measurement of IL2R levels, anti-IL2R mAbs 2R12 and 7G7 can be used as the capture and detection antibodies, respectively, in a sandwich immunoassay (such as the CELLFREE® assay described in Section 16 infra). In a preferred embodiment for the measurement of soluble CD8 antigen levels, anti-CD8 mAbs 4C9 and 5F4 can be used as the capture and detection antibodies, respectively, in a sandwich enzyme immunoassay (such as described in Section 29, infra). In a preferred embodiment for the measurement of soluble CD4 antigen levels, anti-CD4 mAbs 8F4 and R2B7 can be used as the capture and detection reagents, respectively, in a sandwich enzyme immunoassay (see Sections 5.4.3 and 23, infra).

Kits for carrying out the assays of and used in the practice of the present invention are also within the scope of the invention. For instance, such a kit can comprise a pair of antibodies to the same T cell marker (receptor or antigen) which do not compete for the same binding site on the marker. In another embodiment, a kit can comprise more than one pair of such antibodies, each pair directed against a different T cell marker, thus useful for the detection or measurement of a plurality of T cell markers.

5.4.2. Formulation of an Immunoassay for the Preferential Detection of Soluble Forms of T Cell Surface Markers Over Solubilized Forms The present invention also provides a way of deriving immunoassay systems which preferentially detect/quantitate physiologically released (soluble) forms of cell surface markers over solubilized (e.g., detergent-treated) cell surface markers. Such a method involves the use of recombinant forms of the specific cell surface marker to be assayed, which have been genetically engineered to be physiologically soluble (i.e., by deletion of DNA sequences encoding the transmembrane region). Such recombinant forms are likely to lack epitopes found on the transmembrane region, which epitopes are thus specific to the solubilized cell surface marker and which epitopes are likely also to be absent from the physiologically released form of the marker. Thus, the recombinant molecule can be used to screen anti-cell surface marker antibodies for determination of the appropriate antibodies to be used for preferential detection of the physiologically released form of the surface marker. Pairs of antibodies can be screened for optimization of a sandwich ELISA for detection of soluble cell-surface marker. This aspect of the invention is illustrated by way of example in Section 23, infra, where a soluble CD4 assay is devised that preferentially detects soluble CD4 relative to solubilized CD4.

Antibodies can be produced for testing for suitability for use in the detection of soluble forms of T cell surface markers. Such antibodies can be polyclonal or monoclonal. Monoclonal antibodies are preferred for use.

Various procedures known in the art may be used for the production of polyclonal antibodies to epitopes of a given T cell surface molecule. For the production of antibody, various host animals can be immunized by injection with a T cell surface molecule, a recombinant version thereof, synthetic protein, or fragment thereof, including but not limited to rabbits, mice, rats, etc. In a preferred embodiment, the immunogen is a truncated recombinant soluble form of the T cell surface molecule. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

A monoclonal antibody to an epitope of the T cell surface molecule can be prepared by using any technique which provides for the production of antibody molecules by continuous cell lines in culture. These include but are not limited to the hybridoma technique originally described by Kohler and Milstein (1975, *Nature* 256:495-497), and the more recent human B cell hybridoma technique (Kozbor et al., 1983, *Immunology Today* 4:72) and EBV-hybridoma technique (Cole et al., 1985, *Monoclonal Antibodies and Cancer Therapy*, Alan R. Liss, Inc., pp. 77-96).

In one embodiment, the monoclonal antibodies may be human monoclonal antibodies or chimeric human-mouse (or other species) monoclonal antibodies. Human monoclonal antibodies may be made by any of numerous techniques known in the art (e.g , Teng et al., 1983, *Proc. Natl. Acad. Sci. U.S.A.* 80:7308-7312; Kozbor et al., 1983, *Immunology Today* 4:72-79; Olsson et al., 1982, *Meth. Enzymol.* 92:3-16). Chimeric antibody molecules may be prepared containing a mouse (or rat, or other species) antigen-binding domain with human constant regions (Morrison et al., 1984, *Proc. Natl. Acad. Sci. U.S.A.* 81:6851; Takeda et al., 1985, *Nature* 314:452).

A molecular clone of an antibody to an epitope of a T cell surface molecule can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

Antibody molecules may be purified by known techniques, e.g., immunoabsorption or immunoaffinity chromatography, chromatographic methods such as HPLC (high performance liquid chromatography), or a combination thereof, etc.

Antibody fragments which contain the idiotype of the molecule can be generated by known techniques. For example, such fragments include but are not limited to: the F(ab')₂ fragment which can be produced by pepsin digestion of the antibody molecule; the Fab' fragments which can be generated by reducing the disulfide bridges of the F(ab')₂ fragment, and the Fab fragments which can be generated by treating the antibody molecule with papain and a reducing agent.

Once specific antibodies are demonstrated to be suitable for use in the preferential detection of soluble T cell-surface molecules, other such suitable antibodies may be selected by virtue of their having the same epitope specificity as the former antibodies. Such similar epitope specificity can be ascertained, for example, by observing the ability of a second antibody to inhibit binding of a first antibody to its antigen.

5.4.3. Soluble CD4 and Assay for Its Detection

The invention is also directed to assays for measurement of soluble (released) CD4, which assays preferentially measure soluble CD4 over the solubilized membrane form of CD4. Examples of such assays are detailed infra in Section 23.

In a preferred embodiment for the detection or measurement of soluble CD4 antigen levels, anti-CD4 mAbs 8F4 and R2B7 can be used as the capture and detection reagents, respectively, in a sandwich immunoassay.

We also demonstrate infra that the physiologically released form of CD4 is physically different from that of the solubilized cell surface form, and that assays which quantitate the solubilized cell surface form do not necessarily quantitate the released form.

Soluble CD4 has been specifically quantitated, according to the present invention, and has been shown to be a reliable indicator of various pathologic conditions (see Section 23, infra). Thus, detection and/or measurement of soluble CD4 can be used to diagnose, to monitor, and/or to stage various diseases and disorders involving the immune system.

5.4.4. Detecting or Staging of Disease or Monitoring of Response to Treatment in Patients by Measurement of a Plurality of Soluble T Cell Surface Markers The present invention also provides for the detecting or staging of disease, or the monitoring of treatment by measuring a plurality (at least two) T cell surface markers (receptors or differentiation antigens). For example, a plurality of soluble T cell markers selected from among soluble IL2R, CD4, and CD8 can be measured to diagnose, stage, or monitor treatment of diseases or disorders. Such diseases or disorders include those discussed supra in Sections 5.1 through 5.3 (e.g., see Table II). Soluble marker levels can represent a measure of immune system function, paralleling disease course or treatment efficacy. In a preferred embodiment, the prognostic indicator is the observed change in different marker levels relative to one another, rather than the absolute levels of the soluble markers present at any one time. Since soluble CD4, soluble CD8 and soluble IL2R levels are measures of the immune system itself, they should provide a much improved measure of the relative health of the immune system during various stages of diseases or disorders.

In a preferred embodiment, measurements of a plurality of soluble T cell surface markers are used to detect, stage, or monitor treatment of diseases and disorders caused by HIV (the causative agent of AIDS) infection. Since the discovery of AIDS and the observation that the AIDS virus, HIV, binds to the T4, or CD4, receptor, there have been several proposals for the treatment of AIDS patients or for the development of vaccines for populations of people at risk. These include the treatment of AIDS patients with drugs such as AZT (azidodeoxythymidine), γ or β interferons, and with soluble CD4, or its fragments and derivatives, and the production of potential AIDS vaccines, such as gp120 peptides. What is very much needed is a procedure that can be used to monitor the efficacy of these treatments or vaccines. To date, the levels of the HIV antigen p24 have not proved sensitive enough. With the observation herein described that soluble CD4 in particular, but soluble CD8 and soluble IL2R receptors as well, can be identified and detected in HIV-infected patients with different manifestations of disease, it becomes possible to develop a sensitive immunoassay to monitor AIDS therapies and vaccines. The CELLFREE ® Test Kit (T Cell Sciences, Cambridge, Mass.) assays can be useful for this purpose. Due to the intimate involvement of CD4 in the etiology of AIDS, it is expected that spontaneously released soluble CD4 levels should be extremely sensitive markers of the state of immune function during various stages of HIV infection and therapeutic treatments. This is especially true, as soluble CD4 is produced when CD4+ cells become activated, (see Section 23.2, infra) as occurs during HIV infection. Furthermore, measurements of other soluble T cell markers, such as soluble IL2R and soluble CD8, that also indicate the state of immune function should be valuable.

The best index for monitoring AIDS treatment or disease progression can be a profile of soluble T cell markers, such as soluble CD4, CD8 and IL2R, rather than any individual marker alone (see Sections 13.3 and Section 26). Such a profile can be obtained by determining the soluble receptor levels of a panel of soluble receptors in longitudinal samples of sera from patients undergoing treatment.

In a preferred aspect, the approach that can be taken is to determine the levels of soluble CD4 (and soluble CD8 and soluble IL2R) levels in longitudinal time studies and to compare these values with a baseline level. The baseline level can be either the level of the soluble marker present in normal, disease free individuals; and/or the levels present prior to treatment, or during remission of disease, or during periods of stability. These levels can then be correlated with the disease course or treatment outcome.

6. Soluble IL2R Detection in Patients

The examples described in Sections 7 through 15 infra demonstrate the detection of soluble or cell free IL2R i patients and the utility of such detection for staging various diseases or conditions. The results indicate that: (a) serum IL2R levels are elevated in patients with active lymphatic diseases such as leukemia and lymphoma. In such patients, serum IL2R levels bear a direct relationship with severity of disease and poor prognosis. (b) Serum IL2R levels are generally not elevated in patients with non-lymphatic cancers; however, IL-2 patients receiving IL-2 therapy who are responding to such therapy demonstrate elevated levels of serum IL2R. (c) Serum IL2R levels are elevated in transplant patients who reject allografts; however, serum IL2R levels are not elevated in patients who experience toxicity caused by immunosuppressive drugs used in transplant patients but do not demonstrate true allograft rejection.

The procedures used in these examples are described in the subsections below.

6.1. Monoclonal Antibodies

Monoclonal antibodies directed against the IL2R were produced as previously described (Uchiyama, T., et al., 1981, *J. Immunol.* 126(4) 1393-1397; Rubin, L. A., et al., 1985, *Hybridoma* 4:91-102; Jung, L. K. L., et al., 1984, *J. Exp. Med.* 160:1957). Additionally, monoclonal antibodies directed against IL2R may be purchased commercially (Becton-Dickenson, California; Coulter Diagnostic, Florida). Although the published monoclonal antibodies (Uchiyama, supra; Rubin, supra; Jung, supra) each recognize IL2R, each of these monoclonal antibodies recognizes a different epitope. Monoclonal antibodies were purified according to established standard methods (Cortheir, G., et al., 1984, *J. Immuno. Method* 66:75-79). Horseradish peroxidase conjugation was done according to published procedures (Wilson, M. B. and Nakane, P. K., 1978, "Recent Developments in the Periodate Method of Conjugating Horseradish Peroxide (HRPO) to Antibodies", in *Immunofluorescence and Related Staining Techniques*, Knapp, W. K. Holubar, and G. Wick, eds., Elsevier/North-Holland Biomedical Press, pp. 215-224).

6.2. Soluble IL2R Assay

In the examples described in Sections 7 through 15, either the procedure described below or the CELL-FREE® Interleukin-2 Receptor Test Kit (T-Cell Sciences, Inc., Cambridge, Mass.) described in Section 16 infra was used to measure the amount of soluble IL2R in clinical samples. In each of these assay procedures, two monoclonal antibodies, each recognizing a different epitope on the target antigen, was used.

6.2.1. Procedure

Soluble IL2R was detected in samples using the procedure outlined below:
(a) Polystyrene microliter wells (Flow Laboratory) were coated overnight at room temperature with 100 μl of an anti-IL2R murine monoclonal antibody (2 ug/ml) in phosphate buffered saline (PBS).
(b) Coating solution was discarded and wells were blocked for 1-2 hours at room temperature with 300 μl of 1% bovine serum albumin (BSA) in Tris-buffered saline containing 25 mM Tris pH 7.4 in 0.05% of Tween 20 and 0.15pl M sodium chloride (Tris-Tween buffer).
(c) Wells were washed 3 times with Tris-Tween buffer.
(d) 50 μl sample was added per well, followed by 100 μl diluent containing fetal calf serum (FCS) in Tris-Tween buffer. Wells were incubated 2 hours at 37° C.
(e) Wells were washed 3 times with Tris-Tween buffer.
(f) 100 μl of horseradish peroxidase (Sigma Chemical Co.) conjugated anti-IL2R monoclonal antibody in PBS containing 50% FCS was added per well. Wells were incubated 2 hours at 37° C.
(g) Wells were washed 4 times with Tris-Tween buffer.
(h) 100 μl of 0.2% o-phenylenediamine (OPD) and 0.015% of $H_2O_2$ in 17 mM citric acid, 65 mM dibasic sodium phosphate (citrate-phosphate buffer) was added per well. Plates were incubated for 30 minutes at room temperature.
(i) 50 μl of 2N $H_2SO_4$ was added to each well and the absorbance of each well was measured at 490 nm in a microtiter plate reader (Dynatech MR600, Dynatech Corp., Alexandria, Va.).

6.2.2. IL2R Control Standards

The results of the immunoassay were expressed in units based on a supernatant standard defined as 1000 units/ml. The supernatant culture fluid was generated according to the following procedure:
(a) Mononuclear white blood cells were isolated from 500 ml of whole blood using the Ficoll-Hypaque procedure as outlined in the manufacturing package insert (Sigma Chemical Co.).
(b) Approximately $1 \times 10^6$ cells/ml of white blood cells were suspended in RPMI-1640 medium containing 10% FCS and 100 units of penicillin-streptomycin (Flow Laboratory).
(c) 2 μg/ml of phytohemagglutinin (PHA—Wellcome Diagnostics) were added to the culture.
(d) After 3-6 days of culture, the supernatant was harvested after removing the cells by centrifugation at $200 \times g$.

(e) Supernatant was saved and assigned a reference value of 1000 units/ml.

6.2.3. Flow Cytometric Method

Flow cytometric analysis of peripheral blood lymphocytes and tissue culture cells was performed as described previously (Hoffman, R. A., et al., 1980, Proc. Natl. Acad. Sci. U.S.A. 77:4914–4917).

7. THERE IS NO CORRELATION BETWEEN SOLUBLE IL2R LEVEL AND IL2R BEARING LYMPHOCYTES IN VIVO

As shown in FIG. 1A and 1B, the level of serum (soluble) IL2R and the number of T lymphocytes bearing cell surface IL2R correlated well, in a phytohemagglutinin (PHA) stimulated human peripheral blood T cell culture in vitro. However, in vivo, the number of IL2R bearing T cells in circulation correlated poorly with the level of serum IL2R (FIG. 2). Therefore, it is not possible to determine from in vitro experimentation whether serum level of a soluble T cell marker will correlate with an in vivo observation. The clinical use of serum T cell markers can only be determined from direct patient studies.

The level of soluble IL2R has been found to be elevated in a broad spectrum of diseases (Table III).

TABLE III

SERUM LEVEL OF SOLUBLE IL-2 RECEPTOR IN PATIENTS

| | Average Value IL-2 Receptor (units/ml) | Number of Samples Tested |
|---|---|---|
| Healthy Control | 250 | >50 |
| AIDS Related | 960 | 41 |
| Herpes Virus Infection | >1500 | 9 |
| Other Infections | 1000 | 5 |
| Systemic Lupus Erythematosis | 620 | 50 |
| Rheumatoid Arthritis | 500 | 20 |

Specific clinical applications of such measurements are outlined in the examples detailed in the Sections which follow.

8 SERUM MEASUREMENT OF SOLUBLE IL2R MAY BE USED FOR STAGING LEUKEMIA OR MONITORING A THERAPEUTIC TREATMENT

Human T cell leukemia virus (human T lymphotropic virus) Type I (HTLV-I), a sub-group of human T cell leukemia/lymphoma virus, has been closely linked to human adult T cell leukemia (ATL). Identification of HTLV-I as a possible etiological agent of ATL has permitted the development of an assay system for the detection of an antibody directed against the virus in the sera of patients (Saxinger, C. and Gallo, R. C., 1983, Lab. Invest. 49:371–377). Antibody to HTLV-I has been found in virtually all ATL patients. However, HTLV-I seropositive healthy individuals without evidence of ATL are common in ATL epidemic areas of Japan. The differentiation of active leukemia patients from asymptomatic individuals has important diagnostic and prognostic value. Currently no reliable serum test is available for the staging of active versus inactive disease.

Impairment of the host immunosurveillance system is known to influence the development of various cancers in humans and animals. The serum level of IL2R-related macromolecules provides an important distinction of various disease stages in patients. The serum levels of IL2R were measured in patients exhibiting different stages of leukemia using the assay described in Section 6.2. As shown in Table IV below, patients with active T cell malignancy present an elevated level of soluble IL2R as compared to healthy normal and HTLV-I seropositive healthy individuals. Similarly, T cell malignancy patients who are in remission have a decreased level of soluble IL2R.

TABLE IV

SERUM LEVEL OF SOLUBLE IL-2 RECEPTOR IN LEUKEMIA PATIENTS

| Stage of Leukemia | Soluble IL-2 Receptor (units/ml) | Number of Patients |
|---|---|---|
| Active ATL (Japan) | 1765 | 3 |
| Active T Cell Leukemia (U.S.) | 1050 | 7 |
| Seropositive healthy patients | 230 | 17 |
| Leukemia patients in remission | 230 | 4 |

FIG. 3 shows that the amount of IL2R in serum parallels the clinical condition of lymphatic cancer patients. Elevated levels of IL2R in serum indicate failure of therapeutic treatment. After effective treatment, the serum level of IL2R returns to a normal range.

9. HIGH SERUM IL2R LEVELS ARE RELATED TO ADVANCED DISEASE AND A POOR OUTCOME IN CHILDHOOD NON-HODGKIN'S LYMPHOMA

The results presented in the subsection below demonstrate that elevated levels of serum IL2R as measured by the CELLFREE® assay (Section 16) correlate directly with advanced stages of childhood non-Hodgkins lymphoma and indicate a poor response to the chemotherapeutic regimen selected as well as a poor prognosis.

9.1. Patients and Methods

9.1.1. Patients

From 1979 to 1986, 99 consecutive children with non-Hodgkin's lymphoma (NHL) or B-cell acute lymphoblastic leukemia (ALL) were admitted to three clinical trials (Link, M., et al., 1984, Proc. Am. Soc. Clin. Oncol. 3:251; Murphy, S. B., et al., 1986, J. Clin. Oncol. 4:1732–1739; Dahl, G. V., et al., 1985, Blood 66:1110–1114) at St. Jude's Research Hospital, depending on the histologic features and stage of their disease. Serum samples taken before the start of chemotherapy were available for 65 of these patients. The 41 boys and 18 girls with NHL ranged in age from 1.8 to 17.9 years (median, 10.7 years). The 3 boys and 3 girls with B-cell ALL were 2.3 to 10.2 years old (median, 5.8 years). In each case the diagnosis was based on a combination of clinical, anatomic, histologic, cytologic criteria, with addition of immunologic and cytogenetic studies in some instances. The Working Formulation (National Cancer Institute Sponsored Study of Classifications of Non-Hodgkin's Lymphoma: Summary and Description of a Working Formulation for Clinical Usage. The Non-Hodgkin's Lymphoma Pathologic Classification Project, 1982, Cancer 49: 2112–35) was used to classify cases into diffuse small noncleaved-cell, lymphoblastic, or large cell (noncleaved, cleaved and immunoblastic) types. The first category encompasses not only Burkitt's tumor but also lymphomas that have been designated as undifferentiated non-Burkitt's type. The diagnosis of B-cell ALL was made from the presence of surface immunoglobulins on bone marrow blast cells with L3 morphology according to French-American-British (FAB) criteria (Bennett, J. M., et al., 1976, *Br. J. Haematol.* 33:451-458)

A stage was assigned to each case of NHL with the use of a previously described system (Murphy, S. B., 1980, *Semin. Oncol.* 7:332-339). Children with localized NHL in favorable sites have stage I or II disease. Stage III includes disseminated disease on both sides of the diaphragm, extensive unresectable intraabdominal disease and all primary epidural or anterior mediastinal tumors without bone marrow or central nervous system (CNS) involvement. Stage IV is defined by initial CNS and (or) bone marrow involvement (less than or equal to 25% blast cells) in addition to other tumor sites. Cases with greater than 25% malignant B cells in the bone marrow were classified as B-cell ALL, representing advanced B-cell NHL in a phase of leukemic evolution. In this study, 30 patients had diffuse small non-cleaved-cell NHL (stage I in 8, II in 10, III in 11 and IV in one); 22 had lymphoblastic NHL (stage I in 1, II in 2, III in 14 and IV in 5); 7 had large cell NHL (stage I in 3 and II in 4) and 6 had B-cell ALL.

Soluble IL2R was also measured in 12 children with otitis media who were otherwise normal and ranged in age from 1 to 6 years (median, 3 years).

9.1.2. Treatment

Children with stage I or II NHL were treated according to a Pediatric Oncology Group (POG) protocol that employs three cycles of cyclophosphamide, doxorubicin, vincristine and prednisone for remission induction and consolidation therapy and 6 months of 6-mercaptopurine and methotrexate for continuation therapy (Link, M., et al., 1984, *Proc. Am. Soc. Clin. Oncol.* 3:251). Children with stage III or IV small noncleaved-cell NHL or B-cell ALL received 6 months of intensive treatment with alternating courses of either high-dose fractionated cyclophosphamide followed by vincristine and doxorubicin or coordinated high-dose methotrexate and cytarabine (Murphy, S. B., et al., 1986, *J. Clin. Oncol.* 4:1732-1739). Patients with stage III or IV lymphoblastic NHL were treated on a protocol designed for high-risk ALL in which teniposide plus cytarabine was added to an otherwise conventional regimen of therapy (Dahl, G. V., et al., 1985, *Blood* 66:1110-1114). Informed consent was obtained for all patients, and the investigation was approved by the institution's clinical trials committee.

9.1.3. Determination of Soluble IL2R Levels

Soluble IL2R was measured using as the CELL-FREE® Interleukin-2 Receptor Test Kit (T-cell Science, Inc., Cambridge, Mass.) described in Section 16 infra. Serum levels of IL2R are expressed in units (U)/ml. A reference preparation of 1000 U/ml of supernatant from phytohemagglutinin-stimulated peripheral blood lymphocytes was used as a standard. The normal serum IL2R values in healthy adult donors ranges from 50 to 500 U/ml (mean, 260 U/ml).

9.1.4. Determination of Serum Lactic Dehydrogenase

The total activity of serum lactic dehydrogenase (LDH) was measured with the Monitor Kinetic AMB-610 assay on the KDA analyzer (American Monitor Corp., Indianapolis, Ind.). Samples with enzyme activities greater than 700 U/L were diluted and reassayed; the values obtained were then multiplied by the dilution factor. The normal values for our laboratory range from 30 to 300 U/L.

9.1.5. Statistical Analysis

The Kruskal-Wallis test was used to compare soluble IL2R or serum LDH levels among different subgroups of patients with NHL. The Pearson product-moment correlation (r) and t-test analysis were used to determine the association between soluble IL2R and serum LDH levels. Time-to-failure curves were constructed by the Kaplan-Meier procedure (Kaplan, E. L. and Meier, P., 1958, *J. Am. Stat. Assoc.* 53:457-481), with differences analyzed by the log rank test (Peto, R. and Peto, J., 1972, *J. R. Stat. Soc.* 135A:185-216). Time to failure was defined as the interval between achievement of remission and relapse or death due to any cause. Patients who did not enter remission were assigned a failure time of zero. The influence of potentially significant prognostic factors on time to failure was estimated with the Cox proportional-hazards model (Cox, D. R., 1972, *J. R. Stat. Soc. B.* 34:187-220), which permits comparison of treatment outcome for two or more subsets of patients while simultaneously adjusting for the effect of other factors (covariates) in the model. Final selection of factors for the model depended on whether or not the P value was less than 0.10 after adjustment for other variables already in the model, using a forward stepwise procedure. An IL2R value of 1000 U/ml was chosen as the dividing point between high and low receptor levels because it coincided well with clinically distinct groups of diseases and treatment outcome.

9.2. Results

The most reliable prognostic factors in childhood NHL have been the stage of disease at diagnosis and serum LDH level (Murphy, S. B., et al., 1986, *J. Clin. Oncol.* 4:1732-1739; Murphy, S. B., 1980, *Semin. Oncol.* 7:332-339; Arseneau, J. C., et al., 1975, *Am. J. Med.* 58:314-321; Magrath, I. T., et al., 1984, *Blood* 63:1102-1111). We report here that high soluble IL2R levels predict a poor treatment outcome even after adjustment for these two factors.

9.2.1. Soluble IL2R Levels Show a Clear Relationship to Disease Stage

All patients had detectable soluble IL2R levels (FIG. 4), including the 12 children with otitis media (404 to 942 U/ml; median 615 U/ml). The highest values were found in sera from patients With B-cell ALL, 1030-17725 U/ml (median, 3283 U/ml). Children with stage III or IV small noncleaved-cell NHL had soluble IL2R levels of 329 to 5335 U/ml (median, 1832 U/ml), significantly higher than the 376 to 3390 U/ml (median, 808 U/ml) for patients with stage III or IV lymphoblastic NHL (p=0.02). The latter concentrations were in turn greater than those found in stage I or II NHL, 100 to 1143 U/ml (median, 477 U/ml) (p=0.001). Only 1 of the 28 subjects with low-stage disease had a soluble IL2R level above 1000 U/ml.

9.2.2. Soluble IL2R Levels Show a Linear Relationship with Serum LDH Levels Serum LDH level is a reliable indicator of the total body burden of malignant cells in both ALL (Pui, C.-H., et al., 1985, *Blood* 66:778-782) and NHL (Murphy, S. B., et al., 1986, *J. Clin. Oncol.* 4:1732-1739; Arseneau, J. C., et al., 1975, *Am. J. Med.* 58:314-321; Magrath, I. T., et al., 1984, *Blood* 63:1102-1111). The distribution of serum LDH levels among the various subgroups of patients showed the same pattern as was noted for IL2R: B-cell ALL is greater than stage III–IV diffuse small noncleaved-cell NHL is greater than stage III–IV lymphoblastic NHL is greater than stage I–II NHL. There was a strong positive correlation between serum IL2R and LDH levels in this study (FIG. 5).

Figure 6A:
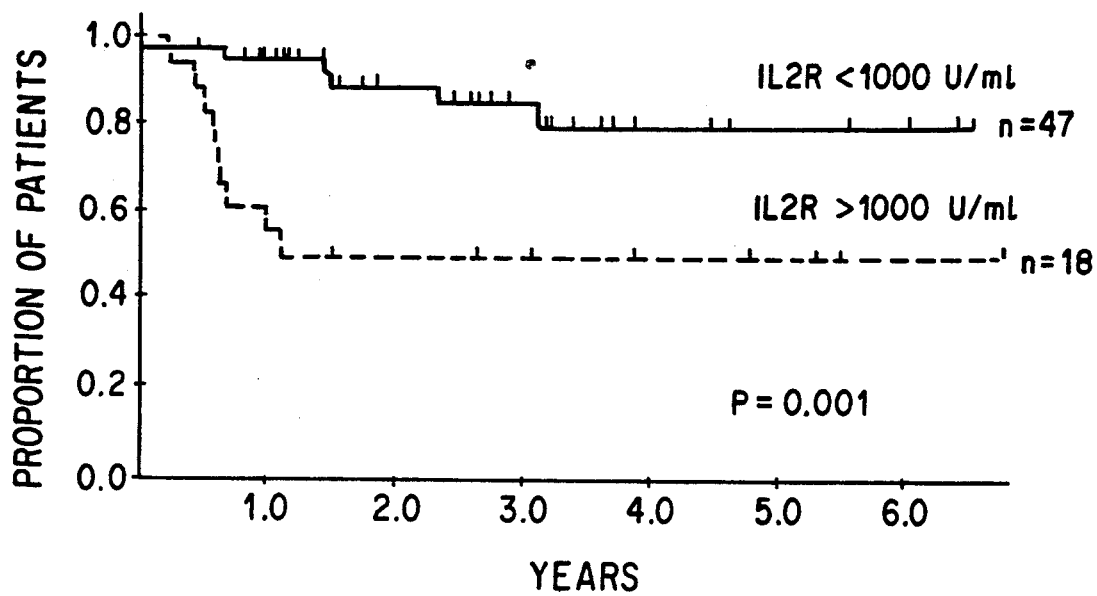
Figure 6B:
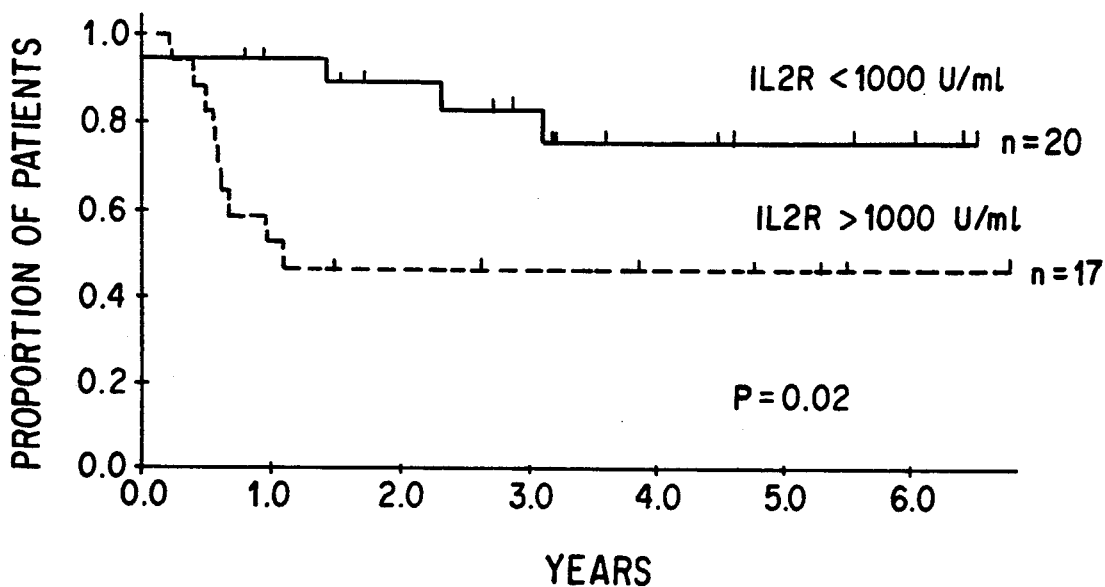

9.2.3. Higher Soluble IL2R Levels are Associated with a Poorer Treatment Outcome Higher soluble IL2R levels were associated with a poorer treatment outcome. Nine of 18 patients with levels above 1000 U/ml, compared to only 6 of 47 with lower levels, have failed therapy (FIG. 6A, p=0.001). Even when patients with stage I or II disease were excluded, high levels of soluble IL2R were still associated with a poor outcome (FIG. 6B, p=0.02). Because of the possible interrelationships among clinical and biologic risk factors in our patients, a Cox regression analysis was used to assess the relative importance of each factor after adjustment for the effects of other covariates. As shown in Table V, both soluble IL2R level and serum LDH level were found to have independent prognostic value.

TABLE V
RELATIONSHIP OF SERUM IL2R LEVEL AND OTHER PRESENTING FEATURES TO TIME TO FAILURE IN 65 CHILDREN WITH NHL OR B-CELL ALL

| Feature | Category Better | Category Worse | P Value[a] |
|---|---|---|---|
| Univariate analysis[b] | | | |
| IL2R level (U/ml) | <1000 | >1000 | 0.004 |
| LDH level (U/L) | <300 | >300 | 0.007 |
| Stage | I, II | III, IV or B-ALL | 0.017 |
| Histologic type | Lymphoblastic | Diffuse small non-cleaved cell | 0.65 |
| Multivariate model[c] | | | |
| IL2R level (U/ml) | <1000 | >1000 | 0.004 |
| LDH level (U/L) | <300 | >300 | 0.065 |
| Stage | I, II | III, IV or B-ALL | 0.62 |
| Histologic type | Lymphoblastic | Diffuse small non-cleaved cell | 0.48 |

[a]From the likelihood ratio test.
[b]Comparison of time to failure, with use of the Cox proportional-hazards model, between patients with the better-vs.-worse risk feature in the indicated category, without adjustment for the effects of other variables.
[c]As above, except that stepwise regression analysis was used to identify the best predictors of treatment outcome, taking into account the competing effects of all covariates entered in the Cox model.

The increased serum IL2R levels in our patients could reflect greater release of the receptor from either malignant cells or activated normal lymphocytes. We favor the first explanation because soluble IL2R levels not only correlated with disease stage but also showed a linear relationship with serum LDH levels, a reliable indicator of tumor cell burden.

We conclude that the level of soluble IL2R in children with NHL has independent prognostic significance, higher levels being associated with more advanced disease, greater tumor burden and a poorer outcome.

Serum CD8 Antigen and Interleukin-2 Receptor Levels in Childhood Hodgkin's Disease We determined pre-treatment serum levels of soluble CD8 antigen and soluble IL2R in 90 children with newly diagnosed Hodgkin's disease. Our results (Table VI) demonstrate that measurements of soluble CD8 antigen or IL2R can be used in the staging of Hodgkin's disease, that an increase in both soluble CD8 and IL2R is predictive of treatment failure, and that soluble CD8 levels can be relied on for monitoring treatment outcome.

TABLE VI
LEVELS OF SOLUBLE CD8 AND SOLUBLE IL2R IN SERA OF CHILDREN WITH HODGKIN'S DISEASE

| Disease Characteristics | Soluble CD8 (U/ml) | Soluble IL2R (U/ml) |
|---|---|---|
| Stage I or II | 477 | 1098 |
| Stage III or IV | 675 | 3195 |
| | p = 0.003 | p = 0.0001 |
| B symptoms | 622 | 3262 |
| All others | 494 | 999 |
| | p = 0.005 | p = 0.0001 |
| Mixed cellularity | 847 | |
| Nodular sclerosis | 509 | |
| | p = 0.005 | |

In patients with stage II or IV disease, the median serum CD8 levels were significantly higher than in those with stage I or II disease: 675 vs. 477 U/ml, p=0.003. It was also higher in children with B symptoms compared to all others: 622 vs. 494 U/ml, p=0.005. Cases of mixed cellularity had significantly higher median levels of the antigen than did those of nodular sclerosis: 847 vs. 509 U/ml, p=0.005.

Similarly, the median IL2R level was significantly higher in patients with stage III or IV disease than in those with lower stages: 3195 vs. 1098 U/ml, p=0.0001. The median IL2R level for children with B symptoms was 3262 U/ml, compared with 999 U/ml for those lacking constitutional symptoms (p=0.0001). There was, however, only a moderate correlation between serum CD8 antigen and IL2R levels (r=0.47).

Increased probability of treatment failure was significantly associated with higher serum CD8 levels (>430 U/ml) (p=0.02) and with higher serum IL2R levels (>5000 U/ml) (p=0.01). The same relationship was evident in the analysis restricted to patients with stage III or IV disease.

Stepwise Cox regression analysis was employed to investigate the prognostic significance of serum CD8 antigen level, serum IL2R level, erythrocyte sedimentation rate, stage, presence of B symptoms, histology, age, sex and race after adjusting the effect of each other. In this multivariate model, serum CD8 antigen level was found to have the most important impact on treatment outcome (p=0.002) whereas among other factors, only male sex was marginally associated with a worse prognosis (p=0.09).

11. ELEVATED SOLUBLE IL2R LEVEL IN SERUM OF CANCER PATIENTS UNDER THERAPEUTIC TREATMENT WITH IL-2

Generally, patients suffering from non-lymphatic cancers do not exhibit elevated levels of serum IL2R. However, the subsections below demonstrate that such patients receiving IL-2 therapy, who respond favorably to IL-2 therapy, demonstrate elevated levels of serum IL2R.

11.1. Serum IL2R Levels in Cancer Patient Treated with IL-2

As shown in FIG. 7, the serum level of soluble IL2R is highly elevated in a variety of cancer patients being treated by injection of IL-2. The level of measurable IL2R in serum remains elevated during the therapy treatment. The serum value of IL2R may be used to monitor a patient's response to therapy.

11.2. Elevated Serum /SERUM IL2R Levels in Cancer Patients Responding to IL-2 Therapy The CELLFREE® IL2R assay (Section 16, infra) was used to measure serum IL2R levels in patients with lung carcinoma who were receiving IL-2 therapy. Patients 1 and 2 were infused continuously from day 0 to day 14 with $3 \times 10^6$ U/ml of recombinant IL-2 and showed good response to the therapy. These patients demonstrated elevated levels of serum IL2R (see FIG. 8).

Patients 3, 4 and 5 were infused continuously from day 0 to day 14 with $2 \times 10^6$ U/ml of recombinant IL-2 and showed a poor or no response to the therapy. These patients demonstrated no increase in serum IL2R (see FIG. 8).

12. SERUM LEVEL OF SOLUBLE IL2R MAY BE USED TO DIFFERENTIALLY DIAGNOSE BETWEEN TRANSPLANT REJECTION AND THERAPEUTIC TOXICITY AND TO MONITOR THERAPEUTIC TOXICITY

Soluble T cell surface molecules such as the IL2R can be useful in the monitoring of immune status and graft rejection. The following studies demonstrate this utility.

Serum IL2R was measured in patients with renal transplants using the assay described in Section 6.2. Currently, a highly effective approach to prolonging the survival of graft organs is to suppress the cellular immune response using a number of therapeutic reagents, including monoclonal antibodies against human T cells, anti-lymphocyte antiserum, and immunosuppressant drugs. One of the immunosuppressive drugs currently prescribed for many organ transplant recipients is Cyclosporin A (CsA), a fungal-derived cyclic peptide. CsA appears to have specificity for lymphoid cells and inhibits the production of IL-2 in the early time point of T cell activation. However, the clinical use of CsA in transplant patients has serious problems due to the presence of significant toxicity.

Currently, the most effective diagnostic method of monitoring dysfunction in renal transplantation recipients is to measure serum level of creatinine. However, this monitoring method cannot distinguish between toxicity caused by an immunosuppressant drug such as CsA and true renal rejection (FIG. 9). As shown in Table VII, measurement of IL2R-like macromolecules in patients, serum is useful for distinguishing between CsA toxicity and renal rejection.

TABLE VII

SERUM LEVEL OF SOLUBLE IL-2 RECEPTOR IN RENAL TRANSPLANT PATIENTS MEASURED IN UNITS/ML

| Clinical Samples | Mean | Standard Deviation | No. of Patients |
|---|---|---|---|
| Pre-transplant (dialysis) | 721 | 434 | 18 |
| Normals | 150 | 105 | 20 |
| Stable transplant | 270 | 206 | 89 |
| CsA toxicity | 493 | 241 | 12 |
| Rejection (Before therapy) | 1032 | 584 | 13 |
| Viral infection | 1420 | 555 | 4 |
| During immuno-therapy with antibody OKT3 or ATG | 1758 | 724 | 23 |

In this experiment, serum level of IL2R remained low or slightly elevated in response to CsA toxicity, whereas IL2R level rose in response to renal rejection. Thus, in combination with serum creatinine measurement, the measurement of immune response as indicated by serum level of IL2R is useful to monitor effects of therapeutic treatments. Furthermore, the measurement of IL2R levels is useful as a method of differential diagnosis between CsA toxicity and renal rejection. This noninvasive measurement is preferred over existing methods of differential diagnosis between CsA toxicity and renal rejection which involves the examination of a biopsy specimen from a grafted kidney.

Similar observations have been made in liver transplantation patients. As shown in Table VIII, patients with liver transplant rejections have elevated levels of soluble IL2R in their serum. Decreased serum levels of IL2R were found in patients who showed no signs of rejection after transplantation.

TABLE VIII

SERUM LEVEL OF SOLUBLE IL-2 RECEPTOR IN LIVER TRANSPLANT PATIENTS MEASURED IN UNITS/ML

| Clinical Samples | Mean | No. Of Patients |
|---|---|---|
| Pre-transplant | 647 | 4 |
| Stable transplant | 600 | 1 |
| Rejection | >1500 | 3 |

13. PLASMA IL2R LEVELS IN RENAL ALLOGRAFT RECIPIENTS

In the examples described in the subsections below, the CELLFREE® Interleukin-2 Receptor Kit was used to measure serum levels of IL2R in renal allograft patients. Those patients who experienced true allograft rejection presented elevated serum levels of soluble IL2R.

13.1. Patients and Methods

Thirty-two patients who received an HLA non-identical renal allograft from cadaver or living related donors were studied. Patients were maintained on steroids and cyclosporine (CsA) or azathioprine. Rejection episodes were diagnosed on standard clinical and pathologic grounds (including a progressive elevation of serum creatinine level accompanied by one or more of the following: oliguria, fever, or weight gain). CsA levels were measured in plasma by radioimmunoassay. CsA toxicity was defined as a progressive elevation of serum creatinine level associated with a plasma level of greater than or equal to 700 ng/ml which responded to decreased dosages of CsA. Rejection episodes were treated with pulse steroids, anti-T3 monoclonal antibody (mAb) OKT3 (Ortho Pharmaceuticals) or AT-GAM ™ (horse anti-thymocyte globulin, Upjohn).

Plasma (citrate) for IL2R assay was taken before transplantation and at intervals of 1-2 times per week for the first several weeks and at weekly-monthly intervals thereafter, and stored at $-70°$ C. The IL2R assay was done using the CELLFREE® Interleukin-2 Receptor Test Kit (T Cell Sciences, Inc., Cambridge, Mass.) (see Section 16, infra). The test employs two non-competing monoclonal antibodies to the human IL2R in which the first antibody (mAb 2R12) was coated on the plastic microwells, washed, blocked, and 50 μl of test sample was applied with 100 μl of diluent. After a 2 hour incubation, the wells were washed, and the indicator antibody conjugated to horseradish peroxidase was added. After another 2 hours, the wells were washed, and orthophenylenediamine (OPD) was added. The reaction was quenched after 30 minutes with 1N sulfuric acid and the absorbance was measured at 490 nm. A standard curve was generated using serial dilutions of a supernatant from phytohemagglutinin (PHA) stimulated peripheral blood mononuclear cells which was defined as a value of 1000 units/ml. The summary data (Table IX) excludes the first 4 patients studied before the values were converted to PHA units. Normal plasma samples were from healthy laboratory personnel.

13.2. PLASMA CONTAINS ELEVATED LEVELS OF SOLUBLE IL2R DURING EPISODES OF RENAL ALLOGRAFT REJECTION

The data for plasma IL2R levels in the tested patients are summarized in Table IX.

TABLE IX

| Sample | PLASMA IL2R LEVELS | | |
|---|---|---|---|
| | N | Units/ml* | p (t test) |
| Normals | 20 | 150 ± 105 | |
| Pre-Transplant (Dialysis) | 14 | 800 ± 450 | <0.001 vs. Normal |
| Stable Transplant | 63 | 266 ± 205 | <0.02 vs. Normal |
| Rejection | 15 | 1050 ± 637 | <0.001 vs. Stable |
| During OKT3/ATG Therapy | 20 | 1788 ± 726 | <0.004 vs. Rejection |
| Viral Infection | 6 | 1076 ± 654 | <0.001 vs. Stable |
| Cyclosporin Nephrotoxicity | 13 | 430 ± 218 | <0.003 vs. Rejection |

*Arbitrary units, based on a PHA supernatant standard defined as 1000 U/ml; data for 28 patients and 20 normal laboratory personnel, mean ± standard deviation.

Patients on chronic dialysis (pre-transplant samples) had levels significantly elevated above the normal controls (p less than 0.001). These values fell toward normal levels in the first week after transplantation. Samples from patients with stable renal function showed values slightly above normal (p less than 0.02). In contrast, patients with acute rejection episodes showed levels that averaged significantly higher than stable patients. These samples, taken at a time when the serum creatinine level had risen, but before anti-rejection therapy had begun, had elevated IL2R levels in 10 of 13 rejection episodes. Shortly after treatment with anti-T cell monoclonal antibodies (OKT3 or ATG), IL2R levels increased further. This rise was evident in samples taken as early as one hour after the first dose of mAb OKT3 (mean rise of 36% in 5 paired samples, p less than 0.05). An exception was seen in a patient given mAb ATG prophylactically, who presumably did not have preexisting activated T cells. Patients with CsA nephrotoxicity had levels significantly below those with rejection (p less than 0.003). Three episodes of azotemia (without biopsies) could not be classified (improvement following a reduction of CsA and an increased in other immunosuppression) and were not used for the data analysis. Two patients had serious viral infections (cytomegalovirus, herpes simplex virus) and another had a viral syndrome with diarrhea; all showed marked elevation of IL2R levels. A patient with renal failure due to renal artery stenosis (Cr 3–4 mg %) and a patient with hemolytic uremic syndrome (Cr 5–6 mg %) did not show the elevation of IL2R levels seen in the patients with rejection.

In allograft rejection, activated T cells are found in the blood and in the graft (van Es, A., et al., 1984, Transplant. 37:65; Hancock, W. W., et al., 1985, Transplant. 39:430); however, the elevation in the amount of soluble/released IL2R observed in these experiments was unexpected, with the observed level equivalent to that which occurs in vitro in cultures with PHA stimulation. We also found elevated levels of IL2R in certain infections.

Administration of OKT3 or ATG anti-T cell mAbs was followed by a rise in IL2R level, presumably due to release of cellular IL2R consequent to cell injury by the antibodies. An exception to this observation occurred when ATG was given prophylactically. Thus progressive elevation of IL2R levels may be a valuable confirmatory test during anti-T cell antibody therapy.

Patients on chronic dialysis had increased concentrations of IL2R in the plasma. These patients are not known to have increased T cell activation and indeed have been found to have impaired T cell function. The nature of the defect in chronic renal failure remains enigmatic, although evidence points to immunosuppressive factors in uremic serum or plasma (Fehrman et al., 1980 $J.$ $Clin.$ $Nephrol.$ 14: 183). It is possible that the soluble IL2R itself is immunosuppressive, since it is able to bind IL-2 (Rubin, L. A., et al., 1986, $J.$ $Immunol.$ 137:3841–3844) and thus could compete with the IL2R on the T cell surface. The reason for the elevation of IL2R in chronic uremia is not known. The simplest explanation is that the soluble IL2R is normally excreted by the kidney. While further studies are needed to address this question, our initial data argue against a simple relationship between renal function and IL2R levels, since acute azotemia due to certain other causes (renal artery stenosis, hemolytic uremic syndrome, and CsA nephrotoxicity) do not have marked elevations of IL2R as a rule.

Our data indicate that the plasma contains increased amounts of immunoreactive IL2R during most episodes of renal allograft rejection, and suggest that assay for plasma/serum IL2R may be useful clinically in the differential diagnosis of renal allograft rejection, especially in distinguishing CsA nephrotoxicity.

14. A COMPARISON OF SERUM IL2R LEVELS AND ENDOMYOCARDIAL BIOPSY GRADES IN THE MONITORING OF CARDIAC ALLOGRAFT REJECTION

The current clinical success of cardiac transplantation is related to more effective immunosuppression based on the use of Cyclosporin A and the monitoring of allograft rejection using sequential endomyocardial biopsy (Austen, W. G., and Cosimi, A. B., 1984, $N.$ $Engl.$ $J.$ $Med.$ 311:1436–1438). Endomyocardial biopsy is relatively safe and reliable in adult allograft recipients but it is an invasive technique associated with some morbidity which cannot be performed with ease in infants and small children. Furthermore, the interpretation of biopsies is subjective and it is an expensive monitoring technique. However, endomyocardial biopsy is currently the only accepted means of diagnosing cardiac allograft rejection prior to the onset of potentially irreversible rejection.

Cardiac allograft rejection is primarily a cellular immune reaction involving the activation of T lymphocytes. The process of T cell activation is accompanied by expression of interleukin 2 receptors (IL2R). The experiments described below were designed to test the diagnostic value of serum IL2R levels for monitoring cardiac allograft rejection compared with endomyocardial biopsy. IL2R levels in 56 sera from 6 cardiac transplant patients obtained at the time of endomyocardial biopsy correlated (r=0.56) with the histological grade of rejection. For biopsy grades less than 2.0, the mean serum IL2R level was 387±41 units/ml whereas for biopsies diagnosed as rejection (greater than or equal to 2.0), the mean IL2R level was 1017±178 units/mL (p less than 0.0001). The threshold serum level for rejection was calculated to be 545 units/ml. In patient sera with IL2R levels below 545 units/ml, corresponding biopsies showed no evidence of rejection to 40 of 42 samples (specificity=95%). Levels of IL2R above 545 units/ml were present in 8 of 14 instances where the corresponding biopsy showed significant rejection (sensitivity=57%). These data suggest that normal IL2R levels indicate the absence of cardiac allograft rejection whereas elevated IL2R levels are a strong indicator of rejection.

14.1. Methods

Fifty-six right ventricular endomyocardial biopsies were obtained between 3 and 752 days (mean+SEM, 159±22) post transplantation from 6 adult orthotopic transplant recipients using standard techniques (Dec. G. W., et al., 1985, *N. Engl. J. Med.* 312:885-890). At least five fragments of endomyocardium were examined by light microscopy, immunoperoxidase and immunofluorescence for evidence of cardiac allograft rejection. Biopsies were graded prospectively without knowledge of the IL2R levels using a modification of the Stanford criteria (Mason, J. W. and Billingham, M. E., 1980, *Progress in Cardiology* 9:113-146):

| Grade | Histology |
| --- | --- |
| 0.0 | Normal |
| 0.5 | Rare foci of perivascular lymphocytic infiltrates |
| 1.0 | Occasional foci of perivascular and/or interstitial lymphocytic infiltrates |
| 1.5 | Multiple foci of perivascular and interstitial lymphocytic infiltrates without myocyte necrosis |
| 2.0 | Multiple foci of lymphocytic infiltrates associated with one or more foci of myocyte necrosis |
| 2.5 | Diffuse interstitial lymphocytic infiltrate containing occasional eosinophils and associated with multiple foci of myocyte necrosis |
| 3.0 | Diffuse lymphocytic infiltrate containing eosinophils and neutrophils, interstitial hemorrhage, edema and multiple foci of myocyte necrosis |

All biopsies were graded with respect to their most severe component. A histological grade of 2.0 or greater was considered indicative of rejection requiring additional treatment.

Serum obtained with each biopsy for immunofluorescence studies was frozen at −20° C. Aliquots of each sample were analyzed by the double monoclonal antibody sandwich technique using noncompeting monoclonal antibodies to human IL2R (CELLFREE®, T Cell Sciences, Inc., Cambridge, Mass., see Section 16, infra). The normal IL2R level as determined from 157 blood donor samples was 267±119 (+SD) units/ml.

All patients were treated with maintenance immunosuppression consisting of prednisone and cyclosporin A. Five patients also received azathioprine. Rejection episodes were initially treated with increased dosages of steroids. Anti-lymphocyte therapy with ATG (anti-thymocyte globulin) or OKT-3 (Orthoclone OKT3 monoclonal antibody, Ortho Pharmaceutical Corp., Raritan, N.J.) was given to patients with rejection that was unresponsive to additional steroids.

Statistical analyses were performed using RS/1 software (Bolt, Beranek and Newman, Cambridge, Mass.) routines for nonparametric, linear regression and non-linear regression analyses as appropriate. Mean values are expressed with their standard error.

14.2. Normal IL2R Levels Indicate the Absence of Cardiac Allograft Rejection Where As Elevated IL2R Levels Strongly Indicate Rejection The overall results are shown graphically in FIG. 10, and complete data for two patients are shown in FIG. 11. For pathological grades of rejection less than 2.0, the mean IL2R level was 387±41 units/ml (n=46, range 156-1386) whereas the mean level for grade 2.0 and higher was 1017±178 units/ml (n=10, range 328-2298). The difference was highly significant with p less than 0.0001. Serum IL2R levels showed an overall linear correlation of 0.56 (p=0.0001) with the histological grade of rejection on corresponding biopsies. However, the data was best fit (r=0.44, f=21, p=0.0001) using the nonlinear regression shown in FIG. 10. The threshold level of IL2R for rejection calculated from this analysis was 545 units/ml.

Levels of IL2R less than 545 units/ml were associated with rejection grades of less than 2.0 in 40 of 42 measurements (specificity=95%). The mean biopsy score for this group was 0.5±0.1 with a range of 0 to 2.0. The two normal IL2R measurements associated with biopsy grades of 2.0 occurred sequentially in Patient B during an episode of rejection under treatment with additional steroids (FIG. 11). Both concomitant biopsies showed resolving rejection, that is, myocyte necrosis was still present but the lymphocytic infiltrate was much less intense than on the initial biopsy diagnosed as grade 2.0 rejection.

Serum IL2R levels greater than 545 units/ml had corresponding biopsy scores of 2.0 or higher in 8 of 14 measurements giving a sensitivity of 57%. The mean biopsy score was 1.6±0.2 with a range from 0 to 2.5. This was significantly different from the mean biopsy score of the normal IL2R group (p=0.0001). In five of six instances where biopsy scores less than 2.0 were associated with serum levels greater than 545 units/ml of IL2R, the elevated level either preceded (n=2; 2d and 11d) or followed an episode of treated rejection (n=3; 9d, 12d and 35d). The sixth instance of elevated level was from the initial post-transplant serum sample of Patient B (FIG. 11) in whom the histological appearance of the corresponding biopsy was grade 0 but the explanted heart showed active lymphocytic myocarditis.

There was no significant correlation between serum IL2R levels and Cyclosporin A levels or the days post transplantation.

The data show that a normal level of circulating IL2R appears to exclude allograft rejection diagnosed on endomyocardial biopsy whereas an elevated serum IL2R level is a strong indicator of cardiac allograft rejection. The apparent low sensitivity (57%) may be more a reflection of the fallibility of endomyocardial biopsy and its interpretation rather than the IL2R measurements in this analysis. Endomyocardial biopsy may miss foci of rejection. In addition, false positives may be due to timing differences in the phenomena being measured, i.e. increases in serum IL2R may occur before actual rejection can be diagnosed by biopsy (as defined by a histological grade of greater than 2.0). In fact, elevated levels of IL2R were associated with rejection in 6 of 6 documented episodes and in two instances, elevated IL2R levels preceded histological evidence of rejection. IL2R levels could possibly prove useful in determining if a treated rejection is ongoing or resolving. Treatment of renal transplant patients with ATG or OKT-3 antibodies results in marked elevations of IL2R. Similarly, following ATG therapy in Patient B, the IL2R level rose dramatically but the corresponding biopsy grade was only 1.0 (FIG. 11). However, Patient B's biopsy eleven days later showed a grade 2.5 rejection and the corresponding IL2R level was 2298 units/ml.

Elevation of IL2R levels also occurs during severe viral infections, certain autoimmune disorders (Nelson, D. L., 1986, *Fed. Proc.* 45:377 (abstract), T cell leukemias (MacKeen, L., et al., 1986, *Fed. Proc.* 45:454 (abstract), and chronic renal failure. Patient B, who was transplanted during an episode of recurrent lymphocytic myocarditis, had serum IL2R levels that were elevated immediately post-transplant without evidence of rejection on the biopsy. Thus, the presence of one of the above conditions, and possibly other situations, may result in elevations of IL2R in cardiac transplant patients that are not related to rejection.

The data indicate that serial measurements of IL2R in the serum of cardiac allograft recipients may prove useful in detecting and monitoring rejection. An elevated serum IL2R level, even in the presence of other diseases that elevate IL2R, indicates the need for endomyocardial biopsy to confirm or exclude rejection. The finding of normal serum IL2R levels appears to exclude rejection and thus may be used to forestall performance of endomyocardial biopsy. Measurement of IL2R levels may prove especially useful in infants and small children with cardiac allografts in whom the endomyocardial biopsy is associated with higher risks and more technical difficulty. This approach may prove valuable in reducing both the morbidity and the expense of managing the cardiac allograft patient.

15. SERUM MEASUREMENT OF SOLUBLE IL2R MAY BE USED FOR STAGING VIRAL INFECTIONS

Acquired Immune Deficiency Syndrome (AIDS) is characterized by a severe deficiency of cellular immunity, increased opportunistic infections, and certain malignancies. The human T cell leukemia (T-lymphotropic) virus Type III (HTLV-III) has been closely linked with the disease, and patients with the active disease exhibit severe T cell defects Clinically, AIDS is manifested by profound lymphopenia and marked reduction of T cell function. However, patients infected with HTLV-III virus (HTLV-III seropositive) do not necessarily exhibit any clinical abnormality. It is therefore essential to distinguish various clinical subgroups of patients who have been exposed to HTLV-III virus and those who have AIDS-related illnesses, e.g. AIDS related complex (ARC).

As shown in FIG. 12, the level of serum IL2R correlated with activities of the disease. Therefore, the measured value of soluble IL2R in serum, in conjunction with other clinical tests, provides an index of the severity of the disease in the subject.

16. CELLFREE ® ENZYME IMMUNOASSAY FOR THE DETECTION OF SOLUBLE, RELEASED IL2R

The subsections below describe a serum immunoassay test kit, using two distinct murine monoclonal antibodies directed against different epitopes of the IL2R for the detection of a cell-free T cell IL2R in serum or plasma. The CELLFREE ® Interleukin-2 Receptor Test Kit (T Cell Sciences, Inc., Cambridge, Mass.) is a direct enzyme immunoassay for the quantitative detection of released, soluble IL2R in human serum (see also, Rubin et al., 1985, *J. Immunol.* 135:3172-3177). Accurate quantitation of the serum level of IL2R may be important in characterizing immune disorders, in monitoring disease activity, and in evaluating the efficacy of immunotherapeutic treatment of such disorders.

The CELLFREE ® Interleukin-2 Receptor Test was used to detect cell free IL2R in various patient and control sera. The soluble or released form of IL2R was found to be elevated in the serum of patients with leukemia and certain immunological disorders. The level of serum IL2R in active adult T cell leukemia (ATL) patients was highly elevated, but remained low in HTLV-1 seropositive asymptomatic patient group.

16.1. Principles of the Method

The CELLFREE ® Interleukin-2 Receptor Test Kit is a sandwich enzyme immunoassay for the determination of IL2R levels in human serum or plasma. An anti-IL2R monoclonal coating antibody is first adsorbed onto polystyrene microtiter wells. IL2R present in the sample or standard binds to the antibody coated well; unreacted sample components are removed by washing. An enzyme conjugated anti-IL2R monoclonal antibody directed against a second epitope on the IL2R molecule binds to the IL2R captured by the first antibody and completes the sandwich. After removal of unbound enzyme-conjugated anti-IL2R by washing, a substrate solution is added to the wells. A colored product is formed in proportion to the amount of IL2R present in the sample. The reaction is terminated by addition of stop solution and absorbance at 490 nm is measured. A standard curve is prepared from four IL2R standards. Unknown values are determined from the standard curve.

16.2. Cellfree ® Test Kit Components and Suggestions

Each CELLFREE ® Interleukin-2 Receptor Test Kit has reagents sufficient for 96 wells. The expiration date for the complete kit is stated on the outer box label and the recommended storage temperature is 2°-8° C.

16.2.1. Reagents Supplied (a) Anti-IL2R Coating Antibody—1 Vial: Each vial contains murine monoclonal antibody to human interleukin-2 receptor. Store at 2°-8° C.
(b) HRP Conjugated Anti-IL2R Antibody—1 Vial: Each vial contains horseradish peroxidase (HRP) conjugated murine monoclonal antibody to human interleukin-2 receptor. Store at 2°-8° C.
(c) Sample Diluent—1 vial: Each vial contains serum protein in a buffered solution. Store at 2°-8° C.
(d) Interleukin-2 Receptor (IL2R) Standards—4 vials: Each vial contains released or soluble human interleukin-2 receptor (IL2R) in a buffered solution. Store at 2°-8° C.

(e) OPD Tablets—1 vial: Each vial contains 14 OPD tablets composed of o-phenylenediamine in an inert binder. Store dessicated at 2°–8° C.

Also supplied:
(f) 96 Well Microtiter Plate with Holder Each plate consists of twelve 8-well strips with holder. Store uncoated plates at 2°–26° C.
(g) Directions for Use.

16.2.2. Materials Required but not Provided

Reagents

The following reagents must be prepared according to directions in Section 16.2.5, infra. Following the name of each reagent is a list of components needed to prepare that reagent. Each reagent should be made with distilled, deionized water.

(a) PBS Coating Buffer: A commercially available isotonic phosphate buffered saline (PBS) (Dulbecco's PBS without calcium or magnesium is recommended) or NaCl, KCl, $KH_2PO_4$, $Na_2HPO_4.7H_2O$; thimerosal.

(b) Washing Buffer: PBS Coating Buffer (Reagent a.) plus polyoxyethylenesorbitan monolaurate (Tween 20).

(c) Blocking Buffer: Washing Buffer (Reagent b.) plus bovine serum albumin (a neutral pH, fatty acid free preparation is recommended).

(d) Substrate Buffer: Citric acid monohydrate, $Na_2HPO_4.7H_2O$, thimerosal, 30% hydrogen peroxide.

(e) Stop Solution: Concentrated $H_2SO_4$.

Materials

Precision pipettes with disposable tips:
50 and 100 μl micropipettes
50–200 μl adjustable multiwell pipettor.
Disposable reagent troughs for multiwell pipettor.
Beakers, flasks, cylinders necessary for preparation of reagents.
Microtiter plate washing/aspiration device.
Constant temperature air incubator, 37°±2° C.
Disposable pipettes and test tubes for preparation of OPD (o-phenylenediamine) Substrate Solution.
Micro titer plate reader for measurement of absorbance at 490 nm.

16.2.3. Reagent Precautions

The following precautions are suggested:
Do not mix reagents from different kit lots.
Do not use reagents beyond expiration date on label.
In order to avoid reagent contamination, use disposable pipette tips and/or pipettes.
Sodium azide inactivates HRP. Solutions containing sodium azide should not be used in this assay.
Do not expose OPD reagents to strong light during storage or incubation.
Avoid contact of OPD and Stop Solution with skin and mucous membranes.
If these reagents come into contact with skin, wash thoroughly with water.
Avoid contact of OPD Tablets, OPD Substrate Solution and Stop Solution with any metal surfaces. Disposable glassware or test tubes are recommended for OPD substrate Solution. If nondisposable glassware is used, it should be acid washed and thoroughly rinsed with distilled, deionized water.

16.2.4. Specimen Collection and Handling

A venous blood sample is collected aseptically. Serum or EDTA plasma is suitable for use in the assay. Remove the serum or plasma from the clot or red cells, respectively, as soon as possible after clotting and separation.

Samples containing a visible precipitate should be clarified prior to use in the assay. Grossly hemolyzed or lipemic specimens should not be used.

Samples can be stored up to seven days at 2°–8° C. If the length of time between sample collection and analysis is greater than seven days, it is preferable to store the sample frozen. Freeze-thaw cycles should be avoided since they may denature the interleukin-2 receptor molecule.

Prior to assay, frozen sera or plasma should be brought to room temperature slowly and gently mixed by hand. Thawing samples in a 37° C. bath, vortexing, or sharp agitation of samples should be avoided.

Sodium azide inactivates HRP. Therefore, specimens containing sodium azide should not be used in this assay.

16.2.5. Reagent Preparation

Except for the OPD Substrate Solution, the following reagents should be prepared prior to Plate Coating, Section 16.2.6, infra:

PBS Coating Buffer

A commercially available isotonic phosphate buffered saline (Dulbecco's PBS, without calcium or magnesium) is recommended. Alternatively, the laboratory may prepare its own PBS using the following procedure:

Dissolve:
8.00 g NaCl
0.20 g $KH_2PO_4$
0.20 g KCl
2.16 g $Na_2HPO_4.7H_2O$
in approximately 800 ml of distilled, deionized water. Add distilled, deionized water to a final volume of 1.00 liter. Verify that the buffer is at pH 7.4±0.2. Mix well.

For either commercially available or laboratory prepared PBS, 0.10 g thimerosal is added as a preservative. Mix well. Store at 2°–26° C. for up to 6 months.

Washing Buffer

Add 0.40 ml of polyoxyethylenesorbitan monolaurate (Tween 20) to 800 ml of PBS Coating Buffer. Mix well. Store at 24°±2° C. for up to 30 days. The Washing Buffer is stable for 30 days. Washing Buffer may be prepared as needed according to Table X:

TABLE X

| Procedure | PBS Coating Buffer (ml) | Tween 20 (ml) |
|---|---|---|
| Assaying 0–32 Tests | 400 | 0.2 |
| Assaying 33–64 Tests | 600 | 0.3 |
| Assaying 65–96 Tests | 800 | 0.4 |

Blocking Buffer

Add 1.0 g bovine serum albumin to 100 ml of Washing Buffer. Mix well. Store at 2°–8° C. for up to 30 days before use.

Substrate Buffer

Dissolve:
0.36 g citric acid-monohydrate
1.74 g $Na_2HPO_4.7H_2O$
0.01 g thimerosal
in approximately 80 ml of distilled, deionized water. Add distilled, deionized water to a final volume of 100 ml. Mix well. Verify that the buffer is at pH 6.3±0.2. Add 75 µl of 30% $H_2O_2$. Mix well. Store at 2°–8° C. for up to 60 days.

Stop Solution (2N $H_2SO_4$)

Add 5.8 ml concentrated $H_2SO_4$ carefully to approximately 80 ml of distilled, deionized water (acid must be added to water). Add distilled, deionized water to a final volume of 100 ml. Mix well. Store at 2°–26° C. for up to 6 months.

The following reagent should be prepared approximately 30 minutes prior to the end of the incubation with conjugate (Section 16.2.7., infra).

OPD Substrate Solution (a) For each strip of 8 wells used, pipette 1.0 ml of Substrate Buffer into a clean glass test tube; (b) Add one OPD Tablet for each ml of Substrate Buffer in the test tube. OPD Tablets should be transferred using nonmetallic forceps or equivalent. Cover the test tube securely and vortex frequently until all OPD Tablets have dissolved. Use within 30 minutes.

16.2.6 Suggested Plate Coating Protocol

The following protocol is recommended (N.B. the entire 96 well microtiter plate should be coated at the same time):

(a) Measure 11.9 ml of PBS Coating Buffer into a clean test tube or flask. Add 0.1 ml of Anti-IL2R Coating Antibody Mix well.
(b) Dispense 100 µl of this solution into each well for the entire microtiter plate.
(c) Cover the plate with a plastic sealer and incubate at room temperature (24°±2° C.) in a humid environment for 16–72 hours.
(d) Discard coating solution from all wells.
(e) Add 300 µl of Blocking Buffer to each well for the entire microtiter plate.
(f) Replace the plastic sealer and incubate the plate for 2 hours at 37°±2° C.
(g) If samples are to be run immediately, proceed with assay protocol. If samples are to be run at a later time, store antibody coated wells containing Blocking Buffer covered at 2°–8° C. until use. Wells are stable for up to 45 days after coating.

16.2.7. Suggested Assay Protocol

This assay can be performed only after Plate coating, Section 16.2.6, supra, has been completed:

(a) Mix all reagents thoroughly without foaming before use.
(b) Determine the number of strips required to test the desired number of patient samples plus 10 wells needed for running blanks and standards (8 wells per strip). Remove unneeded strips from holder and store at 2°–8° C., covered with a plastic sealer.
(c) Discard Blocking Buffer from coated wells.
(d) Wash the wells 3 times with Washing Buffer. Discard Washing Buffer after each wash.
(e) Remove residual Washing Buffer by tapping the inverted plate on clean absorbant paper.
(f) Leaving the blank wells empty, pipette 50 µl of standard or sample, in duplicate, into antibody coated wells.
(g) Leaving the blank wells empty, add 100 µl of Sample Diluent to all other wells. Care should be taken to avoid cross contamination of samples.
(h) Cover the wells with a plastic sealer and incubate at 37°±2° C. for 2 hours in a constant temperature air incubator.
(i) Remove and discard sealer. Aspirate solution from all wells. Wash wells 3 times with approximately 350 µl of Washing Buffer, with thorough aspiration between washes.
(j) Leaving the blank wells empty, add 100 µl of HRP-Conjugated Anti-IL2R Antibody to all other wells.
(k) Cover with a fresh plate sealer and incubate at 37°±2° C. for 2 hours in a constant temperature air incubator. Approximately 30 minutes prior to the end of incubation with conjugate, prepare OPD substrate solution as directed in section 16.2.5, supra.
(l) Remove and discard sealer. Aspirate solution from all wells. Wash wells 3 times with approximately 350 µl of Washing Buffer with thorough aspiration between washes.
(m) Pipette 100 µl of OPD Substrate Solution into all wells, including blank wells. Incubate uncovered for 30 minutes at room temperature (24°±2° C.).
(n) Pipette 50 µl Stop Solution into all wells, including blank wells.
(o) Read absorbance of wells at 490 nm versus substrate blank. The absorbance should be read as soon as possible after the completion of the assay, but may be read up to 2 hours after addition of Stop Solution when wells are kept protected from light at room temperature. See Section 16.2.10, infra.

16.2.8. Construction of a Standard Curve (a) Record the absorbance at 490 nm for each standard well.
(b) Average the duplicate values and record the averages.
(c) Plot the absorbance (vertical axis) versus the IL2R concentration in U/ml (horizontal axis) for the standards using a linear scale.
(d) Draw the best fitting curve.

16.2.9. Patient Samples (a) Record the absorbance at 490 nm for each patient sample well.
(b) Average the duplicate values and record the averages.
(c) Locate the average absorbance value which corresponds to each sample on the vertical axis and follow a horizontal line intersecting the standard curve. At the point of intersection, read the IL2R concentration (U/ml) from the horizontal axis.

16.2.10. Limitations

Since assay conditions may vary from assay to assay, a standard curve should be established for every run. Since cross contamination between reagents will invalidate the test, disposable pipette tips should be used. Reusable glassware should be washed and thoroughly rinsed of all detergent before use. Disposable flasks or glassware are preferred. Thorough washing of the wells between incubations is required:

(a) Completely aspirate well contents before dispensing fresh wash solution.
(b) Fill with wash solution to the top of the well for each wash cycle (approximately 350 μl).
(c) Do not allow wells to sit for extended periods between incubation steps.

Only samples with absorbance values falling within the range of the standard curve should be assigned an IL2R concentration from the curve. Samples with absorbance above the highest standard can be diluted with sample diluent and retested. Recommended dilution is 1/10 (50 μl sample plus 450 μl sample diluent). A small percentage of samples may need greater dilution. The correct concentration of IL2R is then obtained by multiplying the IL2R level in U/ml of the diluted sample (from the standard curve) by the dilution used for testing.

Using the CELLFREE ® Interleukin-2 Receptor Test Kit, soluble or released IL2R values were not affected by the addition of up to 2 μg/ml of recombinant IL-2 to test samples.

16.3. Cellfree ® Reagents

16.3.1. Monoclonal Antibodies

Mouse monoclonal antibodies were generated according to procedure as described (Rubin, L. A., et al., 1985, *Hybridoma* 4:91-102; Kohler, G. and Milstein, C., 1975, *Nature* 256:495-497). The two monoclonal antibodies selected (2R12, 7G7) are directed against different epitopes of IL2R. Both antibodies were shown to precipitate a 55 kilodalton (kd) cell surface protein identified by anti-Tac mAb. The IgG antibodies were purified to greater than 95% homogeneity by chromatography on immobilized protein A (BioRad) according to the manufacturer's instructions (Affi-gel protein A MAPS II kit instruction manual, BioRad Laboratories, Calif.). Enzyme-antibody conjugates were prepared by labeling IgG with horseradish peroxidase essentially as described (Wilson, M. B. and Nakane, P. K., 1978, *Immunofluorescence and Related Staining Techniques*, Knapp, W., K. Holubar, and G. Wicheds, eds., Elsevch/Norton-Holland Biomedical Press, p. 215).

16.3.2. Standards

IL2R standards were prepared from supernatants of phytohemagglutinin (PHA) stimulated peripheral blood mononuclear cell (PBMC) cultures. Lymphocytes were harvested after centrifugation over Ficoll-Paque (Pharmacia) according to the manufacturer's instructions. $10^6$ cells/ml were suspended in RPMI 1640 supplemented with 100 U/ml penicillin, 100 μg/ml streptomycin and 15% fetal bovine serum. PHA (Wellcome Diagnostics) was added to a concentration of 2.0 μg/ml. Cultures were maintained at 37° C. for 3-6 days. Supernatants were harvested by centrifugation at 200 × g for 8 minutes, and clarified by spinning at 10,000 × g for 10 minutes. IL2R levels were assigned a value in Units per ml (U/ml) based on activity in the enzyme immunoassay relative to a reference preparation of supernatant which was arbitrarily assigned a value of 1000 U/ml (Rubin, L. A., et al., 1985, *J. Immunol.* 135:3172-3177).

16.3.3. Patient Sera

Normal sera were collected from healthy blood donors and stored at 4° C. for up to 7 days and frozen at −70° C. for longer periods of time.

Adult T cell leukemia patient sera were provided by Dr. N. Yasudo (Kyoto University, Japan). Abnormal clinical sera samples were obtained from area hospitals and clinics.

16.3.4. PURIFIED IL2R

Purified IL2R was prepared by affinity chromatography of supernatant from PHA-stimulated PBMC cultures over an anti-IL2R immunoadsorbant. The affinity column was prepared by coupling 1 mg anti-IL2R antibody (2R12) to 1 ml Reactigel (Pierce) according to the manufacturer's instructions. 100 ml of PHA supernatant culture was applied to a 1 ml column. After washing the unbound material from the gel with 100 ml of phosphate-buffered saline (PBS), the IL2R was eluted in 5 ml of 0.2M glycine buffer, pH 2.8; dialyzed in water; lyophilized and resuspended in 0.5 ml PBS.

16.3.5. Interleukin-2

A commercially available recombinant IL-2, was the gift of Dr. James Kurnick (Massachusetts General Hospital, Boston, Mass.).

16.4. Cellfree ® IL2,R Assay

The CELLFREE ® Interleukin-2 Receptor Test Kit was used for all serum assays as follows: Wells of polystyrene microstrips were coated with antibody by incubation with 100 μl per well of a 1.5 μg/ml solution of anti-IL2R mouse mAb in PBS overnight at room temperature. Coating solution was discarded and wells were blocked for 2 hours at 37° C. with 300 μl of 1.0% bovine serum albumin, 0.05% Tween 20 in PBS. Wells were then washed 3 times with washing buffer (0.05% Tween 20 in PBS). The precoated microstrips were used in either a two-step assay or an improved shorter one-step procedure. For the two-step assay, 50 μl of sample, standard, or control was placed in each well. 100 μl of sample diluent, consisting of animal serum proteins and surfactant, was added to each well. Wells were incubated for 2 hours at 37° C., then washed 3 times with washing buffer. 100 μl of HRP-conjugated anti-IL2R antibody directed against a second epitope on the IL-2 receptor was added to each well and incubated for 2 hours at 37° C. After washing the wells 3 times with washing buffer, 100 μl of substrate solution (0.2% o-phenylenediamine [OPD], 0.0225% $H_2O_2$, 65 mM dibasic sodium phosphate, 17 mM citric acid) was added per well. Wells were incubated for 30 minutes at room temperature. The reaction was stopped by the addition of 50 μl of 2N $H_2SO_2$ to each well, and the absorbance of the wells at 490 nm was read using a Dynatech MR600 microtiter plate reader. All assay buffers and diluents contained 0.01% thimerosal as a preservative. Unknown samples were assigned values based on a standard curve constructed using standards which contained 0, 100, 400, and 1600 U/ml IL2R.

Alternatively, a faster one-step method was used as follows: 50 of standard, sample, or control was added to each well, followed by 100 μl of HRP-conjugated antibody. Wells were incubated for 2 hours at room temperature on a shaker platform at 150-180 rpm. After washing the well three times with washing buffer, 100 μl of substrate solution was added. Wells were incubated for 20 minutes at room temperature. The reaction was stopped by adding 100 μl of 2N sulfuric acid to each well. The absorbance was read and analyzed as described above.

16.4.1. Standardization

A typical standard curve is shown in FIG. 13. The sensitivity of the assay is calculated as the amount of IL2R giving two standard deviations above the absorbance of the zero standard and is approximately 50 U/ml. Samples with up to 1600 U/ml IL2R activity can be measured in the kit; greater levels can be quantitated if the sample is diluted prior to assay.

16.4.2. Precision

Intra and inter-assay precision are presented in Table XI. Intra-assay variation was determined for three serum pools with differing IL2R levels by testing 20 replicate samples of each pool in one assay run. The coefficient of variation (CV) ranged from 3.2 to 3.9%. Inter-assay variation was determined from the average of duplicate samples for 20 separate runs. The inter-assay CV ranged from 10 to 12% for the three serum pools tested.

TABLE XI

PRECISION MEASUREMENT OF THE IL2R ASSAY

| Sample | Mean (U/ml) | Standard Deviation (U/ml) | Coefficient of Variation (%) |
|---|---|---|---|
| INTRA-ASSAY PRECISION[a]: | | | |
| Serum Pool A | 386 | 14 | 3.7 |
| Serum Pool B | 636 | 25 | 3.9 |
| Serum Pool C | 1,029 | 33 | 3.2 |
| INTER-ASSAY PRECISION[b]: | | | |
| Serum Pool A | 414 | 50 | 12 |
| Serum Pool B | 688 | 73 | 11 |
| Serum Pool C | 1,109 | 107 | 10 |

[a]Intra-assay precision was determined from the mean of 20 assays per sample.
[b]Inter-assay precision was determined from the mean of the average of duplicate samples for 20 different runs.

16.4.3. Accuracy

Affinity-purified IL2R was added to normal human serum which had been stripped of endogenous IL2R by passage over an anti-IL2R affinity gel. Spiked samples with different levels of added IL2R were tested in the assay for IL2R. Recovery of IL2R was 95–103% of the expected result (Table XII).

TABLE XII

| ACCURACY OF THE IL2R ASSAY* | | |
|---|---|---|
| Expected Value (U/ml) | Recovered Value (U/ml) | Recovery (%) |
| 150 | 145 | 97 |
| 300 | 310 | 103 |
| 600 | 570 | 95 |
| 1200 | 1160 | 97 |

*Spiked samples were prepared by adding varying amounts of purified IL2R to a serum pool which had been stripped of endogenous IL2R.

16.4.4. Specificity of Assay and Effects of Interleukin-2

Both antibodies used in the immunoassay have been shown to recognize the same molecule as anti-Tac, an antibody previously shown to be specific for human IL2R (Uchiyama, T., et al., 1981, J. Immunol 126: 1393–1397). Immunoprecipitations of $^{125}$I-labeled surface proteins from phytohemagglutinin-stimulated lymphocytes, using these antibodies, reveal a diffuse 55 kd band, and sequential immunoprecipitations demonstrate that this molecule is identical to that precipitated by anti-Tac (Rubin, L. A., et al., 1985, Hybridoma 4:91–102). Thus, one of the antibodies (2R12) demonstrates competitive binding with anti-Tac in cytofluorometric analysis of activated lymphocytes. The enzyme immunoassay employing these antibodies detects a released form of IL2R in the culture supernatants of IL2R surface positive cells (Rubin, L. A., et al., 1985, J. Immunol. 135:3172–3177) and in the culture supernatant of mouse L cells transfected with a truncated form of the IL2R gene, but not in the supernatants of their normal counterparts (Treiger, B. F., et al., 1986, J. Immunol. 136:4099–4105).

The performance of the IL2R assay kit in the presence of added IL-2 was determined. Serum concentrations of added recombinant IL-2 (fIL-2) up to 5 μg/ml caused negligible interference in IL2R detection (FIG. 14). At 500 μg/ml of added fIL-2, the IL2R level was only 40% of the expected value. The IL-2 concentrations suggested for therapeutic trials are in the 10 μg/ml range and have a half life of less than 10 minutes in serum after initial injection (Lotze, M. T., et al., 1985, J. Immunol. 135:2865–2875). Therefore, therapeutic levels of IL-2 are not expected to cause significant interference in measurement of IL2R by this assay. Greater than 80% of the expected IL2R value was obtained at these concentrations of rIL-2. In addition, no detectable level of IL-2 in normal serum was observed.

16.4.5. IL2R Levels in Human Sera

The distribution of IL2R levels in normal human sera is presented in FIG. 14. The mean IL2R level of 174 healthy blood donors was 273 U/ml. The upper limit of normal for this group was 477 U/ml (mean+2 S.D.).

Serum IL2R levels for 22 of 23 patients with adult T cell leukemia were elevated above the normal level (FIG. 15). The majority of these patients had marked elevations of IL2R level (greater than 1600 U/ml).

The current test demonstrates a detectable level of released IL2R present in normal human sera and increased serum levels of IL2R in adult T cell leukemia patients (Rubin, L. A., et al., 1986, "Identification and Characterization of a Released Form of the Interleukin-2 Receptor, in Leukocytes and Host Defense, Oppenheim, J. J. and D. M. Jacobs, eds., Alan R. Liss, Inc., New York, pp. 95–102).

As an alternative to cell surface measurements, the availability of an enzyme immunoassay for the detection of released or soluble IL2R makes it possible to assess altered immune status in a new manner. This method can allow detection of IL2R released from sequestered as well as circulating activated cells. Invasive tissue sampling methods for obtaining compartmentalized cells is thus avoided. Furthermore, the serum IL2R assay can provide means for rapid retrospective analysis of stored serum to provide insight into immune regulation.

17. SOLUBLE IL2R MEASUREMENT AS AN INDICATION OF THE EXTENT OF BONE MARROW LEUKEMIC INFILTRATION IN HAIRY CELL LEUKEMIA PATIENTS

In the example herein, we describe the results of a clinical trial designed to determine the degree of correlation between two measurements of bone marrow hairy cell infiltration in patients with hairy cell leukemia, monitored during the major phases of alpha-interferon treatment and during subsequent observation: the bone marrow biopsy-based Leukemic Index and the serum-based IL2R level. Measurements were obtained through retrospective evaluation of serial biopsy and matching serum specimens from 81 hairy cell leukemia patients. There was a strong positive correlation between the two types of measurement, both for on- and off-treatment specimens. Thus, measurements of hairy cell infiltration derived using the bone marrow biopsy/histopathology procedure are equivalent to those derived using the CELLFREE® IL2R Test Kit. The results demonstrate that measurements of serum IL2R may be used to determine the extent of hairy cell infiltration of the bone marrow in hairy cell leukemia patients.

17.1. Procedures and Definitions

17.1.1. Assay for Soluble IL2R,

Serum IL2R was assayed using the CELLFREE® IL2R enzyme immunoassay as described in Section 16 supra, with the modifications described in the subsections below.

17.1.1.1. Specimen Collection and Handling

Specimen collection and handling were carried out according to the following:
1. Collect a venous blood sample in an evacuated tube without preservatives or additives. Allow sample to clot at room temperature.
2. Separate the serum fraction from the clot as soon as possible.
3. Turbid samples, or those containing a visible precipitate, should be centrifuged prior to use in this assay.
4. Samples may be stored up to seven days at 2°-8° C. If the length of time between sample collection and analysis is greater than seven days, the sample should be stored frozen at −20° C. Freeze-thaw cycles should be avoided since they may denature the interleukin-2 receptor molecule.
5. Prior to assay, frozen sera should be brought to room temperature slowly and then gently mixed by hand. Samples should preferably not be thawed in a 37° C. bath.
6. Samples should not be vortexed or sharply agitated.

17.1.1.2. Assay Procedure

Each standard or patient specimen was assayed in duplicate each time the test was performed. All reagents and serum specimens were allowed to come to room temperature prior to use. Procedures were carried out as follows:

Immunological Incubation

1. Label 12×75 mm polystyrene test tubes appropriately.
2. Pipette 50 μl of Standard or serum specimen into appropriate tube.
3. Pipette 150 μl of the HRP:Antibody Conjugate into each test tube.
4. Using non-metallic forceps, add one coated bead to each test tube. (Bead is coated with murine monoclonal antibody to human IL2R receptor, with desiccant.)
5. Shake the test tube rack to ensure mixing of sample and reagents.
6. Cover test tubes and incubate for 90±5 minutes at room temperature (20° to 30° C.) on a rotator set at 150 (±10) rpm.

Enzymatic Incubation

7. At the end of the immunological incubation, wash and aspirate the beads as described below:
   a. dispense a minimum of 2 ml of distilled water into each tube,
   b. aspirate all of the liquid from each tube,
   c. repeat steps a and b for a total of three washes, and
   d. ensure that all tubes have been aspirated thoroughly before proceeding to the next step.
   No more than 15 minutes prior to its addition, prepare the OPD substrate solution.
8. Pipette 200 μl of OPD substrate solution into each sample or Standard test tube and into two empty test to be used as substrate blanks.
9. Incubate test tubes for 30 minutes at room temperature (20° to 30° C.), without mixing.
10. Add 1.0 ml of Stop Solution to each test tube and to the substrate blank tubes.
11. Set spectrophotometer at 492 nm and adjust absorbance to zero using the substrate blank tubes.
12. Read and record the absorbance of each tube within one hour of adding the Stop Solution.
13. Calculate the results as described below.

17.1.1.3. Calculation of Assay Results

Serum IL2R values were expressed in units per ml (U/ml). 1000 units is defined as the amount of released or soluble IL2R present in 1.0 ml of a reference preparation of supernatant from phytohemagglutinin-stimulated peripheral blood lymphocytes.

There were two options used for reading the absorbance of the reaction tubes and calculating the results:

(i) Using a Spectrophotometer With a Microprocessor

The instrument automatically generates an internal calibration curve. At the completion of each assay, the absorbance value for each serum specimen is automatically converted to IL2R concentration in U/ml and the values printed out.

(ii) Using a Conventional Spectrophotometer and Manual Calculations

Construct a standard curve by plotting mean absorbance on the vertical (Y) axis versus the corresponding IL2R concentration on the horizontal (X) axis, using rectilinear graph paper.

Locate on the vertical axis the average absorbance value which corresponds to each serum sample and follow a horizontal line intersecting the standard curve. At the point of intersection, read the IL2R concentration (U/ml) from the horizontal axis.

Patients with progressive hairy cell leukemia may have levels of serum IL2R in excess of 3200 U/ml. For specimens with IL2R levels elevated beyond the standard curve, dilution and reassay were required. The specimen was diluted with an appropriate amount of specimen diluent (0 U/ml Standard) and mixed thoroughly. Each diluted specimen was reassayed according to the assay procedure, and calculations were performed using the appropriate dilution factor. The recommended dilution factor for hairy cell leukemia sera is 1:11.

17.1.2. Description of Bone Marrow Cytopathology/Histopathology Procedures

The following subsections present a description of the bone marrow cytopathology/histopathology procedure for the measurement of bone marrow hairy cell infiltration that was utilized during the clinical study described herein. Both a bone marrow aspiration and biopsy procedure were performed each time a bone marrow pathologic evaluation was ordered.

The bone marrow biopsy procedure is also described in "The Value of the Bone-Marrow Biopsy in the Diagnosis of Hairy Cell Leukemia" (Burke, J. S., 1978, *Am. J. Pathol.* 70:876). The bone marrow aspirate procedure is also described in Bouroncle et al. (1958, *Blood* 13:609) and Golomb and Vardiman (1978, *CA—A Cancer Journal for Clinicians* 28:265).

17.1.2.1. Bone Marrow Sampling Procedures

Bone marrow specimens were obtained from the posterior iliac crest. Bone marrow aspiration specimens, consisting of bone and bone marrow fragments, were removed by suction using a 16 gauge needle and a 30 to 50 cc syringe. This procedure frequently results in a "dry tap" due to the increase in marrow reticulin which is associated with progressive hairy cell leukemia.

Bone marrow biopsy specimens were removed using a Jamshidi biopsy needle which removes a bone cylinder, usually at least 10 mm in length and 3 mm in width.

17.1.2.2. Preparation of Specimens for Microscopic Evaluation

Aspirate specimens were smeared onto a glass slide, dried, stained with Wright's stain and coverslipped.

Biopsy specimens were placed in 10% neutral buffered formalin solution and transported to the surgical pathology laboratory where they were placed in tissue cassettes and fixed for an additional period of time (usually at least one hour) to ensure adequate fixation. The specimens were then decalcified in formic acid and loaded onto an automated tissue processor by which means the biopsies were dehydrated in the process of passing through a series of ethanol solutions of increasing concentration. After dehydration, biopsies were passed through zylene, and infiltrated with paraffin. Histologic sections were prepared by cutting the paraffin-embedded tissues with a microtome. Sections were mounted on glass slides, stained with hematoxylin and eosin (H & E) stain and coverslipped.

17.1.2.3. Light Microscopic Evaluation of Bone Marrow Specimens

The bone marrow slide preparations were interpreted by viewing them through a standard light microscope at 40×, 100× and 400× magnifications. Adequacy of the specimen was a subjective determination. An adequate aspirate sample included bone and bone marrow fragments. Adequacy of the biopsy sample was based on size, representation (not superficial), and absence of marked distortion.

The PERCENT CELLULARITY of the bone marrow was determined based on an examination of the bone marrow biopsy preparation. Cellularity is the estimated ratio of the area occupied by bone marrow cells to that occupied by marrow fat. The normal range is from 25-50 percent, depending on the age of the patient. The cellularity can vary and is reported as an estimate of average cellularity (%) of the bone marrow biopsy specimen.

A differential count of hairy cell and non-hairy cell elements was performed on the aspirate sample, if an adequate sample was obtained. The count was based on the examination of 100 cells at high power. The PERCENTAGE HAIRY CELLS was calculated from the hairy cell count divided by 100. Non-leukemic (generally normal) bone marrow cells were also expressed as a percentage of bone marrow cells present, in the case of erythroid and granulocytic cells, and as either normal/increased/decreased or 1+, 2+, or 3+, in the case of megakaryocytic cells.

If the aspiration procedure had been unsuccessful, an estimate of the % hairy cells was performed using the bone marrow biopsy preparation. The estimate was based on the examination of one high power field.

An accurate estimate of the extent of leukemic infiltration of the bone marrow was determined by deriving a LEUKEMIC INDEX as follows:

$$\text{LEUKEMIC INDEX} = \% \text{ CELLULARITY} \times \% \text{ HAIRY CELLS}$$

17.1.2.4. Sensitivity and Specificity of the Procedure

Recognition of a leukemic cell population having the characteristic features of hairy cell leukemia established the presence of the disease. Hairy cells, when present in sufficient number, are easily recognized and distinguished from the cells of other chronic lymphoproliferative disorders that may be mistaken for HCL. Hairy cells have distinctive, bland nuclei of strikingly uniform size and shape with fine, evenly dispersed chromatin. The cytoplasm is moderate (greater than that of lymphocytes), notably constant in amount, and usually has a clearing artifact in routinely processed histologic slides. The cell membrane is distinct. The combination of highly characteristic nuclear and cytoplasmic features makes the cellular proliferation of HCL easily recognizable and readily distinguishable from other neoplastic cellular proliferations.

Diagnosis is easiest when neoplastic cells are present in large numbers and when normal marrow cellular elements are substantially decreased in number. Marrow involvement by HCL is also readily evident in hypocellular marrows, when the percentage of hairy cells relative to normal bone marrow elements is high. The detection of residual HCL can be difficult in hypercellular marrows of normal or increased cellularity, where the percentage of leukemic cells is low (less than 10%) and the percentage of normal bone marrow elements relative to leukemic cells is high.

17.1.2.5. Criteria for Response to Treatment with Alpha-interferon

The following critera were employed as a basis for determining the extent of a patient's response to treatment with alpha-interferon:

Complete Remission

An absence of hairy cells from peripheral blood, bone marrow aspirate, and bone marrow biopsy specimens on at least two consecutive occasions and restoration of the hemoglobin level to $\geq 12$ g/dl, the absolute granulocyte count to $\geq 1,500/\mu l$ and the platelet count to $\geq 100,000/\mu l$.

Partial Remission

A decrease in bone marrow hairy cell leukemic infiltration (leukemic or hairy cell index) by $\geq 50\%$ from pretreatment values and restoration of peripheral blood values as indicated above (under complete response).

Minor Response

Restoration of one or more abnormal hematologic indexes alone, or, a bone marrow remission without recovery of all hematologic indexes.

Relapse

Appearance of new or worsening of pre-existent abnormalities of peripheral blood, bone marrow or physical examination.

No Change

No change in any pre-existent abnormality of peripheral blood, bone marrow or physical examination.

17.1.2.6. Definitions of Treatment Phase

Treatment phases were defined as follows:

Pre-treatment

Refers to active disease status prior to first administration of alpha-interferon. Patients may have undergone prior splenectomy and/or chemotherapy.

Induction

Refers to initial course of treatment with 3,000,000 IU recombinant alpha-interferon daily (intramuscular or subcutaneous administration) for 6 months.

Maintenance

Refers to the continuation of alpha-interferon therapy, three times per week for 6 to 24 months.

Restart

Refers to reinitiation of alpha-interferon therapy on a maintenance dose for an indefinite period of time.

Subsequent

Refers to subsequent (post-interferon) treatment with another systemic therapeutic agent (deoxycoformycin or Cantell interferon).

Observation

Refers to the off-treatment, clinical follow-up phase.

17.2. Clinical Trial Design

This was a retrospective evaluation of a series of 81 patients with a diagnosis of hairy cell leukemia who were treated with alpha-interferon for the management of their disease at M. D. Anderson Hospital and Tumor Institute, Houston, Tex. These patients were monitored serially over a median follow-up interval of 31 months, with bone marrow biopsies (n=326), bone marrow aspirates (n=342), and hematologic values (n=371) to evaluate bone marrow leukemic infiltration during the induction, maintenance, and observation phases of treatment (refer to Sections 17.1.2.5 and 17.1.2.6 for definitions of treatment phase and response to treatment).

Data for statistical evaluation was based on the existence of a serum IL2R value and accompanying bone marrow biopsy and peripheral blood specimens.

All serum samples (n=379) were analyzed using the CELLFREE® IL2R Test Kit (T Cell Sciences, Inc., Cambridge, Mass.; see Section 16, supra). All bone marrow biopsy measurements were based on prior evaluations of specimens obtained, processed and interpreted using the bone marrow biopsy/histopathology procedure described supra.

The extent of hairy cell infiltration of the bone marrow, based on CELLFREE® IL2R Test Kit measurements, was expressed as units of soluble IL2R per milliliter of serum. The extent of hairy cell infiltration in biopsy tissue sections was expressed as a bone marrow Leukemic Index (% cellularity × % hairy cells of a representative high power field). Dividing this value by 100 provides a PERCENT HAIRY CELL INDEX.

17.3. Results

17.3.1. Correlations Between Serum IL2R and Leukemic Indices

Serum IL2R correlated strongly with the hairy cell Leukemic Index for observations off and on treatment. Table XIII below presents the results of the correlations for each of the study observation phases. Highly significant ($p<0.0001$) correlations were seen for the maintenance and observation phases (refer also to scatterplots in FIGS. 16, 17).

TABLE XIII

CORRELATIONS (R) FOR ABSOLUTE SERUM IL2R LEVELS AND BONE MARROW LEUKEMIC INDEX[1]

| Study Phase | Correlation[2] |
|---|---|
| On treatment: | |
| Induction | 0.19 |
| Maintenance | 0.72**** |
| Restart | 0.62** |
| Off treatment: | |
| Pretreatment | 0.47** |
| Observation | 0.68**** |

[1]Bone marrow leukemic index: % cellularity × % hairy cells
[2]Pearson product moment correlations; statistical significance key:
**$p < 0.01$
***$p < 0.001$
****$p < 0.0001$ Serum IL2R did not correlate with the Leukemic Index during the induction phase. During this period of high dose alpha-interferon therapy, the bone marrow is responding to treatment, as evidenced by a rapid improvement in hematologic indices. Local variations in the extent of hairy cell infiltration occuring during induction could result in biopsy-based measurements which are not representative of overall bone marrow tumor burden. The CELLFREE® IL2R Test Kit measures a disseminated hairy cell marker, serum IL2R. Its performance, therefore, is not affected by local variations in hairy cell infiltration of the bone marrow.

17.3.2. Serum IL2R Expression: Hairy Cell Leukemia and Blood Donor Sera

Serum IL2R was expressed by every one of the 81 study patients. The mean pretreatment level was 33,058 U/ml, with all pretreatment levels above 2,000 U/ml among 43 pretreatment serum samples. In contrast, the mean serum IL2R value was 421 U/ml for 82 normal control serum samples, obtained from blood donors age- and sex-matched to the hairy cell patient population. None of the values in the normal group exceeded 900 U/ml.

17.3.3. Association between Serum IL2R and Bone Marrow Biopsy Leukemic Index For each of the treatment phases, mean serum IL2R was lowest for the subgroup with a 0% Leukemic Index (complete remission) and highest for the subgroup with a >20% Leukemic Index (minor response; $p<0.0001$, nonparametric rank test). Mean serum IL2R levels were significantly lower for on-treatment intervals, when patients were receiving disease directed therapy, than when the patients were off therapy.

17.3.4. Association between Serum IL2R and Major Clinical Response Outcomes

Response outcomes were based on the bone marrow Leukemic Index and hematologic values. Mean serum IL2R levels were lowest for patients with complete responses, higher for partial responses, and highest for minor responses (Table XIV).

TABLE XIV

MEAN SERUM IL2R VALUES ACCORDING TO TREATMENT PHASE AND TREATMENT RESPONSE CATEGORY

| Treatment Phase and Response Categories | Leukemic Index (Range) | Mean[1] IL2R Value (U/ml) |
|---|---|---|
| Pretreatment[2] | 0 to 95% | 33,000 (43)[3] |
| On treatment (alpha-interferon): | | |
| Complete response | 0% | 1,500 (50) |
| Partial response | 1 to 19% | 5,000 (83) |
| Minor response | >20% | 10,000 (49) |
| Off treatment (observation): | | |
| Complete response | 0% | 1,800 (25) |
| Partial response | 1 to 19% | 7,600 (36) |
| Minor response | >20% | 20,000 (64) |

[1]Mean value rounded off to the nearest thousand
[2]Hairy cell leukemia patients with progressive disease, sample obtained within 8 weeks prior to initiating alpha-interferon therapy
[3]Number of serum samples evaluated The association between serum IL2R levels and response to alpha-interferon treatment may also be illustrated by calculating the percentage reduction in serum IL2R levels for each response category (Table XV).

TABLE XV

MEAN PERCENT REDUCTIONS IN SERUM IL2R FROM PRETREATMENT LEVELS

| Treatment Group | Response Category | | |
|---|---|---|---|
| | Complete | Partial | Minor |
| On alpha-interferon | 94% | 66% | 66% |
| Off alpha-interferon | 93% | 69% | 12% |

Sera from on treatment patients in the complete response group showed the largest percentage decrease: a 94% drop from pretreatment serum IL2R values. Sera from patients categorized as remaining in complete response while off treatment still showed a large percentage decrease (93%) from pretreatment levels of serum IL2R.

17.4. Conclusions

The quantitative determination of serum IL2R levels can be used to measure the extent of bone marrow leukemic infiltration in hairy cell leukemia patients. Serum IL2R is a soluble marker for the hairy cell.

The results of this trial demonstrate that all 81 of the hairy cell leukemia patients tested expressed serum IL2R, and that all 43 patients with pre-treatment sera showed serum IL2R levels which were elevated beyond the normal range. This finding suggests a low false negative rate for the CELLFREE ® IL2R Test Kit in previously diagnosed patients IL2R based measurements of bone marrow hairy cell infiltration correlated significantly with the biopsy-based, bone marrow Leukemic Index.

In summary, the clinical data demonstrate that measurements of serum IL2R can be relied on as indicators of the extent of hairy cell infiltration of the bone marrow, in hairy cell leukemia patients.

18. SOLUBLE IL-1 BINDING PROTEIN DETECTION IN PATIENT SERUM

The examples described below demonstrate that elevated levels of IL-1 binding protein can be detected in leukemia patient samples using the assays of the present invention.

18.1. Monoclonal Antibodies

A murine anti-IL-1 binding protein mAb was generated according to standard techniques (Kung, P. C., et al., 1979, *Science* 206:347-349) using spleen cells from mice immunized with IL-1 binding protein purified by published procedures (Muchmore, A. V. and Decker, J. M., 1985, *Science* 229:479-481). Rabbit polyclonal antibody (hetero-serum) directed against the IL-1 binding protein was generated by immunizing a rabbit with purified uromodulin as previously described (id.)

18.2. Soluble IL-1 Binding Protein Assay

Soluble IL-1 receptor was detected in samples using the procedure outlined below:

(a) Polystyrene microtiter wells (Flow Laboratory) were coated overnight at 4° C. with 100 μl of a murine anti-IL-1 binding protein monoclonal antibody (2.5 μg/ml) in PBS.
(b) Coating solution was discarded and wells were blocked for 1-2 hours at room temperature with 300 μl of 1% BSA in Tris-Tween Buffer.
(c) Wells were washed 3 times with Tris washing solution.
(d) 50 μl sample was added per well followed by 100 μl diluent containing 50% fetal calf serum in Tris-buffered saline and 0.1% NP-40. Wells were incubated 2 hours at 37° C.
(e) Wells were washed 3 times with Tris washing solution.
(f) 100 μl of rabbit anti-IL-1 binding protein polyclonal antibody (hetero-serum) was added at a titrated dilution of 1/1000 with Tris-buffered saline.
(g) Incubation for 2 hours at 37° C.
(h) Wells were washed 3 times with Tris washing solution.
(i) 100 μl of goat anti-rabbit IgG, horseradish peroxidase conjugate (Tago, Calif.) at 1/2000 dilution was added to each well.
(j) Incubation for 1 hour at 37° C.
(k) Wells were washed 4 times with Tris washing solution.
(l) 100 μl of 0.2% o-phenylenediamine (OPD) and 0.015% of $H_2O_2$ in citrate-phosphate buffer was added per well. Plates were incubated for 30 minutes at room temperature.
(m) 50 μl of 2N $H_2SO_4$ was added to each well and the absorbance of each well was measured at 490 nm on a microtiter plate reader.

18.3. Results

As shown in Table XVI, plasma isolated from normal healthy donors indicated low levels of soluble IL-1 binding protein. However, the plasma levels of soluble IL-1 binding protein were highly elevated in some leukemia patients. Urine samples obtained from patients also contained highly elevated and widely variable levels of soluble IL-1 binding protein.

TABLE XVI

SOLUBLE IL-1 BINDING PROTEIN
LEVEL IN PATIENT SAMPLES (OPTICAL DENSITY)

| | Plasma Samples | | |
|---|---|---|---|
| | Healthy Donor | Leukemia Patients | Urine Samples |
| 1 | 0.007 | 0.593 | 0.767 |
| 2 | 0.008 | 0.109 | 0.741 |
| 3 | 0.039 | 0.244 | 1.612 |
| 4 | 0.037 | 0.095 | 0.495 |
| 5 | 0.003 | 0.060 | 0.336 |
| 6 | 0.026 | 0.048 | 0.284 |
| 7 | 0.007 | 0.060 | 1.473 |

19. SOLUBLE CD8 DETECTION IN PATIENTS

The following sections describe antibodies and assays that can be used to detect soluble CD8 antigen in patients.

19.1. Monoclonal Antibodies

Anti-CD8 monoclonal antibody 5F4 was generated according to Reinherz et al. (1979, Proc. Natl. Acad. Sci. U.S.A. 76:4061–4065) by immunizing BALB/c mice with a human T cell line (Jurkat). Monoclonal antibody 5F4 recognizes an epitope on CD8 that is different from the epitope on CD8 which is recognized by mAb OKT8.

19.2. Soluble CD8 Assay

Soluble CD8 was detected in samples using the procedure outlined below: (a) Polystyrene microtiter wells (Flow Laboratory) were coated overnight at 4° C. with 100 µl of an anti-CD8 murine monoclonal antibody (2.5 ug/ml) of mAb OKT8 (Ortho Diagnostics, Raritan, N.J.) in PBS.
- (b) Coating solution was discarded and wells were blocked for 1–2 hours at room temperature with 300 µl of 1% BSA in Tris-buffered saline containing 25 mM Tris pH 7.4 in 0.05% Tween 20 and 0.15M sodium chloride (NaCl).
- (c) Wells were washed 3 times with 10 mM Tris, 0.05% Tween 20, pH 8.0 (Tris washing solution).
- (d) 10 µl sample was added per well, followed by 90 µl diluent containing 50% FCS in Tris-buffered saline and 0.4% N-40 (Sigma). Wells were incubated 2 hours at 37° C.
- (e) Wells were washed 3 times with Tris washing solution.
- (f) 100 µl of horseradish peroxidase conjugated anti-CD8 murine monoclonal antibody (0.2 µg/ml mAb 5F4) in 50% FCS, 25 mM Tris pH 7.4, 0.15M NaCl and 0.1% NP-40 was added to each well and incubated 2 hours at 37° C.
- (g) Wells were washed 4 times with Tris washing solution.
- (h) 100 µl of 0.2% o-phenylenediamine (OPD) and 0.015% of $H_2O_2$ in citrate-phosphate buffer was added per well. Plates were incubated for 30 minutes at room temperature.
- (i) 50 µl of 2N $H_2SO_4$ was added to each well and the absorbance of each well was measured at 490 nm in a microtiter plate reader.

19.3. CD8 Control Standards

The supernatant of a tissue culture line (Jurkat) was used as the standard. The measured value was assigned a reference number of 2000 units/ml. The culture supernatant consisted of RPMI-1640 medium containing 10% FCS and 100 units of penicillin-streptomycin.

9.4. Enzyme Immunoassay for the Quantitation of Cell-free Human T Cell CD8-like Molecule Using two monoclonal antibodies directed against distinct epitopes on the CD8 antigen, a human suppressor/cytotoxic T cell marker, we have developed a sensitive quantitative enzyme immunoassay for measuring the cell free form of a human T cell CD8-like antigen. Elevated levels of this antigen are observed in a number of diseases and conditions including certain leukemias, allograft transplantation, and autoimmune diseases such as rheumatoid arthritis and lupus. In longitudinal patient studies, increases in the serum level of cell-free CD8 are seen in a different time frame when compared to the expression of soluble interleukin-2 receptor (IL2R). In certain instances, elevations of cell-free CD8-like molecules are preceded by several days with elevations in serum IL2R levels. Increased levels of this cell-free CD8-like molecule may indicate the involvement of significant numbers of suppressor/cytotoxic T cells with a specific pathological event, distinct from immune activation as measured by a rise in cell-free IL2R. The presence of cell-bound CD8 and IL2R molecules is typically measured by cell surface staining. These cell-free assays may provide a more thorough understanding of certain immunological disorders.

The assay used for CD8 was a sandwich enzyme immunoassay, as described in Section 19.2, supra. An anti-CD8 mAb (mAb 1) was coated onto a solid substratum, e.g. microtiter wells. CD8 in the sample binds to the antibody-coated well; unreacted sample components are washed away. An enzyme-conjugated, second anti-CD8 mAb (mAb 2), recognizing a different epitope than that of mAb 1, binds to the CD8 antigen captured by the first antibody and completes the sandwich. Unbound mAb 2 was removed by washing. A substrate solution was added to the wells, and a colored product formed in proportion to the amount of CD8 present in the sample. The reaction was terminated by stop solution and the absorbance was measured. A standard curve is prepared from CD8 standards (See Section 19.3, supra). Unknown values were determined from the standard curve.

19.4.1. Evaluation of Anti-CD8 Monoclonal Antibodies as a Capture Antibody

Various monoclonal antibodies (mAbs) directed against the CD8 antigen were tested for their suitability as a capture antibody in an enzyme immunoassay employing anti-CD8 mAb 5F4 as detection antibody (mAb 2).

Plates (Flow microstrips, Flow Laboratory, McClean, Va.) were coated overnight with 2.5 µg/ml of capture antibody. Non-reactive sites were blocked the next day with a solution containing 1% BSA in 0.15M NaCl, 0.025M Tris-Cl (pH 7.4), 0.01% thimerosal, 0.05% Tween 20. 100 µl sample was added, consisting of CD8-containing Jurkat cell supernatant, diluted 1:4 in 25% fetal calf serum, 0.25% Nonidet P-40 (NP-40) in Tris-buffered saline. After incubation for 90 minutes at 37° C., the plates were washed with 10 mM Tris, 0.05% Tween 20, pH 8.0. 100 µl of horseradish peroxidase (HRP)-conjugated mAb 5F4 (at 1:5000 dilution of a 1 mg/ml stock) in 25% fetal calf serum, 0.25% NP-40 in Tris-buffered saline was added. Plates were incubated for 90 minutes at 37° C. and washed as above. 100 µl of 0.2% o-phenylenediamine was added in 0.015% $H_2O_2$, and incubated for 30 minutes at room temperature, after which absorbance was read at 450 nm. Results are as shown in Table XVII.

TABLE XVII

EVALUATION OF ANTI-CD8 MONOCLONAL ANTIBODIES AS A CAPTURE ANTIBODY[1]

| Capture Antibody | Ability to Compete Binding of mAb 5F4 to CD8 | $OD_{450}$[2] |
|---|---|---|
| B98.1.1 | Partial | 0.028 |
| B116.1.1 | Yes | 0.027 |
| B99.1.1 | No | 0.039 |
| OKT8 | No | 0.413 |
| 4C9 | No | 1.106 |
| 5F4 | Yes | 0.042 |
| 62EC[3] (control) | Yes | 0.042 |

[1]With HRP-conjugated mAb 5F4 as detection antibody
[2]Readings at or below 0.042 (negative control) are considered negative
[3]Negative control mAb, directed against Keyhole limpet hemocyanin (Pacific Biolabs, CA)

The results of binding competition assays to mAb 5F4 are also shown in Table XVII. These assays were carried out using the same protocol described supra, except that the capture antibody was OKT8 and the detection antibody was a mixture of 50 µl competing antibody (1 µg/ml) plus 50 µl HRP-conjugated mAb 5F4 (at 1:2500 dilution of a 1 mg/ml stock).

As shown in Table XVII, the seven mAbs tested as capture antibodies can be classified into three groups, based on their ability to competitively inhibit binding of mAb 5F4 to CD8 antigen. As expected, use of the 5F4 mAb as both capture and detection antibody does not work (since capture antibody 5F4 competes out detection antibody 5F4 binding). Surprisingly, among the group of mAbs which did not competitively inhibit binding of 5F4 to CD8, 4C9 worked best, giving the highest assay results, followed by OKT8, whereas B99.1.1 was negative. Thus, it is not obvious, even based upon competition ability, to predict which anti-CD8 monoclonal antibodies will work in a sandwich immunoassay.

A comparison of the serum CD8 levels measured by use of mAb OKT8 versus mAb 4C9 as capture antibody was also done. mAb 5F4 was used as a detection antibody. The results, shown in Table XVIII, demonstrate a greater CD8 detection level using 4C9 as capture antibody in the vast majority of cases.

TABLE XVIII

COMPARISON OF CD8 LEVELS USING TWO DIFFERENT ANTI-CD8 CAPTURE ANTIBODIES[1]

| PATIENT GROUP | U/ml MEASURED USING OKT8 CAPTURE | MEASURED USING 4C9 CAPTURE |
|---|---|---|
| Normal | 96 | 143 |
|  | 122 | 207 |
|  | 211 | 211 |
|  | 52 | 72 |
|  | 146 | 209 |
|  | 59 | 147 |
|  | 20 | 72 |
|  | 14 | 65 |
|  | 76 | 270 |
|  | 33 | 270 |
|  | 52 | 261 |
|  | 76 | 329 |
|  | 63 | 394 |
|  | 193 | 724 |
|  | 14 | 96 |
|  | 91 | 252 |
|  | 33 | 188 |
|  | 269 | 858 |
|  | 57 | 292 |
|  | 22 | 226 |
| Renal Transplant Patients | 237 | 721 |
|  | 229 | 620 |
|  | 393 | 1249 |
|  | 303 | 687 |
|  | 231 | 613 |
|  | 488 | 1464 |
|  | 824 | 1665 |
|  | 351 | 1176 |
|  | 381 | 1603 |
|  | 432 | 1002 |
|  | 202 | 171 |
|  | 198 | 131 |
|  | 455 | 248 |
|  | 502 | 361 |
|  | 98 | 110 |
|  | 133 | 190 |
|  | 324 | 377 |
|  | 144 | 319 |

[1]With anti-CD8 mAb 5F4 as detection antibody

20. SERUM CD8 LEVELS IN EVALUATION OF DISEASES AND DISORDERS

A number of diseases and disorders can be staged or diagnosed by measuring serum soluble CD8 levels in patients. Examples are described in the subsections below.

20.1. Differential Diagnosis of Rheumatoid Arthritis

Using the CD8 sandwich enzyme immunoassay described above one can distinguish rheumatoid arthritis from other joint diseases (FIG. 18). The results shown in FIG. 18 are based on the level of serum or synovial fluid CD8 concentration, measured using mAb 4C9 as capture antibody, and mAb 5F4 as detection antibody.

20.2. Serum CD8 Levels in a Renal Allograft Recipient

Patient A was the recipient of a HLA nonidentical renal allograft from cadaver. The patient was transplanted on May 23, and maintained on cyclosporin A (CsA). From May 23 through May 31, the patient experienced CsA toxicity and some early rejection. On June 28, a rejection episode was diagnosed (based on a rise in creatinine level, and the patient was administered OKT3 mAb, at 5 mg doses intravenously four times a day, through Jul. 7. On Jul. 8, the creatinine level had decreased, and the patient had entered the process of recovery. On Jul. 18, there was another rise in creatinine level that was treated by administration of prednisone, which resulted in a decrease in the creatinine level until Aug. 26, at which time another dose of prednisone was administered.

IL2R and CD8 levels in the patient serum were measured at suitable intervals from May 23 (transplant date) on, and are shown in FIG. 19 which shows a peak in serum CD8 levels after a rejection episode (but not after an episode of CsA toxicity). This is suggestive of a role for measurement of serum CD8 levels in the monitoring and differential diagnosis of renal transplant.

20.3 Serum CD8 Levels in Children with Non-Hodgkin's Lymphoma

CD8 levels were measured in the serum of the children with non-Hodgkin's lymphoma (NHL) or B-cell acute lymphoblastic leukemia (ALL), that were used in the study of IL2R serum levels, described in Section 9, supra.

The enzyme sandwich immunoassay, described above was used, with anti-CD8 mAbs 4C9 and 5F4 as the capture and detection antibodies, respectively. The results shown in FIG. 20 demonstrate that a detectable increase in the level of serum CD8 antigen in patients appears to be related to advanced disease and a poor outcome.

20.4. CD8 Levels in Infectious Disease

The enzyme sandwich immunoassay, as described in Section 19.2., was used to measure CD8 levels in the serum of patients with an infectious disease. Anti-CD8 mAbs 4C9 and 5F4 were used as the capture and detection antibodies, respectively. The results, shown in FIG. 21, demonstrate an elevated level of the CD8 antigen, particularly in patients with Hepatitis B, Epstein Barr virus, AIDS related complex, and AIDS disorders.

20.5. Soluble CD8 Levels as a Measure of the Immune Response to Disease

In the example herein (Carrabis, S., et al., 9th Ann. European Immunology Mtg., Sep. 14-17, 1988, Rome Italy, poster presentation), we describe the results obtained using a sandwich enzyme immunoassay (CELL-FREE® T8 Test Kit, T Cell Sciences, Inc., Cambridge, Mass.) to measure soluble CD8 in cell culture supernatant and in patient sera.

The assay used has a range of 0-2,000 U CD8/ml of fluid and a sensitivity of 50 U/ml. No interference was seen in serum samples exhibiting high levels of protein, lipid, bilirubin, or hemoglobin.

The levels of released T8/CD8 measured by the ELISA assay were shown to correlate with the level of activation of CD8+ cells in vitro and in patients with EBV+ mononucleosis, a highly disseminated disease. The normal range of released T8/CD8, determined in 196 healthy individuals, Was determined to be 138-533 U/ml.

The material reactive in the CD8 1 Immunoassay was shown to be specifically released by CD8+ cell lines. The form of CD8 found in culture supernatant appeared to be a 52 kD homodimer, which is smaller than the 64 kD membrane bound molecule.

Levels of soluble CD8 were proportional to the degree of cellular activation, as measured by dual color immunofluorescence using fluorescent-tagged anti-CD8 and anti-HLA-DR antibodies, in PHA and anti-T3 antibody-stimulated peripheral blood mononuclear cell cultures.

In EBV-induced mononucleosis, changes in the levels of soluble CD8 paralleled changes in the proportion of peripheral T cells that were CD8+/HLA-DR+.

21. MOLECULAR CHARACTERIZATION OF THE SOLUBLE CD8 ANTIGEN

Jurkat cell supernatants and cell lysates were immunoprecipitated with anti-CD8 mAbs, in order to study the molecular nature of the CD8 antigen in its soluble and cell-associated forms that is recognized by the antibodies.

21.1. Methods $5 \times 10^6$ Jurkat cells in a Falcon T25 flask were pulse-labeled with 2 mCi $^{35}$S-methionine in met$^-$ RPMI 1640 medium. After six hours, the media was removed, cells were washed with the complete RPMI 1640 media, and cells were incubated in complete RPMI 1640 media for 16 hours before harvesting. Cells were pelleted by centrifugation. Supernatant samples were prepared by centrifuging cell culture supernatant at 20,000× g for 30 minutes, and filtering the supernatant through a 0.22 μm Millipore ™ filter. Cell lysates were prepared by resuspending $5 \times 10^6$ cells in 1 ml lysis buffer: 0.15M NaCl, 25 mM Tris-Cl (pH 8.0), 1 mM $MgCl_2$, 1% Nonidet P-40 (NP-40, polyoxyethylene (9) p-tert-octylphenol), 1 mM phenylmethylsulfonylfluoride (PMSF), 0.2 mg/ml alpha-2-macroglobulin, 10 mM iodoacetamide, 0.1 mg/ml ovomucoid trypsin inhibitor. Cells plus lysis buffer were allowed to stand for 0.5 hour at 4° C., centrifuged at 20,000× g for 30 minutes, and the supernatant (cell lysate sample) removed for immunoprecipitation.

Culture supernatants and cell lysates were purified by immunoprecipitating with anti-CD8 mAbs 5F4, 4C9, and OKT8. The immunoprecipitation was accomplished in two steps: a nonspecific adsorption step, and a specific binding step. To remove non-specifically bound material, the lysate or cell supernatant sample was incubated with 5% volume of packed Sepharose coupled to mouse immunoglobulin G (Affigel, Biorad, Richmond, Calif.) for 3 hours on a rocker at room temperature. After spinning out the Sepharose, the supernatant (either 1 ml culture supernatant sample or 0.2 ml lysate sample) was incubated with 10 μl packed Sepharose coupled to either mAb OKT8 or 4C9 or 5F4, or control mAb OKT3. Samples were agitated at room temperature for two hours, and then washed ten times with 1.5 ml phosphate-buffered saline. Samples were eluted into 200 μl 50 mM diethylamine, 0.15M NaCl, pH 11.0. The eluate was diluted with an equal volume of electrophoresis sample buffer. One-half of each eluate was then reduced by addition of dithiothreitol (DTT) to a concentration of 10 mM; one-half of each eluate was left unreduced. Samples were boiled and loaded onto a 10-20% sodium dodecyl sulfate-polyacrylamide gel. Gels were dried and exposed for autoradiography.

21.2. Anti-CD8Mabs Recognize a Soluble CD8 Antigen of 52-55 Kilodaltons

The nonreduced cell lysate immunoprecipitates contained predominantly a 52-55 kd form. This is somewhat smaller than the 66 kd cell surface form of the CD8 antigen previously reported (Fujimoto, J., et al., 1983, *J. Exp. Med.* 159: 752-766). Surprisingly, the nonreduced cell culture supernatant immunoprecipitate contained only the 52-55 kd dimeric form of the CD8 antigen. This is in contrast to the results of Fujimoto et al., who detected only a 27 kd monomer form under either reducing or nonreducing conditions, of the soluble CD8 antigen in sandwich immunoassays (Fujimoto et al., supra). In the reduced supernatant immunoprecipitate described herein, the 27 kd CD8 monomer was observed, confirming the identity of the 52-55 kd soluble form as a dimer consisting of monomers each having a molecular weight of 27 kd as determined by SDS polyacrylamide gel electrophoresis. Thus, the anti-CD8 mAbs recognized a dimeric 52-55 kd form of the CD8 antigen as both a soluble and a cell-associated molecule.

When a reducing agent, DTT, was included in a sandwich enzyme immunoassay for CD8 antigen in supernatant samples, no binding was observed. Thus, reduction of the soluble dimeric form to monomer abolished the ability of the anti-CD8 mAbs to bind the soluble antigen, confirming that these anti-CD8 mAbs may bind only to a soluble CD8 dimer.

22. SOLUBLE CD2 DETECTION

The supernatants of various cultured cells were assayed for soluble CD2 using two monoclonal antibodies which define different epitopes of the CD2 (T11) molecule. Samples were assayed using a sandwich immunoassay format as previously described, in which monoclonal antibodies B67.6.1.1. and B67.1.1.1. (Perussia, B., et al., 1983 *J. Immunol.* 130:2142) were used as the capture and detection antibodies, respectively, and vice versa.

A released form of CD2 was detected in supernatants of the following cultured cells which are CD2 surface positive: HPB-ALL, Jurkat, CEM and MOLT-4. By contrast, soluble CD2 was not detected in the supernatants of cultured cells which are CD2 surface negative such as DAUDI. Soluble CD2 was also not detected in the supernatant of cultured PEER cells, a T cell line which is weakly CD2 surface positive.

23. SOLUBLE CD4 ANTIGEN

In the examples detailed herein, a sandwich immunoassay is described for the preferential detection of the soluble form of CD4 antigen relative to the cell-surface form of CD4 antigen.

23.1. Materials and Methods

23.1.1. Antibodies

Antibody Leu3a, biotin or FITC labeled, was purchased from Becton Dickinson, Mountain View, Calif. Antibodies OKT4 and OKT4A were obtained from Ortho Diagnostics, Raritan, N.J. Antibody IOT4 was obtained from Immunotech, Cedex, France and further purified by ammonium sulfate precipitation. Antibodies B67.2 and B66.1 were from G. Trincherie, Wistar Institute. Antibody 3G2 was from Sanchex Madrid, Madrid, Spain. Antibody R2B7 was obtained from a fusion of rat spleen cells (carried out according to standard procedures), from an animal immunized with whole human peripheral blood lymphocytes, with mouse SP2/0 myeloma cells. Clone R2B7 was selected from this fusion based on its ability to stain populations of peripheral blood lymphocytes identical to these identified by OKT4.

Antibodies were purified either by ammonium sulfate precipitation or by protein A sepharose using the Biorad MPAS buffer system (BioRad Corporation, Richmond, Calif.). Horseradish peroxidase (HRP) conjugates were prepared essentially according to the method of Wilson and Nakane (1978, in *Immunofluorescence and Related Techniques*, Knapp, W., et al., eds. Elsevier, p. 215) using a molar HRP to antibody ratio of four.

Antibodies generated from a fusion of mice immunized with intact T cells (Jurkat) were screened for their ability to substitute for Leu3A in the assay as follows: Plates were coated with R2B7 as described, blocked and incubated with recombinant soluble CD4 for 2 hours at 37° C. Plates were washed and 50 μl of each hybridoma supernatant at 1-10 μg/ml were added followed by 50 μl of biotinyl Leu3A. Following a 2 hour incubation, plates were washed and 100 μl of streptavidin peroxidase (0.5 μg/ml) was added for 30 minutes. Plates were washed and developed as described below.

23.1.2. Immunoassay Protocols

23.1.2.1. Initial Assay

The enzyme immunoassay for the CD4 antigen was based on the sandwich immunoassay technique. Briefly, each well of a microtiter plate (Nunc, certified high binding) was coated overnight at 4° C. with a solution of murine monoclonal anti-human CD4 antibody in PBS, pH 7.4. Any remaining protein-binding sites on the microtiter wells were then blocked for two hours at 37° C. with 300 μl per well of a solution of BSA (1%) (Kirkegard and Perry Laboratories, Md.) and Tween 20 (0.05%) (Zymed Laboratories, South San Francisco, Calif.) in phosphate buffered saline (PBS), pH 7.4. The wells were then washed three times with 350 μl per well of PBS (pH 7.4) with 0.05% Tween 20. Following the final wash step, the wash solution was aspirated from the wells and 50 μl of a sample diluent consisting of 0.15M NaCl, 25 mM Tris (pH 7.4) supplemented with bovine proteins was added to each well. Fifty μl of standard or sample were added to the appropriate wells in duplicate. The solution in the wells was mixed thoroughly by gently tapping the side of the plate for fifteen seconds. The plate was then sealed and incubated at 37° C. for 2 hours. At the end of this incubation period, the solution was aspirated from the plate and each well was washed three times with 350 μl of PBS/Tween 20 as above. One hundred μl of horseradish peroxidase (HRP) conjugated murine monoclonal anti-human CD4 antibody was added to each well of the microtiter plate, and the plate was again incubated at 37° C. for 2 hours, as above. At the end of this incubation, the wells were once again washed three times with PBS/Tween 20 as above. One hundred μl of o-phenylenediamine (0.2%) dissolved in 0.1M sodium citrate buffer, pH 5.5, was then added to each well of the plate and incubated at 24° C.±2° C. for 30 minutes. At the end of this final incubation, 50 μl of 2N $H_2SO_4$ was added to each well to stop the reaction and the absorbance of each well was read at 490 nm.

For assays involving biotinylated antibodies, biotin conjugates were substituted for the HRP antibody conjugate. After the 2 hour incubation, wells were washed and 100 μl of streptavidin horseradish peroxidase (Zymed Laboratories) at 0.5 μg/ml in 1% bovine serum albumin in tris buffered saline was added. Following a 30 minute incubation at 37° C., wells were washed and color developed as described above.

Where indicated, assays were also performed as a single step assay in which conjugated antibody was added at the same time as the sample and incubated for 4 hours at room temperature on a rotating shaker platform, after which washing and color development were performed as described.

23.1.2.2. Optimized Assay

The configuration of the initial assay was modified by optimizing each of the assay reagents. This resulted in an improved sensitivity for the overall assay where much lower levels of soluble CD4 could be reliably and reproducibly detected. The optimized assay configuration is given in Table XIX.

TABLE XIX

COMPARISON OF INITIAL & OPTIMIZED ASSAY CONFIGURATIONS

| INITIAL ASSAY | OPTIMIZED ASSAY |
|---|---|
| Blocking Buffer: | |
| 1% BSA + 0.05% Tween 20 | 0.5% Casein, 0.008% NP-40, 0.005% EDTA |
| Sample Diluent\* | |
| 0.15M NaCl, 25 mM Tris, supplemented with bovine proteins | 0.25% NP-40, supplemented with bovine proteins in PBS |
| Conjugate Diluent\* | |
| 25% FCS in Tris buffered saline + 0.25% NP-40 | 15% FCS, 0.15% NP-40 |

\*Aggregated IgG was added to both the sample diluent and the conjugate diluent to remove any effect of rheumatoid factors in various samples.

Occasionally, it was observed that the presence of rheumatoid factor (RF) in some of the samples led to erroneous determinations of soluble CD4 that appeared as false positives. To remove this effect, aggregated IgG was added to the sample and conjugate diluent buffers. The aggregated IgG was prepared by heating a 100 μg/ml solution of IgG in 100 mM sodium phosphate buffer, 0.9% NaCl, pH 5.56 at 56°-60° C. for 50 minutes, followed by neutralization with dibasic sodium phosphate, 0.9% NaCl, pH 8 to give a final pH of 7.4.

23.1.3. Cell Procedures

For stimulation experiments, peripheral blood mononuclear cells were prepared using Ficoll Hypaque gradients. Cells were put into culture along with phytohemagglutinin (PHA) (0.5 μg/ml) or phorbol myristate acetate (1 ng/ml) and ionophore A2317 (0.1 ng/ml) or OKT3 (anti-T3 monoclonal antibody) (2 μg/ml). Samples were taken daily. For long term cultures of cells from rheumatoid arthritis or lung cancer patients, cells were maintained on IL-2. Cells were removed from culture supernatants by centrifugation followed by filtration through 0.22 μm filters and stored frozen until analysis.

Cell surface phenotyping was performed using a Cytofluorograph II (Ortho Diagnostic System, Westwood, Mass.) and FITC labeled OKT4 or OKT8 (Ortho Diagnostic Systems, Raritan, N.J.).

Recombinant soluble CD4 was obtained from cell culture supernatant of a chinese hamster ovary (CHO) cell line transfected with CD4 truncated at the transmembrane exon (Fisher, R. A., et al., 1988, *Nature* 331:76–78).

23.2. Results

23.2.1. Using Initial Assay Protocol

Table XX shows the initial results of screening serum samples for released CD4 using OKT4 or OKT4A as capture reagent, and Leu3a as a detection reagent.

TABLE XX

CD4 DETECTION\*

| | Capture Antibody: | |
|---|---|---|
| Sample | OKT4 | OKT4A |
| HPB T Cell Lysate | | |
| 5 × 10⁶ cells/ml | 0.895 | 0.139 |
| 2.5 × 10⁶ cells/ml | 0.769 | 0.079 |
| 1.25 × 10⁶ cells/ml | 0.549 | 0.046 |
| **T Cell Leukemia\*\*\* Patient Serum** | | |
| Sample 1184 | 0.000 | 0.000 |
| Sample 1174 | 0.000 | 0.020 |
| Sample 1195 | 0.004 | 0.040 |
| Sample 1147 | 0.004 | 0.000 |

\*Values shown are $OD_{490}$, using the indicated capture antibody and biotinylated Leu3a as detection antibody.
\*\*The indicated numbers of HPB (human leukemia T cell line) cells were lysed in 1 ml detergent buffer.
\*\*\*Serum from patients with acute HTLV I associated T cell leukemia While this assay could detect solubilized CD4 in cell lysates, no detectable soluble CD4 was observed in the sera of patients with HTLV I associated T cell leukemia, which is a disease characterized by an intense activated population of T cells.

Subsequent efforts were focused on determining whether antibodies could be selected which might preferentially recognize a released (soluble) form of the CD4. Recombinant CD4, with the transmembrane and cytoplasmic regions deleted at the gene level, was used as a model antigen. Antibodies were coated onto microtiter wells overnight and blocked as described. Samples containing either buffer, detergent solubilized CD4 from the Jurkat T cell line at two different dilutions, or recombinant CD4 were added, followed by a second incubation with HRP-conjugated antibodies (or biotinylated Leu3a followed by streptavidin HRP). Each antibody was evaluated on both a capture and detection mode with all other antibodies on each of the samples. The results are shown in Tables XXI and XXII.

TABLE XXI

CD4 DETECTION IN CELL LYSATES\*

| Detection Antibody | Capture Antibody | | | | |
|---|---|---|---|---|---|
| | 3G2 | B66.1 | R2B7 | B67.2 | OKT4 |
| 3G2 | 0.204 | 0.227 | 0.154 | 0.242 | >2.00/1.9 |
| B66.1 | 0.053 | 0.064 | 1.420 | 0.053 | >2.00/1.28 |
| R2B7 | 0.230 | >2.0/0.93 | 0.217 | 1.843 | >2.09/>2 |
| B67.2 | 0.027 | 0.030 | 0.110 | 0.008 | 1.50 |
| OKT4 | 0.037 | 0.024 | 0.040 | 0.000 | 0.008 |
| Leu3A | 0.196 | 0.206 | >2.00/1.94 | 0.279 | >2.00/>2 |

\*Cell lysates contained 5 × 10⁶ cells/ml. Values shown are $OD_{490}$. For those antibody pairs where absorbance was >2.0 for 5 × 10⁶ cells/ml lysate, the value for 1 × 10⁶ cells/ml is shown in same box preceded by a slash.

TABLE XXII

RECOMBINANT SOLUBLE CD4 DETECTION

| Detection Antibody\* | Capture Antibody\* | | | | |
|---|---|---|---|---|---|
| | 3G2 | B66.1 | R2B7 | B67.2 | OKT4 |
| 3G2 | 0.002 | 0.003 | 0.074 | 0.000 | 0.230 |
| B66.1 | 0.002 | 0.012 | 0.170 | 0.004 | 0.010 |
| R2B7 | 0.000 | 0.036 | 0.059 | 0.013 | 0.300 |
| B67.2 | 0.000 | 0.000 | 0.008 | 0.000 | 0.009 |
| OKT4 | 0.001 | 0.000 | 0.010 | 0.002 | 0.000 |
| Leu3A | 0.008 | 0.000 | 1.765 | 0.000 | 0.231 |

Values shown are $OD_{490}$.
\*mAb B53.1 was also used, but showed no positive results when used as either capture or detection reagent.

The data presented in Tables XXI and XXII reveals a wide range of assay efficacies for the detection of solubilized cell-surface CD4 antigen (in cell lysate) or recombinant soluble CD4 antigen. Optimal Combinations for detection of recombinant or lysate CD4 antigen are shown in Table XXIII.

TABLE XXIII

OPTIMAL PAIRS OF ANTIBODIES FOR DETECTION OF DETERGENT SOLUBILIZED OR RECOMBINANT CD4

| Capture Antibody | Detection Antibody |
|---|---|
| R2B7 | Leu3A |
| R2B7 | B66.1 |
| B66.1 | R2B7 |
| B67.2 | R2B7 |
| OKT4 | R2B7 |
| OKT4 | B66.1 |
| OKT4 | B67.2 |
| OKT4 | Leu3A |
| OKT4 | 3G2 |

Interestingly, only the combination of R2B7 as a capture antibody with Leu3A as a detection antibody gave signal with the recombinant CD4 substantially equivalent to that seen in lysate, suggesting this pair might preferentially recognize soluble CD4.

Antibodies were generated from a mouse immunized with whole T cells and screened for their ability to replace Leu3a in an assay. 500 hybridoma clones were screened and three clones meeting the above criteria were identified. One of these clones, termed 8F4, showed the ability to block binding of FITC labeled Leu3A to CD4 positive T cell surfaces.

Antibodies 8F4 and R2B7 were evaluated with regard to optimal configuration in the assay. Table XXIV shows that 8F4 used as capture antibody with R2B7 used as detection antibody produced a significantly greater ratio of signal observed using recombinant soluble CD4 to signal observed using detergent solubilized membrane CD4, compared to the ratio of signal observed with R2B7 as a capture antibody and 8F4 as detection.

TABLE XXIV

CD4 DETECTION

| SAMPLE: | 8F4 Capture and R2B7 Detection | R2B7 Capture and 8F4 Detection |
|---|---|---|
| HPB Cell Lysate (cells/ml lysate) | | |
| 2 × 10⁶ | 1.683 | 1.178 |
| 1 × 10⁶ | 1.005 | 0.619 |
| 5 × 10⁵ | 0.583 | 0.370 |
| 2.5 × 10⁵ | 0.274 | 0.172 |
| 1.25 × 10⁵ | 0.135 | 0.090 |
| 6.25 × 10⁴ | 0.067 | 0.045 |
| 0 | 0.014 | 0.013 |
| Recombinant Soluble CD4 Dilutions* | | |
| 1:2 | >2.0 | 1.411 |
| 1:4 | >2.0 | 0.991 |
| 1:8 | >2.0 | 0.666 |
| 1:16 | 1.165 | 0.309 |
| 1:32 | 0.718 | 0.152 |
| 1:64 | 0.382 | 0.074 |
| T Cell Culture Supernatants | | |
| ST16** T cell line | 0.187 | 0.135 |
| 5B4** T4 clone | 0.152 | 0.104 |
| 6D11** T4 clone | 0.171 | 0.120 |
| 5C8** T4 clone | 0.331 | 0.246 |
| TIL** 5C4 T8 clone | 0.037 | 0.019 |

*Ratios represent the dilutions of cell culture supernatant of transfected CHO cells expressing the recombinant
**soluble CD4 antigen.
Sample designation The antibody used by Doumerc et al. (1986, 6th Intl. Congress of Immunology, Toronto, Ontario, Canada, Jul. 6-11, 1986, Abstr. 5.54.6, p. 708), IOT4, was evaluated for its ability to measure the same form of CD4 antigen as that detected in the assay using 8F4 with R2B7. Table XXV shows the results when IOT4 antibody was used as both capture and detection reagent as was done by Doumerc et al.

TABLE XXV

| Capture Antibody | | Detection Antibody | | |
|---|---|---|---|---|
| | | 8F4 | IOT4 | R2B7 |
| CD4 DETECTION IN CELL LYSATE* | | | | |
| 8F4 | +NP40 | .037 | 0.051 | 0.545 |
| | −NP40 | .013 | 0.035 | 0.423 |
| IOT4 | +NP40 | .624 | 0.035 | 0.381 |
| | −NP40 | .063 | 0.017 | 0.040 |
| R2B7 | +NP40 | ND | 0.040 | 0.400 |
| | −NP40 | ND | 0.049 | 0.320 |
| RECOMBINANT SOLUBLE CD4 DETECTION* | | | | |
| 8F4 | +NP40 | .003 | .142 | 1.341 |
| | −NP40 | .005 | .155 | 1.421 |
| IOT4 | +NP40 | .004 | .010 | 0.010 |
| | −NP40 | .006 | .014 | 0.006 |
| R2B7 | +NP40 | ND | .133 | 1.18 |
| | −NP40 | ND | .134 | 1.18 |

*Values shown are OD₄₉₀. Where indicated, 0.25% NP40 was present in both the sample diluent and conjugate diluent of the sandwich immunoassay. Recombinant CD4 assays were carried out using a standard dilution of cell culture supernatant of transfected CHO cells. ND: Not determined Antibodies were evaluated for CD4 detection using different combinations of capture and detection reagents in assay matrices. Assays were carried out using 25% fetal calf serum in tris buffered saline, with and without Nonidet P40 (NP40) in both sample and conjugate diluents (Table XXV). IOT4 reacted with detergent solubilized CD4 but failed to react with the recombinant soluble CD4. Also shown in Table XXV are antibodies 8F4 and R2B7 in combination with themselves and IOT4. When used as a capture reagent, IOT4 detected only CD4 in cell lysates. Interestingly, however, when IOT4 was used as a detection reagent with 8F4 or R2B7 used as capture reagent, a much stronger signal is seen for the recombinant CD4 antigen than is seen with solubilized CD4 in cell lysates. It should be noted that this signal (for recombinant CD4) is significantly less than the signal obtained when R2B7 is paired with 8F4 as either detection or capture reagent. R2B7 when paired with itself was capable of a strong signal for both recombinant and cell lysate samples. Inclusion of NP40 failed to disrupt this signal. In contrast, 8F4 did not show such behavior, reacting only weakly with both cell lysate and recombinant material when used in both parts of the sandwich. IOT4 also failed to give a significant signal when paired with B66.1 and B67.2 for both cell lysate and recombinant samples.

Table XXVI shows the results of screening culture supernatants from T cell lines or clones derived from patients with rheumatoid arthritis or lung cancer.

TABLE XXVI

SOLUBLE CD4 AND CD8 DETECTION

| Sample Designation | Phenotype | Soluble CD8 (U/ml)* | Soluble CD4 (U/ml)* |
|---|---|---|---|
| 1 | CD4⁺ clone | 112 | 249 |
| 2 | CD4⁺ clone | 102 | 241 |
| 3 | CD4⁺ clone | 111 | 277 |
| 4 | CD8⁺ clone | 2,388 | |
| 5 | CD4⁺ clone | 4,000 | 90 |
| 6 | CD4⁺, CD8⁺ clone | 63 | 70 |

TABLE XXVI-continued

SOLUBLE CD4 AND CD8 DETECTION

| Sample Designation | Phenotype | Soluble CD8 (U/ml)* | Soluble CD4 (U/ml)* |
|---|---|---|---|
| TII 5 | CD4+, CD8+ mixed line | 568 | 61 |
| TII 6 | CD4+, CD8+ mixed line | 4,000 | 238 |
| TII 6 2 | CD4+, CD8+ mixed line | 4,000 | 120 |
| TII 7 PBT | CD4+, CD8+ mixed line | | 51 |
| TII 4 | B cell line | | |
| 5B4 | CD4+ clone | | 120 |
| 6G7 | CD4+ clone | | 240 |
| 5A1 | CD4+ clone | | 223 |
| 5C8 | CD4+ clone | | 115 |
| 6G7 | CD4+ clone | | 193 |
| 6D11 | CD4+ clone | | 116 |
| 5B4 | CD4+ clone | | 150 |
| 6D2 | CD4+ clone | 53 | 176 |
| 5C4 | CD4+ clone | | 117 |
| ST1 2H1 | CD4+ clone | 52 | 178 |
| ST1 1C10 | CD4+ clone | | 160 |
| ST1 13G11 | CD8+ clone | 3,217 | |
| ST2 13C6 | CD4+ clone | | 132 |
| ST2 13C6 2 | CD4+ clone | | 53 |
| ST2 11C12 | CD8+ clone | 1,046 | |
| ST2 13A10 | CD4+ clone | 369 | 94 |
| ST2 CM | CD4+, CD8+ mixed line | 221 | |
| ST2 13H1 | CD8+ clone | 3,428 | |
| ST2 14A5 | CD4+ clone | 72 | 142 |
| ST2 13A5 | CD4+ clone | 71 | 161 |
| ST 13 PB | CD4+, CD8+ mixed line | 4,000 | 50 |
| ST 16 | CD4+, CD8+ mixed line | 901 | 247 |
| ST5 PBT | CD4+, CD8+ mixed line | 240 | |
| ST5 | CD4+, CD8+ mixed line | | |
| TII4 PBT | CD4+, CD8+ mixed line | 4,000 | 71 |
| TII4 10F8 | CD4+, CD8+ mixed line | 1,217 | 70 |
| ST12 | CD4+, CD8+ mixed line | 4,000 | |
| ST11 | CD4+, CD8+ mixed line | 4,000 | 139 |

*Blank values indicate undetectable levels. CD4 units were defined in terms of the amount of absorbance of CD4 antigen found in a lysate of $10^3$ Jurkat T cells in 1% NP40 buffer, as measured using 8F4 as capture and R2B7 as detection reagents. CD8 units were based on a reference preparation of culture supernatant from Jurkat T cells used to standardize the CELLFREE ® T8 (T Cell Sciences, Cambridge, MA) assay.

Cell phenotype was determined by flow cytometry. Soluble CD4 was determined using 100 μl cell culture supernatant in a single-step assay using R2B7 as the antibody immobilized on the solid phase with biotinyl Leu3a and striptavidin peroxidase used for detection. A commercially available sandwich immunoassay kit (CELLFREE® T8 Test Kit, T Cell Sciences, Inc., Cambridge, Mass.) was used to measure soluble CD8. The CD8 antigen detected by this assay has been characterized previously as a 52–55 kD dimer composed of monomer polypeptides, each with a molecular weight of approximately 27 kD. As shown in Table XXVI, 21 of 21 CD4+ clones showed soluble CD4 in the supernatent. Zero of four CD8+ clones showed soluble CD4 in the supernatant. The cell lines showed varying mixes of soluble CD4 and soluble CD8. No correlation was observed between cell number and level of soluble CD4.

Table XXVII shows the rate of release of CD4 into the media after in vitro stimulation of peripheral blood mononuclear cells.

TABLE XXVII

SOLUBLE CD4 LEVELS AFTER IN VITRO CELL STIMULATION

| Experiment # | Type of Cell Stimulation* | Days in Culture | Soluble CD4 (U/ml)** |
|---|---|---|---|
| 1 | PHA | 1 | 4.4 |
| | | 2 | 6.4 |
| | | 3 | 15.0 |
| | | 4 | 17.4 |
| 1 | OKT3 | 1 | 1.8 |

TABLE XXVII-continued

SOLUBLE CD4 LEVELS AFTER IN VITRO CELL STIMULATION

| Experiment # | Type of Cell Stimulation* | Days in Culture | Soluble CD4 (U/ml)** |
|---|---|---|---|
| | | 2 | 4.4 |
| | | 3 | 7.6 |
| | | 4 | 11.5 |
| 1 | NONE | 1 | 1.1 |
| | | 2 | 1.1 |
| | | 3 | 4.8 |
| | | 4 | <1.0 |
| 2 | PHA | 1 | 7.6 |
| | | 3 | 24.3 |
| | | 4 | 43.9 |
| | | 5 | 41.6 |
| 2 | Phorbol myristate, acetate plus ionophore A2317 | 1 | 10.3 |
| | | 3 | 12.9 |
| | | 4 | 12.7 |
| | | 5 | 7.8 |

*Carried out as described in Section 23.1.3, supra.
**CD4 units were as defined for Table XXVI.

In experiment #1, PHA showed significantly greater effect than stimulation with OKT3. Similarly, in experiment #2, PHA was significantly more effective than phorbol esters and ionophores at inducing CD4 release. No significant release occurred when cells were put into culture without mitogen, suggesting release is an active process and not merely due to cell death.

Table XXVIII shows levels of soluble CD4 detected in sera of individuals with HTLV-1 associated adult T cell leukemia.

TABLE XXVIII

DETECTION OF SOLUBLE CD4 IN PATIENT SERA

| Sample Designation | Disease | Soluble CD4 (units/ml)* |
|---|---|---|
| 1165 | Acute Adult T Cell leukemia | 3.51 |
| 1166 | Acute Adult T Cell leukemia | 37.56 |
| 1167 | Acute Adult T Cell leukemia | 7.90 |
| 1168 | Acute Adult T Cell leukemia | 5.61 |
| 1169 | Acute Adult T Cell leukemia | 1.41 |
| 1170 | Acute Adult T Cell leukemia | 1.07 |
| 1171 | Acute Adult T Cell leukemia | 0.08 |
| 1172 | Acute Adult T Cell leukemia | 0.52 |
| 1173 | Acute Adult T Cell leukemia | 9.41 |
| 1174 | Acute Adult T Cell leukemia | 9.54 |
| 1175 | Chronic Adult T Cell leukemia | 8.92 |
| 1176 | Chronic Adult T Cell leukemia | 0.66 |
| 1177 | Chronic Adult T Cell leukemia | 2.54 |
| 1178 | Chronic Adult T Cell leukemia | 0.23 |
| 1179 | Chronic Adult T Cell leukemia | 0.31 |
| 1180 | Chronic Adult T Cell leukemia | 0.23 |
| 1181 | Chronic Adult T Cell leukemia | 1.83 |
| 1182 | Chronic Adult T Cell leukemia | 3.36 |
| 1183 | Chronic Adult T Cell leukemia | 2.21 |
| 1184 | Chronic Adult T Cell leukemia | 3.78 |
| 1185 | Smoldering Adult T Cell leukemia | 0.87 |
| 1186 | Smoldering Adult T Cell leukemia | 0.59 |
| 1187 | Smoldering Adult T Cell leukemia | 0.24 |
| 1188 | Smoldering Adult T Cell leukemia | 0.31 |
| 1189 | Smoldering Adult T Cell leukemia | 1.34 |
| 1190 | Smoldering Adult T Cell leukemia | 1.01 |
| 1191 | Smoldering Adult T Cell leukemia | 1.61 |
| 1192 | Smoldering Adult T Cell leukemia | 0.91 |

*Detected using R2B7 as capture reagent and biotinylated Leu3A as detection reagent. CD4 units were as defined for Table XXVI.

Individuals with the most active stages of the disease had the highest levels of soluble CD4 in their sera.

FIG. 22 shows the levels of CD4 in sera of normal individuals and in patients from a number of disease groups. Levels of CD4 in synovial fluid of rheumatoid arthritis patients and in sera of lung cancer patients were elevated as compared to the levels in sera from normal individuals.

Table XXIX shows CD4 levels in longitudinal samples from patients on IL-2 therapy.

TABLE XXIX
SOLUBLE CD4 LEVELS IN PATIENTS UNDERGOING IL-2 THERAPY*

| Patient Designation | Date (mo./day) | Soluble CD8 (U/ml) | Soluble CD4 (U/ml) | Soluble IL2R (U/ml) |
|---|---|---|---|---|
| A | 4/27 | 184 | 7 | 1302 |
| A | 5/04 | 492 | 19 | >1600 |
| A | 5/06 | 531 | 28 | >1600 |
| A | 5/10 | 529 | 27 | >1600 |
| A | 5/11 | 490 | 22 | >1600 |
| B | 1/29 | 325 | 10 | 385 |
| B | 2/04 | 595 | 19 | >1600 |
| B | 2/10 | 1221 | 12 | >1600 |
| B | 2/12 | 914 | 17 | >1600 |
| B | 2/20 | 452 | 16 | >1600 |
| C | 1/05 | 319 | 21 | 964 |
| C | 1/15 | 1232 | 26 | >1600 |
| C | 1/21 | 890 | 26 | >1600 |
| D | 1/15 | 269 | 10 | 294 |
| D | 3/04 | 271 | 7 | >1600 |
| D | 3/09 | 519 | 16 | >1600 |
| D | 3/10 | 484 | 10 | >1600 |
| E | 3/23 | 621 | 14 | >1600 |
| F | 3/22 | 315 | 165 | 627 |
| F | 3/29 | 615 | 102 | >1600 |
| F | 4/05 | 898 | 140 | >1600 |
| Patient 1 |  | 333 | 9 | 494 |
| Patient 2 |  | 222 | 22 | >1600 |
| Patient 3 |  | 274 | 12 | 683 |
| Patient 4 |  | 149 | 11 | 650 |
| Patient 5 |  | 1492 | 49 | >1600 |
| Patient 6 |  | 1008 | 74 | >1600 |
| Patient 7 |  | 608 | 8 | >1600 |
| Patient 8 |  | 2094 | 27 | >1600 |
| Patient 9 |  | 779 | 16 | >1600 |
| Patient 10 |  | 1400 | 31 | >1600 |
| Normal 1** |  | 476 | 9 | 466 |
| Normal 2** |  | 311 | 6 | 540 |
| Normal 3** |  | 178 | 3 | 396 |
| Normal 4** |  |  | 5 |  |
| Normal 5** |  |  | 3 |  |
| Normal 6** |  |  | 4 |  |
| Normal 7** |  |  | 6 |  |
| Normal 8** |  |  | 6 |  |
| Normal 9** |  |  | 8 |  |
| Normal 10** |  |  | 3 |  |

*Soluble CD8 was measured using the CELLFREE ® T8 Test Kit (T Cell Sciences, Cambridge, MA). Soluble CD4 was detected using 8F4 capture, R2B7 detection. CD4 units were as defined for Table XXVI. Soluble IL2R was measured using the CELLFREE ® IL2R Test Kit (T Cell Sciences, Cambridge, MA).
**Healthy blood donors (not undergoing IL-2 therapy)

The data of Table XXIX shows that detectable levels of soluble CD4 are present in sera of patients being treated with IL-2. One of the events observed in IL-2 therapy is an increase in circulating activated CD4 positive lymphocytes. Soluble CD4 levels in these patients fluctuate throughout the course of therapy and may have prognostic value.

Table XXX shows levels of soluble CD4, along with soluble IL2R, in renal transplantation patients.

TABLE XXX
SOLUBLE CD4 LEVELS IN RENAL TRANSPLANTATION PATIENTS

| Patient Designation | Sample Date (mo./day) | Soluble CD4* (U/ml) | Soluble IL2R (U/ml) |
|---|---|---|---|
| P | 4/07 | 6.4 | 455 |
|  | 4/09 | 7.6 | 493 |
|  | 4/14 | 20.4 | 4090 |
|  | 4/16 | 9.3 | 3865 |
|  | 5/02 | 6.8 | 1200 |
|  | 5/30 | 37.4 | 565 |
| H | 3/14 | 16.4 | 811 |
|  | 3/21 | 11.7 | 441 |
|  | 4/09 | 12.4 | 347 |
|  | 5/14 | 21.6 | 692 |
|  | 6/11 | 36.9 | 907 |
| L | 6/15 | 91.8 | 1965 |
|  | 6/16 | 29.2 | 2705 |
|  | 6/23 | 38.1 | 3990 |
|  | 6/30 | 48.8 | 7400 |
|  | 7/07 | 35.2 | 6300 |
| G | 4/30 | 26.1 | 1288 |
|  | 5/05 | 7.6 | 700 |
|  | 5/07 | 24.2 | 1845 |
|  | 5/09 | 32.6 | 3625 |
|  | 5/12 | 17.1 | 3635 |
|  | 5/14 | 18.8 | 3035 |
|  | 5/16 | 21.2 | 3040 |
|  | 5/21 | 20.0 | 4080 |
|  | 6/04 | 46.5 | 2475 |
|  | 6/25 | 19.4 | 1995 |
| S | 6/13 | 6.6 | 1090 |
|  | 6/16 | 13.7 | 680 |
|  | 6/18 | 13.1 | 930 |
|  | 6/20 | 11.1 | 1705 |
|  | 6/23 | 8.3 | 2708 |
|  | 6/25 | 19.5 | 5515 |
|  | 6/27 | 11.2 | 3460 |
|  | 6/30 | 9.9 | 2205 |
|  | 7/07 | 12.8 | 1825 |

*Detected using 8F4 capture, R2B7 detection
Analyzed using CELLFREE ® IL2R Test Kit Elevated levels of CD4 did not show a correlation with IL2R but did, like IL2R, show increases during rejection episodes.

23 2.2. Results Using Optimized Assay Protocol

Once the soluble CD4 assay was optimized and any effects of rheumatoid factor eliminated, it was possible to detect much lower levels of soluble CD4. For normal healthy individuals, the range of soluble CD4 was 8 U/ml to 36 U/ml with a mean of 17.2 U/ml. This was determined from the assay of 189 normal samples. A high number of replicates was also run to achieve confidence at the low end of the range.

Using this improved assay, a series of renal transplant patients was analyzed, and the data is presented in Table XXXI.

TABLE XXXI
RENAL TRANSPLANT PATIENTS

| PATIENT | Diagnosis[1] | Soluble CD4 (U/ml)[2] | Soluble IL-2R (U/ml)[3] | Soluble CD8 (U/ml)[4] |
|---|---|---|---|---|
| C1 | CsA | 69 | 200 | 181 |
|  | CsA | 30 | 340 | 448 |
| B1 | Rejection | 15 | 240 | 47 |
| Z1 | Stable | 19 | 380 | 310 |
|  | Stable | 19 | 390 | 374 |
|  | Stable | 15 | 300 | 321 |
| R1 | Rejection | 24 | 420 | 481 |
|  | Rejection | 33 | 820 | 120 |
| M1 | CsA | 122 | 770 | 534 |
|  | CsA | 29 | 330 | 570 |
|  | CsA | 26 | 80 | 526 |
| L1 | Rejection | 43 | 1040 | ND |
|  | Rejection | 30 | 1120 | ND |
| S1 | Rejection | 25 | 680 | ND |
| P1 | Rejection | 44 | 2180 | 1894 |
|  | Rejection | 25 | 370 | 390 |

TABLE XXXI-continued

| RENAL TRANSPLANT PATIENTS | | | | |
|---|---|---|---|---|
| PATIENT | Diagnosis[1] | Soluble CD4 (U/ml)[2] | Soluble IL-2R (U/ml)[3] | Soluble CD8 (U/ml)[4] |
| S2 | CsA | 117 | 510 | 267 |
|  | CsA | 22 | 390 | 67 |
| A1 | Stable | 96 | 400 | 731 |
|  | Stable | 27 | 320 | 390 |
|  | Stable | 23 | 40 | 409 |
| L2 | Rejection | 23 | 1240 | 228 |
|  | Rejection | too high | 1000 | 1559 |
|  | Rejection | 24 | 1050 | 452 |

[1]Diagnosis was either cyclosporin A toxicity (CsA), stable transplant, or rejection; multiple patient serum samples were taken at different times.
[2]Soluble CD4 was measured using the improved assay (Section 23.1.2.2, supra).
[3]Soluble IL2R was measured using the CELLFREE ® IL-2R Test kit (T Cell Sciences, Cambridge, MA).
[4]Soluble T8 was measured using the CELLFREE ® T8 Test kit (T Cell Sciences, Cambridge, MA).
ND: Not Determined.

The above data indicates that it was possible to detect soluble CD4 levels in renal transplant patients in the phases of rejection, toxicity and stability. It was also possible to detect elevated levels of other soluble T cell surface markers, such as soluble CD8 and soluble IL2R. This data shows that soluble receptors are present during the course of transplant episodes. It is expected that a longitudinal study of each of these patients will provide data that will indicate how the levels of each soluble marker change with toxicity, rejection or stability episodes. Thus, a change in the observed level for any particular marker, such as an increase or decrease or no change, may be of more value than the absolute level of a marker present at any one point in time, for the diagnosis or monitoring of treatment in disease (see Section 25, infra). For comparison, the change in the observed level of a marker must be compared to a baseline level which could either be the level seen in normal individuals with no disease, the pre-transplant level in the renal patient, the value present in a stable situation or during remission of symptoms, etc.

In a preferred embodiment, the diagnosis of disease or monitoring of treatments of patients with renal transplants or other diseases and states of immune activation will be through an analysis of a panel of soluble T cell markers, rather than from only one individual marker. Thus, for example, a better prognostic indicator can be a rise in one marker relative to a simultaneous fall in another marker. The resulting profile of soluble T cell marker expression should be an exquisite indicator of minute changes in the immune system as its function is modified by therapeutic treatments or disease progression (see Section 26, infra).

Table XXXII gives the values of soluble CD4 levels seen during preliminary studies on patients with Acquired Immune Deficiency Syndrome (AIDS) and other stages of HIV-induced disease including Kaposi's Sarcoma (KS), AIDS related complex (ARC) or asymptomatic seropositive (ASYM).

TABLE XXXII

| LEVELS OF SOLUBLE RECEPTORS IN HIV-INFECTED PATIENTS | | | | |
|---|---|---|---|---|
| PATIENT | Diagnosis | Soluble CD4* (U/ml) | Soluble IL-2R* (U/ml) | Soluble CD8* (U/ml) |
| 1 | AIDS | 10 | 699 | 1236 |
| 2 | AIDS | 10 | 792 | 2351 |
| 3 | AIDS | 20 | 1092 | 1099 |
| 4 | AIDS | 21 | 506 | 1706 |
| 5 | AIDS | 24 | 2105 | 1104 |
| 6 | AIDS | 56 | 1340 | 753 |
| 7 | AIDS | 25 | 2099 | 1440 |
| 8 | AIDS | 1 | 1760 | 1007 |
| 9 | AIDS | 20 | 1964 | 626 |
| 10 | AIDS | 3 | 1079 | 306 |
| 11 | AIDS | 1 | 1529 | 343 |
| 12 | AIDS | 13 | 1025 | 647 |
| 13 | AIDS | −1 | 2014 | 438 |
| 14 | AIDS | 16 | 747 | 507 |
| 15 | ARC | 71 | 1645 | 2646 |
| 16 | ARC | 23 | 967 | 7331 |
| 17 | ASYM | 11 | 489 | 487 |
| 18 | ARC | 23 | 563 | 4073 |
| 19 | ARC | 177 | 1508 | 1246 |
| 20 | ARC | −0 | 978 | 572 |
| 21 | ARC | 15 | 2093 | 1731 |
| 22 | ARC | 16 | 1742 | 1279 |
| 23 | ASYM | 15 | 740 | 2700 |
| 24 | ASYM | 28 | 1403 | 1583 |
| 25 | ASYM | 24 | 1392 | 3037 |
| 26 | ASYM | 13 | 1084 | 2290 |
| 27 | ASYM | 12 | 558 | 1915 |
| 28 | ASYM | 19 | 1182 | 5580 |
| 29 | ASYM | 14 | 1308 | 1702 |
| 30 | ASYM | 16 | 806 | 430 |
| 31 | ASYM | 17 | 1012 | 1386 |
| 32 | ASYM | 13 | 1541 | 5127 |
| 33 | ASYM | 42 | 1752 | 4022 |
| 34 | ASYM | 10 | 504 | 1598 |

*Assays as indicated for Table XXXI.

From the above data, it is clear that although the values of soluble CD4 are low compared to the other soluble marker levels, they are easily detectable in sera from patients having different stages of HIV-induced disease. As discussed supra, improved prognostic indices based upon levels or changes in levels of these soluble markers are expected with longitudinal studies involving a panel of soluble receptor markers. Such studies should reveal a profile of soluble receptors that can be used to determine the stage of progression towards AIDS in patients or the response to treatment of such patients. A longitudinal study of the patients in Table XXXII and others can be conducted to determine the soluble receptor profiles of the patients and to correlate these profiles with the efficacy of their ongoing azidodeoxythymidine treatment (see Section 25, infra).

Using the improved assay format, paired samples of synovial fluid and serum were analyzed for several patients with rheumatoid arthritis. This data is presented in Table XXXIII.

TABLE XXXIII

| DETECTION OF SOLUBLE CD4 IN PAIRED SYNOVIAL FLUID AND SERUM SAMPLES FROM INDIVIDUAL PATIENTS | | | |
|---|---|---|---|
| PATIENT | Sample[1] | Soluble CD4 (U/ml) + HA[2] | Soluble CD4 (U/ml) + IgG[3] |
| 1 | serum | 16 | 13 |
|  | fluid | 42 | 36 |
| 2 | serum | 15 | 12 |
|  | fluid | 64 | 57 |
| 3 | serum | 15 | 14 |
|  | fluid | 44 | 39 |
| 4 | serum | 21 | 16 |
|  | fluid | 103 | 96 |
| 5 | serum | 23 | 19 |
|  | fluid | 66 | 59 |
| 6 | serum | 19 | 14 |

TABLE XXXIII-continued
DETECTION OF SOLUBLE CD4 IN PAIRED SYNOVIAL FLUID AND SERUM SAMPLES FROM INDIVIDUAL PATIENTS

| PATIENT | Sample[1] | Soluble CD4 (U/ml) + HA[2] | Soluble CD4 (U/ml) + IgG[3] |
|---|---|---|---|
|  | fluid | 41 | 37 |
| 7 | serum | 22 | 22 |
|  | fluid | 78 | 84 |
| 8 | serum | 15 | 13 |
|  | fluid | 80 | 73 |
| 9 | serum | 15 | 13 |
|  | fluid | 87 | 90 |
| 10 | serum | 19 | 15 |
|  | fluid | 129 | 125 |

[1] Samples were obtained from the serum or synovial fluid of each patient.
[2] HA = heat aggregated IgG added to remove any false positive problems associated with occasional high RF (rheumatoid factor) containing samples.
[3] IgG = unaggregated IgG control to detect samples that may have had RF problems.

The above data indicates that with the increased sensitivity of the employed assay, it was possible to detect soluble CD4 levels in both serum and synovial fluid samples of rheumatoid arthritis patients. The levels observed in serum samples were within the normal range, however. Furthermore, the levels of soluble CD4 were elevated in synovial fluid samples relative to serum samples form 10 of 10 patients analyzed. This suggests a localized production and release of CD4 antigen.

Levels of soluble CD4 in sera of normal individuals and patients from a number of disease groups were measured, with the results shown in FIG. 23. Elevated levels of soluble CD4 were observed in renal transplant patients, synovial fluid of rheumatoid arthritis patients, in some patients with EBV infections, and in patients with various leukemias.

23.3. Discussion

Assays have been described herein that allow the measurement of CD4 in a detergent solubilized membrane form, in a recombinant soluble form (genetically engineered to exclude the transmembrane region), and in a spontaneously released form from activated T cells. Nine different anti-CD4 antibodies, in a total of 63 different configurations (one configuration consisting of a single capture and a single detection antibody) were screened for suitability for detecting CD4 in cell lysates. Nine such suitable configurations were identified. Of these, only five configurations showed significant reactivity with soluble recombinant CD4. Three of these five configurations involved R2B7 as one of the antibodies. R2B7 when paired with 8F4 showed greatest sensitivity for detecting soluble CD4 both from recombinant and natural sources. The greatest ratio of signal from a soluble recombinant CD4 to signal from solubilized lysate CD4 is seen using 8F4 capture with R2B7 detection. This is roughly twice the ratio seen in the reverse configuration. It is possible that binding of one or more of the antibodies induces conformational changes in the molecule. This is supported by the observation that when IOT4 is used as a capture reagent, only solubilized lysate CD4 may be detected (using 8F4 or R2B7 detection), whereas when 8F4 or R2B7 are used as capture in combination with IOT4 as detection, soluble CD4 is preferentially detected over solubilized lysate CD4. Recombinant CD4 serves as a good model for released CD4 since those antibody combinations which work best with recombinant soluble CD4 also work best with the spontaneously soluble form of the molecule. Thus, selection of the antibodies and their configuration in the sandwich immunoassay is crucial to successful detection of released CD4.

Doumerc et al. (1986, 6th Intl. Congress of Immunology, Toronto, Ontario, Canada, Jul. 6–11, 1986, Abstr. 5.54.6, p. 708) have described an enzyme immunoassay based on the use of IOT4 as a capture and detection reagent to detect CD4 in serum. In our hands, this configuration works only to measure the membrane form of the molecule and fails to adequately measure the soluble recombinant or soluble spontaneously released form of the molecule described here. Doumerc et al. (id.) disclose increased serum CD4 during transient episodes of lymphocyte destruction. It is possible that the form of the molecule measured by Doumerc et al. represents a form still associated with pieces of membrane, not a truly soluble moiety. Such a membrane form will tend to aggregate or associate into micelles or vesicles, thus rendering it capable of detection in a sandwich immunoassay using the same antibody as both capture and detection reagent. Since soluble CD4 is not known to exist in multimeric structures, in the absence of repeating epitopes, the same antibody cannot be used as both capture and detection reagent for assay of soluble CD4. Doumerc et al. further suggest that the CD4 they measure correlates with total CD4 cell pool. We suggest that CD4 release, like CD8, is rather a function of activation of cells. This is supported by the kinetics of released CD4 observed during in vitro stimulation. Thus, the molecule described by Doumerc is significantly different from the molecule described herein.

CD4 release may be a function of the type and pathway of activation. Phytohemagglutinin and T3 stimulation both resulted in a release of small amounts of CD4. Stimulation with phorbol esters, known to cause phosphorylation and internalization of CD4, or with ionophores, resulted in significantly less released CD4 than did PHA stimulation, despite intense cellular activation. The kinetics of CD4 release were also significantly different between cells stimulated by phorbol esters and those stimulated by PHA. Release can also not be attributed to simple membrane turnover. No CD4 is released by resting cells in vitro.

Cloned IL-2 dependent CD4+ T cells or T cell lines containing CD4+ cells all showed detectable soluble CD4 in their culture supernatants. CD8 cells showed only soluble CD8. Thus, the released molecules are an accurate reflection of the cell surface phenotype of the cells. No correlation was observed between levels of soluble CD4 and the number of cells.

Low levels of CD4 were seen in sera from normal individuals. Elevated soluble CD4 was observed in certain individuals with EBV infection, lung cancer and with T cell leukemias, and correlated overall with the stage of disease (FIG. 22, 23). Elevations in CD4 antigen levels were also observed in disorders due to HIV infection, and in some synovial fluid, but not sera, from patients with rheumatoid arthritis. Elevations were observed in certain patients on IL-2 therapy where there is activation of CD4+ as well as CD8+ cells and natural killer cells. Finally, elevations were observed in sera of some patients undergoing renal allograft rejection or cyclosporin A toxicity. Soluble CD4 levels may thus be of value in the diagnosis and monitoring of a pathologic event.

The relationship between spontaneously released CD4 and membrane CD4 can be determined from patterns of antibody reactivity. If the spontaneously released material were identical to the cell-surface polypeptide, it should behave in the assays, which have detergent incorporated into them, like solubilized CD4 in cell lysate. If they are more analogous to the recombinant truncated version of CD4 they should behave like it. The latter is the case; that is, those antibody pairs which afford suitable detection of solubilized lysate CD4, but not recombinant soluble CD4, yielded poor detection of the soluble CD4 from T cell culture supernatant, whereas those antibody pairs showing optimal reactivity with recombinant soluble CD4 also reacted optimally with the released material. It is clear from antibody reactivity patterns that the released form of the CD4 antigen differs significantly from the membrane form.

A key element in deriving a successful sandwich immunoassay for the detection of soluble CD4 was the strategy employed in antibody selection. A readily available model source of soluble CD4, recombinant truncated CD4, was used in a screening procedure to select antibodies with a preferential ability to identify the released form of the molecule. Using this criteria, a pair of antibodies was selected that could detect spontaneously released CD4 in sera and in culture supernatants. This strategy may be widely applicable to the detection and discovery of other released molecules.

24. ELEVATED CONCENTRATIONS OF SOLUBLE INTERLEUKIN-2 RECEPTORS IN SERUM OF SMOKERS AND LUNG CANCER PATIENTS

In the examples herein, we describe the results of experiments which demonstrate that increased levels of soluble IL2R are found in the sera of smokers relative to nonsmokers, and in the sera of patients with lung cancer relative to healthy patients. In addition, asymptomatic patients with relatively limited and moderately differentiated squamous cell carcinoma had significantly higher levels of soluble IL2R than symptomatic patients, with big tumors and advanced disease.

Lung cancer is the most common cause of cancer death in men and women. Cigarette smoking has been shown repeatedly to be a major risk factor for lung cancer, and a close correlation exists between the risk of lung malignancy and the number of cigarettes smoked.

Several alterations in immunity have been demonstrated in both cigarette smokers and lung cancer patients, including abnormalities in the T cell profile (Holt, P. G., et al., 1987, Thorax 42:241-9; Ginns, L. C., et al., 1982, Am. Rev. Resp. Dis. 126:265-9), natural killer (NK) cell activity (Hughes, D. A., et al., 1985, Clin. Exp. Immunol. 61:459-66; Ginns, L. C., et al., 1985, Am. Rev. Resp. Dis. 131:831-4) and altered broncheoalveolar lavage cell populations (Hunninghake, G. W., et al., 1979, Am. J. Pathol. 97:149-78). Several studies have demonstrated increased numbers of activated T cells in both tumor infiltrating lymphocytes and peripheral blood lymphocytes of lung cancer patients (Kurnick, J. T., et al., 1986, Clin. Immunol. Immunopath. 38:367-80; Tsuyuguchi, I., et al., 1986, Chest 89:705-8).

In order to investigate the role of soluble IL2R in lung cancer, we determined the levels of soluble serum IL2R in different histopathological types of untreated lung cancer patients.

24.1. Materials and Methods

24.1.1. Patients

We studied 49 patients with lung cancer, all of whom had histopathological or cytological confirmation at the Massachusetts General Hospital. These 49 cases comprised 26 cases of adenocarcinoma (AC) (mean age 63 years) and 23 patients with squamous cell lung carcinoma (SCLC) (mean age 63 years) (Table XXXIV).

TABLE XXXIV

| LUNG CANCER PATIENT GROUPS | | | | |
|---|---|---|---|---|
| | Adenocarcinoma | | Squamous Cell Lung Carcinoma | |
| | N* | Mean Age (years) | N* | Mean Age (years) |
| Male | 16 | 63 | 20 | 62 |
| Female | 10 | 64 | 3 | 69 |
| TOTAL | 26 | 63 | 23 | 63 |

*Number of patients in group

No patient had received chemotherapy, radiation therapy or surgery before sample collection.

In the adenocarcinoma group, 14 patients had stage I disease, 5 had stage IIIa, 6 had stage IIIb, and one had stage IV (Table XXXV).

TABLE XXXV

| DISEASE STATE OF LUNG CANCER PATIENTS | | |
|---|---|---|
| | Number of Patients (N) | |
| Stage | Adenocarcinoma | Squamous Cell Lung Carcinoma |
| Stage I | 14 | 6 |
| Stage II | 0 | 8 |
| Stage IIIa | 5 | 3 |
| Stage IIIb | 6 | 6 |
| Stage IV | 1 | 0 |
| TOTAL | 26 | 23 |

In the squamous cell lung carcinoma group, 6 patients had stage I disease, 8 had stage II, 3 had stage IIIa and 6 had stage IIIb (Table XXXV). None of the patients with AC had stage II disease, and none of the patients with SCLC had stage IV disease (see Mountain, C. F., 1986, Chest 89:225 Supp., for lung cancer staging system).

Smoking histories ranged from 0 to more than 130 pack years (packs per day multiplied by years of smoking). The study group, ranging in age from 44 to 84 years, comprised 36 males (mean age 62 years) and 13 females (mean age 66 years).

24.1.2. CONTROLS

Healthy adult volunteer non-smokers (n=15) and smokers [(n=45) (light smokers, n=15, <20 pack/years; moderate smokers, n=15, 21-49 pack/years; heavy smokers, n=15, >50 pack/years)] served as the control group. This group consisted of 38 males (mean age 35 years) and 22 females (mean age 34 years).

24.1.3. Serum Samples

Blood obtained by venipuncture was allowed to clot at room temperature for 1 hour; after centrifugation the serum was stored in volumes of 1 ml at −70° C. until assayed. All samples were tested on the same date.

24.1.4. Soluble IL2R Assay

The commercially available enzyme immunoassay for soluble IL2R (T Cell Sciences, Inc. Cambridge, Mass.), CELLFREE®, was used. Briefly, each well of a 96 microtiter well plate (Nunc, Denmark; certified high binding) was coated overnight at 4° C. with a solution of murine anti-human soluble IL2R antibody in PBS, pH 7.4. Any remaining protein-binding sites on the microtiter wells were then blocked for two hours at 37° C. with 300 μl per well of a solution of BSA (1%) (Kirkegard and Perry Laboratories, Bethesda, Md.) and Tween 20 (0.05%) (Zymed Laboratories, South San Francisco, Calif.) in PBS, pH 7.4. The wells were then washed with 350 μl of PBS and Tween 20. Following the final wash step, 50 μl of a sample diluent consisting of 0.15M NaCl, 25 mM Hepes (pH 7.4) were added to each well.

Fifty μl of standard or serum sample were added to the appropriate wells in duplicate. The plate was then sealed and incubated at 37° C. for 2 hours. The solution was aspirated from the plate and each well was washed three times with 350 μl of PBS/Tween 20. 100 μl of HRP-conjugated murine monoclonal anti-human soluble IL2R antibody directed against a different epitope on the soluble IL2R were added to each well, and the plate was again incubated at 37° C. for 2 hours. The plate was once again washed three times with PBS/Tween 20. After this step, 100 μl of o-phenylenediamine (0.02%), dissolved in 0.1M sodium citrate buffer, pH 5.5, were added to each well and the plate was incubated at room temperature for 30 minutes. At the end of this final incubation, 50 μl of 2N $H_2SO_4$ were added to each well to stop the reaction, and the absorbance of each well was read at 490 nm (Dynatech MR600, Dynatech Alexandria, Va.).

24.1.5. Statistical Analysis

The data were analyzed using the computing capacities of the CLINFO data analysis system. Data for soluble IL2R concentrations in serum samples of normal subjects and lung cancer patients were compared using Student's t test for 2 groups with unequal variances and analysis of variance (ANOVA).

Results in units per ml (U/ml) were expressed as the mean value±standard error of the mean.

24.2. Results

24.2.1. Concentrations of Soluble IL2R in Normal Non-smokers and Smokers

A comparison of soluble IL2R concentration in serum samples of normal non-smokers and smokers is shown in Table XXXVI.

TABLE XXXVI

| | NORMAL CONTROLS | | | |
|---|---|---|---|---|
| | N* | Mean Age (Year) | Pack/Year | Mean Soluble IL2R (U/ml) |
| Nonsmokers | 15 | | | 298 ± 22 |
| Smokers: | | | | 439 ± 33 |
| Light | 15 | | <20 | 390 ± 26 |
| Moderate | 15 | | 21–49 | 470 ± 93 |
| Heavy | 15 | | >50 | 456 ± 27 |
| Smokers and Nonsmokers | | | | |
| Combined | 60 | | | 403 ± 26 |
| Male | 38 | (35) | | |
| Female | 22 | (34) | | |
| | 60 | | | |

*Number of patients in group

The mean value of soluble IL2R in normal non-smokers was 298±22 U/ml, as compared with 439±33 U/ml in smokers. The difference was highly significant by Student's t test (p <0.001). Results from light, moderate, and heavy smokers were 390±26 U/ml, 470±93 U/ml, and 456±27 U/ml, respectively. Moderate and heavy smokers were significantly different from non-smokers (p<0.05).

24.2.2. Concentrations of Soluble IL2R in Lung Cancer

A comparison of soluble IL2R concentrations in serum samples of normal healthy controls, including smokers and non-smokers, and of patients with lung cancer is shown in Table XXXVII.

TABLE XXXVII

| SOLUBLE IL2R CONCENTRATION | | |
|---|---|---|
| Patient Group | N* | Soluble IL2R (U/ml) |
| Normal: | | |
| nonsmokers | 15 | 298 ± 22 |
| smokers | 45 | 439 ± 33 |
| Combined Normal | 60 | 403 ± 26 |
| Cancers: | | |
| adenocarcinoma | 26 | 717 ± 57 |
| squamous | 23 | 825 ± 73 |
| Combined Lung Cancer | 49 | 768 ± 46 |

*Number of patients in group

The mean value for soluble IL2R in the control group was 403±26 U/ml as compared with 768±46 U/ml in lung cancer serum samples. The difference was statistically significant (p<0.001, Student's t test).

The concentration of soluble IL2R from adenocarcinoma serum samples was 717±57 U/l as compared with 825±73 U/ml in squamous cell lung carcinoma (p=NS, Student's t test; Table XXXVII).

Both groups were significantly different from control smokers (p=0.001).

In twenty nine patients with moderately differentiated tumors, the level of soluble IL2R was 865±67 U/ml as compared to 627±42 U/ml in twenty patients with poorly differentiated tumors (p=0.004; Table XXXVIII).

TABLE XXXVIII

| SOLUBLE IL2R CONCENTRATIONS IN LUNG CANCER PATIENT SERA | | | | |
|---|---|---|---|---|
| | Moderately Differentiated Tumors | | Poorly Differentiated Tumors | |
| Lung Cancer | N** | Soluble IL2R (U/ml) | N** | Soluble IL2R (U/ml) |
| AC | 12 | 763 ± 110 | 14 | 677 ± 51 |
| SCLC | 17 | 936 ± 82 | 6 | 510 ± 55 |
| TOTAL | 29 | 865 ± 67* | 20 | 627 ± 42 |

*p < 0.01 vs. poorly differentiated tumors
Soluble IL2R value for normal smokers plus nonsmokers = 403 ± 26
**Number of patients in group No difference was found in soluble IL2R serum concentrations between twenty-eight patients with early stages (I and II) of lung cancer (833±73 U/ml) and twenty-one patients with more advanced disease (stage III and IV; 681±38 U/ml) (Table XXXIX).

TABLE XXXIX

| SOLUBLE IL2R CONCENTRATIONS IN PATIENTS IN DIFFERENT STAGES OF LUNG CANCER | | |
|---|---|---|
| Disease Stage | N* | Soluble IL2R** (U/ml) |
| Stage I & II | 14 AC | 833 ± 73 |
| | 14 SCLC | |
| | 28 | |

TABLE XXXIX-continued
SOLUBLE IL2R CONCENTRATIONS IN PATIENTS IN DIFFERENT STAGES OF LUNG CANCER

| Disease Stage | N* | Soluble IL2R** (U/ml) |
|---|---|---|
| Stage IIIa, IIIb, IV | 12 AC | 681 ± 38 |
| | 9 SCLC | |
| | 21 | |

*Number of patients in group
**Value for normal smokers and nonsmokers = 403 ± 26

24.2.3. Concentrations of Soluble IL2R in Serum of Patients with Squamous Cell Lung Carcinoma Levels of soluble IL2R in sera of patients in different stages of squamous cell carcinoma are shown in Table XL.

TABLE XL
SOLUBLE IL2R CONCENTRATIONS IN PATIENTS IN DIFFERENT STAGES OF SQUAMOUS CELL CARCINOMA

| Disease Stage | N* | Soluble IL2R (U/ml) |
|---|---|---|
| Stage I | 6 | 1019 ± 211 |
| Stage II | 8 | 901 ± 92 |
| Stage IIIa | 3 | 807 ± 94 |
| Stage IIIb | 6 | 539 ± 54 |
| Total | 23 | |

*Number of patients in group
$p < 0.05$ vs. Stage IIIb

The highest levels of soluble IL2R were seen in patients with stage I disease (1019±211 U/ml) and the lowest levels in stage IIIb of disease (539±54 U/ml) ($p<0.05$). Intermediate levels were found in patients with stage II and IIIa of disease (p=NS). Seventeen patients in this group had moderately differentiated tumors with a mean concentration of soluble IL2R of 936±82 U/ml as compared to six patients with poorly differentiated tumors with a mean level of soluble IL2R of 510±55 U/ml ($p<0.01$; Table XLI).

TABLE XLI
SOLUBLE IL2R CONCENTRATIONS IN PATIENTS WITH SQUAMOUS CELL CARCINOMA CLASSIFIED ACCORDING TO HISTOPATHOLOGY

| Histopathology | N* | Soluble IL2R (U/ml) |
|---|---|---|
| Moderately differentiated tumors | 17 | 936 ± 82 |
| Poorly differentiated tumors | 6 | 510 ± 55 |
| TOTAL | 23 | |

*Number of patients in group
$p < 0.001$ vs. poorly differentiated tumors

In Table XLII, patients appear stratified according to the differentiation of the tumor and the presence or absence of symptoms at the time of initial evaluation and sample collection.

TABLE XLII
SOLUBLE IL2R CONCENTRATIONS IN SERA OF PATIENTS WITH SQUAMOUS CELL CARCINOMA

| Patient Group | N** | Soluble IL2R (U/ml) |
|---|---|---|
| Moderately Differentiated Tumors | | |
| Asymptomatic | 6 | 1147 ± 126* |
| Symptomatic | 11 | 902 ± 71 |
| Poorly Differentiated Tumors | | |
| Asymptomatic | 2 | 590 ± 180 |
| Symptomatic | 4 | 470 ± 25 |

*$p < 0.01$ vs. poorly symptomatic
**Number of patients in group

As shown in Table XLII, asymptomatic patients with moderately differentiated tumors had a higher level of soluble IL2R (1147±126 U/ml) than symptomatic patients with poorly differentiated tumors (470±25 U/ml). The difference was highly significant ($p<0.01$). Symptomatic patients with moderately differentiated tumors and asymptomatic patients with poorly differentiated tumors had intermediate concentrations of soluble IL2R (902±71 U/ml and 590±180 U/ml, respectively) (p=NS). Similarly, when patients were classified according to the size of the tumor, 8 patients with small tumors (<2 cm in diameter), had a higher level of soluble IL2R (1045±151 U/ml) than 8 patients with bigger tumors (<4 cm in diameter) (633±74 U/ml) ($p<0.05$, Table XLIII).

TABLE XLIII
SOLUBLE IL2R CONCENTRATIONS IN PATIENTS WITH SQUAMOUS CELL CARCINOMA CLASSIFIED ACCORDING TO TUMOR SIZE

| Tumor Size | N* | Soluble IL2R (U/ml) |
|---|---|---|
| <2 cm | 8 | 1045 ± 151 |
| >4 cm | 8 | 633 ± 74 |

*Number of patients in group

24.2.4. Concentrations of Soluble IL2R in Patients with Lung Adenocarcinoma The mean concentration of soluble IL2R in 26 patients with adenocarcinoma was 717±57 U/ml. In contrast to patients with squamous cell carcinoma, patients with adenocarcinoma did not show differences in soluble IL2R concentrations when they were statified according to the differentiation of the tumor and the presence of absence of symptoms (p=NS) (Table XLIV).

TABLE XLIV
SOLUBLE IL2R CONCENTRATIONS IN SERA OF PATIENTS WITH ADENOCARCINOMA

| Histopathology | N* | Soluble IL2R (U/ml) |
|---|---|---|
| Moderately Differentiated Tumors | | |
| Asymptomatic | 7 | 771 ± 65 |
| Symptomatic | 5 | 751 ± 62 |
| Poorly Differentiated Tumors | | |
| Asymptomatic | 5 | 779 ± 72 |
| Symptomatic | 9 | 620 ± 45 |
| Total | 26 | 717 ± 57 |

*Number of patients in group
$p > 0.05$

Similarly, no difference was found when patients were classified according to the size of their tumor (p+NS).

24.3. Discussion

As described herein, we found elevated concentrations of soluble IL2R in serum samples of smokers and lung cancer patients as compared with those found in normal non-smoking controls. Even though there was overlap in the values between non-smokers and smokers, an influence of smoking could be seen in the level of soluble IL2R, since the concentrations of the molecule were higher in light smokers over non-smokers, and in moderate and heavy smokers over light smokers. As a group, smokers had higher levels of soluble IL2R ($p<0.001$).

Our results also showed that asymptomatic patients with relatively limited and moderately differentiated squamous cell carcinoma [as manifested by early stage (I-II), small tumors (<2 cm) and absence of symptoms] had higher levels of soluble IL2R than symptomatic patients, with big tumors (>4 cm) and advanced disease (stage IIIa-IIIb) ($p<0.05$).

An intriguing result is the different findings that emerged from patients with adenocarcinoma as compared with that of patients with squamous carcinoma. As a group, patients with adenocarcinoma were different from smokers and non-smokers ($p<0.001$), but they did not show any relationship between concentrations of soluble IL2R and stage of their disease, tumor size and presence or absence of symptoms. There was no difference in soluble IL2R levels between both groups of cancer as a whole ($p>0.05$).

Marked elevated concentrations of soluble IL2R have been reported in pulmonary sarcoidosis (Lawrence, E. C., et al., 1988, *Am. Rev. Resp. Dis.* 137:759-64), while only slightly elevated or normal concentrations were found in idiopathic pulmonary fibrosis (Lawrence, E. C., et al., 1987, *Sarcoidosis* 4:87-93) and asbestosis, respectively. This suggests that elevations of soluble IL2R in serum samples may not be a generalized response to inflammatory lung diseases.

It is possible that lymphocytes in the lower respiratory tract, both in the interstitium and epithelial lining fluid from smokers (and lung cancer) might be activated in situ. As peripheral blood lymphocytes, activated lymphocytes from both interstitium and broncheoalveolar spaces could be potential sources and origin of the increased serum levels of IL2R observed in smokers and lung cancer patients.

An alternative and additional cell source of soluble IL2R may be the expanded population of resident pulmonary macrophages seen in both smokers and lung cancer patients.

An interesting but unlikely hypothesis of the origin of soluble IL2R in lung cancer patients involves the tumor cells themselves. In theory, neoplastic transformation depresses certain cellular metabolic machinery (Shure, D. and Stool, E. W., 1980, Extrathoracic and endocrine manifestations of lung cancer, in *Manual of Clinical Problems in Pulmonary Medicine*, Bordow, R. A., et al., eds., Little Brown, Boston). Thus, with varying degrees of maturation arrest, tumor cells could potentially produce one or more peptides or proteins not normally produced by mature cells (Spriggs, D. R., 1988, *J. Clin. Invest.* 81:455-460; Froham, L. A., 1981, *Am. J. Med.* 70:995).

25. A CRITICAL ANALYSIS OF THE DIAGNOSTIC UTILITIES OF OF IMMUNOASSAYS FOR SERUM AND URINE SOLUBLE INTERLEUKIN-2 RECEPTOR LEVELS IN RENAL ALLOGRAFT RECIPIENTS

As described herein, a study was conducted to evaluate the diagnostic utility of assays for serum and urine soluble IL2R in renal allograft recipients. Serial serum and urine samples obtained prospectively were tested for soluble IL2R levels by sandwich enzyme immunoassay test, and correlations were sought with serum creatinine and episodes of rejection, cyclosporin A (CsA) toxicity, and infections. Our results demonstrated that a rise in serum IL2R between samples taken within a week predicted the onset of rejection better than absolute serum IL2R levels or urine values. For the diagnosis of acute rejection, a rise in serum IL2R (sensitivity 73%, specificity 87%) was comparable in overall test performance with a rise in serum creatinine (sensitivity 70%, specificity 84%). Overall, the two tests had equivalent receiver operating characteristic curves. Because the etiology of false positives in creatinine and IL2R assays differed (primarily cyclosporine toxicity and infection, respectively), the predictive value of the combined tests was superior to either alone.

25.1. Materials and Methods

25.1.1. Patients

The study population consisted of 33 adults who received renal allografts at the Massachusetts General Hospital. Maintenance immunosuppression consisted of cyclosporin A (CsA) and prednisone (Colvin, R. B., et al., 1987, *Clin. Immunol. Immunopathol.* 43:273-276). Episodes of rejection were treated with increased steroids, anti-T3 monoclonal antibody OKT3, or ATG (anti-thymocyte globulin) (Delmonico, F. L., et al., 1987, *Am. Surg.* 206:649-654). Rejection was diagnosed by a progressive rise in serum creatinine that responded to increased immunosuppression. Other causes of renal failure were excluded. Twenty-one episodes of rejection in 15 patients were monitored during the six month study period. Biopsies were obtained in ten patients and showed acute cellular rejection in all instances (Colvin, R. B., et al., 1987, *Clin. Immunol. Immunopathol.* 43:273-276). CsA toxicity was diagnosed by a rise in creatinine that responded to decreased CsA dose. Nine toxicity episodes occurred in eight patients. Three viral episodes occurred in three patients: a severe cytomegalovirus infection, lymphoproliferation associated with Epstein Barr virus, and a transient gastroenteritis accompanied by fever and lymphocytosis.

25.1.2. IL2R Assay

Serum (N=481) and urine (N=274) samples were obtained whenever possible prior to transplant and serially 1-2 times per week during hospitalization and at most clinic visits for the first 3-6 months after transplantation. Samples were coded and stored frozen until assay. Soluble immunoreactive IL2R levels were assayed by a sandwich enzyme immunoassay test kit according to the specifications of the manufacturer (CELLFREE ®, T Cell Sciences, Inc.) (Colvin, R. B., et al., 1987, *Clin. Immunol. Immunopathol* 43:273-276). Assays were performed in batches calibrated to units based on a standard supernatant from phytohemagglutinin activated lymphocytes.

25.1.3. Data Analysis

After decoding and classification of the clinical status, the results of the serum and urine IL2R assays and the serum creatinine assays were compared according to standard statistical techniques, using a spread sheet data base. Samples taken within the first four days after transplantation and during treatment for rejection and for two days afterward were excluded from analysis. Various measurements (absolute and change between serial samples) were compared for their clinical utility, as judged by sensitivity, specificity, predictive value, and Receiver Operating Characteristic (ROC) curves (Fink, D. J. and Galen, R. S., 1982, in *Computer Aids to Clinical Decisions*, Vol. 2, Williams, B. T., ed., CRC Press, Cleveland, Ohio, pp. 1–65).

25.2. Results

The aggregate data for serum and urine IL2R levels are summarized in Table XLV. The concentration of serum IL2R in 24 pretransplant patients was elevated compared with normal controls, but fell after transplantation in 20 of these patients. Pretreatment IL2R levels from patients who had no rejection episodes did not differ from those with subsequent rejection episodes. In 4 of the 5 patients with delayed onset of function (creatinine not falling below 4 by day 7), the serum IL2R levels remained elevated longer (transiently falling on days 1-2 in two patients). Paients with no episodes of rejection during the monitoring period had moderately elevated serum IL2R levels (980±692, 175 samples, 18 patients; P <0.001) compared with normals. Samples that were taken during stable periods from the patients that had an episode of rejection were similar and have been included in the "stable" category in Table XLV.

Serum IL2R usually rose during episodes of rejection and fell after successful antirejection immunosuppression was instituted. FIG. 25 illustrates a representative patient. Seven patients with rejection episodes were tested 1-2 days before the first rise in serum creatinine. Four patients had a rise in serum IL2R greater than the 90th percentile of stable patients. Overall, the mean serum IL2R was elevated 1-2 days prior to the rise in creatinine ($P<0.03$). Fourteen episodes of rejection in 9 patients were sampled on the first day of creatinine elevation; 9 of 14 samples (64%) were elevated above the 90th percentile of values during periods of stability. The IL2R levels remained elevated after the creatinine rise and into the treatment period, finally declining during or after antirejection therapy to the "stable" levels noted above. If only biopsy-confirmed rejection episodes are analyzed, the values are not significantly different (Table XLV). Serum IL2R also rose during episodes of infection (CMV, EBV, gastroenteritis) (Table XLV). In contrast, serum IL2R levels were not significantly raised in 8 patients with cyclosporine A toxicity.

The urine IL2R concentration rose in the immediate post-transplant period and remained higher in periods of stability than in pretransplant levels (Table XLV). During episodes of rejection, urine IL2R rose in a pattern that was not distinguishable from the serum values, except that somewhat greater sample-to-sample variation was noted. Urine IL2R also followed the pattern of serum IL2R during episodes of infection and cyclosporine A toxicity.

TABLE XLV

IL2R LEVELS IN RENAL ALLOGRAFT RECIPIENTS*

| Status | N** | Serum IL2R | p | N | Urine IL2R | p |
|---|---|---|---|---|---|---|
| Pre-Transplant | 24 (24) | 1541 ± 852 | | 8 (8) | 264 ± 235 | |
| Days 1-4 | 53 (31) | 1386 ± 874 | | 36 (24) | 636 ± 567 | |
| Stable | 258 (31) | 1218 ± 961 | | 117 (24) | 586 ± 427 | |
| Rejection | | | | | | |
| Before | | | | | | |
| creatinine rise (1-2 d) | 8 (7) | 2075 ± 1065 | <.03 | 5 (3) | 949 ± 698 | ns |
| biopsy | 4 (4) | 2629 ± 991 | | 3 (3) | 1241 ± 762 | |
| First day of | | | | | | |
| creatinine rise | 14 (9) | 2705 ± 1410 | <.001 | 9 (7) | 1188 ± 590 | <.01 |
| biopsy | 7 (6) | 2977 ± 1580 | | 6 (5) | 1436 ± 576 | |
| After | | | | | | |
| creatinine rise | 19 (10) | 2843 ± 1887 | <.001 | 11 (6) | 1511 ± 909 | <.01 |
| biopsy | 9 (6) | 3148 ± 2422 | | 11 (6) | 1454 ± 933 | |
| On treatment | 97 (15) | 2870 ± 1965 | <.001 | 66 (11) | 1645 ± 951 | <.001 |
| Infection | 15 (3) | 16098 ± 13587 | <.001 | 7 (2) | 3654 ± 1830 | <.01 |
| CsA toxicity | 14 (8) | 990 ± 594 | ns | 7 (6) | 512 ± 244 | ns |

*IL2R values are in units/ml (mean ± standard deviation); N, number of samples; number of patients in parentheses; p, comparison with stable patients, one-tailed t-test; ns, not significant (>.05). The data for the rejection episodes that were confirmed on biopsy are listed separately.
**Number of samples The absolute concentration of serum IL2R had a sensitivity of 46.3% and a specificity of 87.1% for the diagnosis of rejection, using the 90th percentile of stable patients as the threshold (Table XLVI). Even lower sensitivity occurred with a higher threshold (17% using the 95th percentile). Urine IL2R had comparable sensitivity and specificity (44.0% and 86.4%, respectively). A single serum creatinine level was no better, using the 90th percentile as a threshold for a positive test (sensitivity 39.0%, specificity 88.9%).

TABLE XLVI

COMPARISON OF ASSAYS FOR THE DIAGNOSIS OF RENAL ALLOGRAFT REJECTION*

| Assay | N** | Sensitivity (%) | Specificity (%) |
|---|---|---|---|
| Serum | | | |
| IL2R | 328 | 46.3 | 87.1 |
| Creatinine | 328 | 39.0 | 88.9 |
| Δ IL2R | 225 | 73.3 | 86.7 |
| Δ Creatinine | 225 | 70.3 | 84.0 |

TABLE XLVI-continued

COMPARISON OF ASSAYS FOR THE DIAGNOSIS
OF RENAL ALLOGRAFT REJECTION*

| Assay | N** | Sensitivity (%) | Specificity (%) |
|---|---|---|---|
| Urine | | | |
| IL2R | 156 | 44.0 | 86.4 |
| Δ IL2R | 111 | 52.4 | 87.8 |

*Positive defined as >90th percentile of values from stable patients. Samples taken during the first 4 days after transplantation were excluded from this analysis. Rejection samples were taken from 2 days before the first rise in creatinine until just before anti-rejection therapy was begun. N, number of samples. Δ, rise in serial values taken within 1 week.
**Number of samples In clinical practice, the absolute level of serum creatinine is less useful for the diagnosis of rejection than a rise in the level in serial samples. Based on this analogy, we determined whether the change in IL2R concentration in serial samples taken within a week (delta IL2R) might be more sensitive than the absolute level. The individual data on serum and urine IL2R and serum creatinine are given in a dot plot (FIG. 26), and are summarized in Table XLVI. The rise in serum IL2R had a much greater sensitivity (73.3%) than absolute serum IL2R levels for the diagnosis of rejection with no loss of specificity (86.7%). The delta urine IL2R measurement was not appreciably better than the absolute urine level and less sensitive (52.4%) than the delta serum IL2R (Table XLVI).

A rise in serum IL2R was comparable in sensitivity and specificity to a rise in serum creatinine using the 90th percentile of stable patients to define a positive test (Table XLVI). The two tests also had a comparable sensitivity specificity relationship overall, independent of the threshold selected for definition of a positive test, as shown in the ROC curves (FIG. 6). However, because the sources of false positives in creatinine and IL2R assays differ (primarily cyclosporine A toxicity and infection, respectively), the predictive value of the combined tests was superior to either test alone (Table XLVII).

TABLE XLVII

PREDICTIVE VALUE OF SERIAL
SERUM IL2R AND CREATININE ASSAYS

| Serum Values | | | % of Samples with Each Diagnosis | | | |
|---|---|---|---|---|---|---|
| Δ Cr >0.1 mg/dl | Δ IL2R >139 U/ml | N** | Stable | Rejection | CsA Toxicity | Infection |
| Single Test: | | | | | | |
| − | | 169 | 87.2 | 7.1 | 2.6 | 5.1 |
| + | | 56 | 33.9 | 44.6 | 14.3 | 5.4 |
| | − | 173 | 85.3 | 6.1 | 6.7 | 1.8 |
| | + | 52 | 30.8 | 51.9 | 1.9 | 15.4 |
| Combined Tests: | | | | | | |
| − | − | 143 | 92.3 | 3.5 | 2.8 | 1.4 |
| + | + | 26 | 7.7 | 80.8 | 3.8 | 7.7 |
| + | − | 30 | 56.7 | 16.7 | 23.3 | 3.3 |
| − | + | 26 | 53.8 | 23.1 | 0.0 | 23.1 |
| Overall | | 225 | 73.3 | 16.4 | 5.3 | 4.9 |

*Rise in values 5 days to 6 months after transplantation between serial samples taken within 1 week. Rejection samples were taken from 2 days before the rise in creatinine until the institution of anti-rejection therapy. Positive values were defined as >90th percentile of stable values.
**N, Number of samples

25.3. Discussion

The development of a reliable, noninvasive, economical diagnostic test for immunologic rejection is an important goal. The renal biopsy is the reference standard, but is not without risk and expense. Fine needle aspirates have a lower risk, but have not been widely applied because they require specialized expertise for performance and interpretation. Many less invasive blood tests have been proposed, only to be abandoned due to a high cost/benefit ratio or lack of clinical predictive value beyond that of serum creatinine.

We have found that the specificity and sensitivity of soluble serum IL2R assays are similar to those of serum creatinine for the diagnosis of rejection. Among the various IL2R measurements, the serial change in serum IL2R was the most sensitive and specific. The absolute level of serum IL2R varied more from patient to patient and was elevated in chronic renal failure (Colvin, R. B., et al., 1987, Clin. Immunol. Immunopathol. 43:273-276). The urinary concentration of IL2R showed a similar pattern, but had greater sample to sample variation, probably due in part to differences in urine output and urinary degradation of the immunoreactive determinants. Standardization with urine creatinine concentration and inhibition of protease activity can be used to improve the quality of the urinary assays.

A revealing analysis of a diagnostic test is its ROC curve, which formalizes the relationship between sensitivity and specificity, and is an intrinsic property of the test, independent of disease prevalence or the definition of a positive result (Fink, D. J. and Galen, R. S., 1982, in *Computer Aids to Clinical Decisions*, Vol. 2, Williams, B. T., ed., CRC Press, Cleveland, Ohio, pp. 1-65). ROC curves reported in these studies demonstrate that the overall test performance of serum IL2R was indistinguishable from serum creatinine for the diagnosis of rejection. However, each test had different sources of "false positives" in the allograft recipients. CsA toxicity raised the creatinine levels more than the soluble IL2R levels, and viral infection was associated primarily with a marked rise in soluble IL2R. Thus, the combination of tests for serum IL2R and creatinine had greater predictive value than either test alone for distinguishing acute rejection from infection or CsA toxicity. The strength of the combination test is evident in Table XLVII. If a rise in serum IL2R accompanies a rise in creatinine, the odds are 20:1 in favor of rejection over CsA toxicity. In contrast, if no IL2R rise accompanies the rise in creatinine, the odds favor CsA over rejection by about 3:2 (the majority of patients will be stable).

In these studies and others (Colvin, R. B., et al., 1987, Clin. Immunol. Immunopathol. 43:273-276; Solc, V. and Krause, J. R., 1987, Diag. Clin. Immunol. 5:171-174), infection was accompanied by levels of serum IL2R (up to 33,825 units/ml during a cytomegalovirus infection in this series) even higher than those observed during allograft rejection, suggesting a quantitative or qualitative difference in T cell activation. Accordingly, extremely high levels of IL2R favor the diagnosis of infection over rejection. Finally, transient elevations in serum IL2R are sometimes observed in clinically stable transplant recipients. These have been categorized here as "false positives" but may be caused by subclinical episodes of rejection or infection.

IL2R assays can also be valuable in the monitoring of immunologic activity in recipients of other organ allografts, such as the heart, liver and pancreas, in which the early diagnosis of rejection is particularly difficult.

26. EVALUATION OF THE ROLE OF THE SOLUBLE CD8 RECEPTOR AND IL-2 RECEPTOR IN PATIENTS WITH HUMAN IMMUNODEFICIENCY VIRUS INFECTION

We evaluated the levels of soluble CD8 and IL2R in patients with HIV infection. The levels of CD8 and IL2R were compared with each other and with levels of plasma p24 antigen, CD4+ cells, CD8+ cells, and CD4/CD8 ratios.

26.1. Methods

26.1.1. Sample Selection

Stored serum from patients with HIV infection was examined using either the CELLFREE® IL-2R Test Kit or CELLFREE® T8 Test Kit (T Cell Sciences, Cambridge, Mass.). 63 patients with HIV infection and 7 normal controls were studied. Patients were divided into 4 groups depending upon the manifestations of HIV infection; these groups were: 21 assymptomatic seropositive (ASSYM), 19 AIDS related complex (ARC), 13 Kaposi's sarcoma (KS) and 10 AIDS with opportunistic infection. Stored sera from 15 patients followed longitudinally over a period of 2 years were also examined.

26.1.2. HIV p24 Antigen Assay

This assay utilized a sandwich ELISA microplate format. Highly specific rabbit polyclonal antibodies to HIV p24 core antigen were immobilized on microtiter plate wells and used to capture HIV p24 core antigen present in 450 μl of plasma. The captured HIV p24 core antigen was complexed with biotinylated polyclonal antibodies to HIV p24 core antigen and probed with a streptavidin-horseradish peroxidase conjugate. This complex was visualized by incubation with orthophenyldiamine-HCl producing a color intensity directly proportional to the amount of HIV p24 core antigen captured. The results were also quantitated spectrophotometrically and compared against the absorbance of an HIV p24 core antigen standard curve.

26.1.3. CD4/CD8 Ratio

The CD4 and CD8 ratios were determined by standard flow cytometry.

26.2. Results

Soluble CD8, soluble IL2R, p24 antigen, CD4/CD8 ratio, CE4$^{30}$ cells and CD8+ cells were measured in samples from patients with AIDS, ARC, KS, ASSYM or normals, as shown in Table XLVIII.

TABLE XLVIII

| Patient Group | Measurement of Shed Receptors in Patients with Different Manifestations of AIDS* | | | | |
|---|---|---|---|---|---|
| | Soluble CD8 | Soluble IL2R | p24 | CD4/CD8 | % CD4 | % CD8 |
| ASSYM | 1029 ± 89 | 783 ± 98 | 16.4 ± 9.0 | 0.73 ± 0.08 | 27.9 ± 2.9 | 50.2 ± 3.1 |
| KS | 1165 ± 131 | 970 ± 129 | 8.9 ± 2.3 | 0.59 ± 0.12 | 14.7 ± 1.6 | 50.0 ± 6.4 |
| ARC | 980 ± 118 | 1011 ± 119 | 9.7 ± 3.5 | 0.71 ± 0.11 | 28.3 ± 3.6 | 47.6 ± 2.9 |
| AIDS | 717 ± 115 | 1566 ± 157 | 19.7 ± 8.1 | 0.19 ± 0.05 | 9.9 ± 2.3 | 50.2 ± 3.4 |
| Normals | 508 ± 40 | 188 ± 28 | | | | |

*Expressed as mean ± standard mean; soluble CD8 and soluble IL2R expressed as units/ml; p24 expressed as pg/ml Using chi-square analysis, comparing each group with normal controls, the majority of patients with AIDS, ARC, ASSYM and KS showed levels of both IL2R and soluble CD8 which were greater than the upper 95% value of normal ($p < 0.00001$). IL2R was better than CD4/CD8, %CD4, and p24 for discriminating ASSYM from AIDS ($p < 0.0001$), ASSYM from ARC ($p < 0.002$) and ARC from AIDS ($p < 0.0001$). Of interest is the observed difference in soluble CD8 between groups with ASSYM, KS and AIDS. This suggests that early on in the course of HIV infection, elevated soluble CD8 levels may reflect host immune response to HIV. It has been demonstrated that CD8 positive cells are able to control HIV infection in vitro by suppressing viral replication (Walker, C. M. et al., 1986, *Science*, 234, 1563–1566). Soluble CD8 levels may be an accurate measure of the immune system's attempts to suppress HIV infection. In addition, by using a combination of both soluble IL2R and soluble CD8 levels in each patient group, it was possible to distinguish between normal and assymptomatic patients.

In addition to determining the value of each soluble marker level, a comparison was also made between different soluble marker values to determine how they correlated with one another. The data presented in Table XLIX presents the correlation observed between several marker combinations. The samples analyzed for this table do not represent longitudinal samples obtained from individual patients, but samples from the population of people belonging to the different HIV-infected groups.

TABLE XLIX

CORRELATIONS BETWEEN THE BEHAVIOR OF DIFFERENT PARAMETERS IN AIDS PATIENTS*

| Correlation | ASSYM | ARC | KS | AIDS | Combined HIV Positive |
|---|---|---|---|---|---|
| sCD8 v sIL-2R | | | + | | + |
| sCD8 v CD4/CD8 | | − | | − | +− |
| sCD8 v % CD4 | | − | | | |
| sCD8 v % CD8 | + | | | | + |
| p24 v s IL2R | | + | | | + |
| sIL2R v CD4/CD8 | | | | − | − |
| sIL2R v % CD4 | | − | | | − |
| sIL2R v % CD8 | | + | | | |
| CD4/CD8 v % CD4 | + | + | + | | + |
| CD4/CD8 v % CD8 | − | | − | − | − |
| % CD4 v % CD8 | − | − | | | − |

*Pearson Correlation is expressed as + (positive correlation between the two parameters) or − (negative correlation between the two parameters); blank values indicate that the correlation had a probability index > 0.05; s = soluble It is clear that the occurrence of soluble markers is not independent of one another or of other markers of the immune system. Thus, the combined behavior of these receptors should be even more valuable than the observance of any single receptor.

In addition to the patient samples analyzed above, three patients with ARC and three with KS were followed longitudinally as shown in FIG. 27. The results of this study indicated that soluble CD8 levels appeared to parallel the change in p24 core antigen levels. Since the p24 core antigen levels have not proved to be sensitive enough tests of the progression of AIDS, we propose that the soluble CD8 levels, which reflect the status of the immune system itself, can be a much better indicator.

27. DEPOSIT OF HYBRIDOMAS

The following hybridoma cell lines, producing the indicated monoclonal antibody, have been deposited with the American Type Culture Collection, Rockville, Md., and have been assigned the listed accession numbers:

| Hybridoma | Monoclonal Antibody | Accession Number |
|---|---|---|
| Cell line AM92/2R12 | AM92/2R12 (anti-IL2R) | HB 9341 |
| Cell line 7G7 | 7G7 (anti-IL2R) | HB 10242 |
| Cell line 4C9 | 4C9 (anti-CD8) | HB 10242 |
| Cell line 5F4/7B12 | 5F4/7B12 (anti-CD8) | HB 9342 |
| Cell line 8F4 | 8F4 (anti-CD4) | HB 9843 |
| Cell line R2B7 | R2B7 (anti-CD4) | HB 9842 |

The present invention is not to be limited in scope by the cell lines deposited since the deposited embodiments are intended as single illustrations of one aspect of the invention and any cell lines which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

What is claimed:

1. A method for detecting or measuring the amount in a sample of a soluble molecule carrying antigenic determinants of the CD4 T cell surface antigen comprising:
   (a) contacting the sample with a first anti-CD4 monoclonal antibody and with a second anti-CD4 monoclonal antibody that does not compete for the same binding site on the CD4 antigen as the first anti-CD4 antibody under conditions which allow immunospecific binding; and
   (b) detecting whether immunospecific binding occurs of a component in the sample with both first and second anti-CD4 antibodies, in which immunospecific binding of a component of the sample with both first and second anti-CD4 antibodies indicates the presence of the soluble molecule,
in which the sample contains only such soluble molecules as are spontaneously released.

2. The method according to claim 1 in which the second antibody is labeled so that it is capable of producing a detectable signal.

3. The method according to claim 1 in which the first antibody is immobilized.

4. The method according to claim 1 in which the first antibody is immobilized and the second antibody is labeled so that immunospecific binding is indicated by the detection of immobilized label.

5. The method according to claim 1, 2 or 4 in which the first antibody comprises monoclonal antibody 8F4 as produced by the hybridoma deposited with the ATCC and assigned accession number HB 9843.

6. The method according to claim 1, 2 or 4 in which the second antibody comprises monoclonal antibody R2B7 as produced by the hybridoma deposited with the ATCC and assigned accession number HB 9842.

7. The method according to claim 1, 2 or 4 in which the first antibody comprises monoclonal antibody 8F4 as produced by the hybridoma deposited with the ATCC and assigned accession number HB 9843, and the second antibody comprises monoclonal antibody R2B7 as produced by the hybridoma deposited with the ATCC and assigned accession number HB 9842.

8. The method according to claim 1 in which the first antibody has the same epitope specificity as that of monoclonal antibody 8F4 as produced by the hybridoma deposited with the ATCC and assigned accession number HB 9843.

9. The method according to claim 1 in which the second antibody has the same epitope specificity as that of monoclonal antibody R2B7 as produced by the hybridoma deposited with the ATCC and assigned accession number HB 9842.

10. The method according to claim 1 in which the first antibody has the same epitope specificity as that of monoclonal antibody 8F4 as produced by the hybridoma deposited with the ATCC and assigned accession number HB 9843, and the second antibody has the same epitope specificity as that of monoclonal antibody R2B7 as produced by the hybridoma deposited with the ATCC and assigned accession number HB 9842.

11. The method according to claim 1 or 4 in which the sample is serum.

12. A kit for measuring the level of a cell free soluble molecule carrying antigenic determinants of the CD4 T cell surface antigen comprising in one or more vials:
   (a) a first anti-CD4 monoclonal antibody; and
   (b) a second anti-CD4 monoclonal antibody that does not compete for the same binding site on the CD4 antigen as the first anti-CD4 antibody,
in which both the first and second monoclonal antibodies bind to a spontaneously released, soluble molecule carrying antigenic determinants of the CD4 T cell surface antigen.

13. The kit of claim 12 in which the second anti-CD4 antibody is labeled so that it is capable of producing a detectable signal.

14. The kit of claim 13 in which the label is an enzyme.

15. The kit of claim 14 in which the enzyme is horseradish peroxidase.

16. The kit of claim 12 in which the first antibody comprises monoclonal antibody 8F4 as produced by the hybridoma deposited with the ATCC and assigned accession number HB 9843.

17. The kit of claim 12 in which the second antibody comprises monoclonal antibody R2B7 as produced by the hybridoma deposited with the ATCC and assigned accession number HB 9842.

18. The kit of claim 12 in which the first antibody comprises monoclonal antibody 8F4 as produced by the hybridoma deposited with the ATCC and assigned accession number HB 9843, and the second antibody comprises monoclonal antibody R2B7 as produced by the hybridoma deposited with the ATCC and assigned accession number HB 9842.

19. The kit of claim 17 in which monoclonal antibody R2B7 is labeled.

20. The kit of claim 18 in which monoclonal antibody R2B7 is labeled.

21. The kit of claim 20 in which the label is an enzyme.

22. The kit of claim 21 in which the enzyme is horseradish peroxidase.

23. The kit of claim 12 in which the first antibody has the same epitope specificity as that of monoclonal antibody 8F4 as produced by the hybridoma deposited with the ATCC and assigned accession number HB 9843.

24. The kit of claim 12 in which the second antibody has the same epitope specificity as that of monoclonal antibody R2B7 as produced by the hybridoma deposited with the ATCC and assigned accession number HB 9842.

25. The kit of claim 12 in which the first antibody has the same epitope specificity as that of monoclonal antibody 8F4 as produced by the hybridoma deposited with the ATCC and assigned accession number HB 9843, and the second antibody has the same epitope specificity as that of monoclonal antibody R2B7 as produced by he hybridoma deposited with the ATCC and assigned accession number HB 9842.

26. A method for diagnosing a state of immune activation in a subject comprising detecting or measuring an increase, relative to a baseline level, in the amount in a sample from the subject of a spontaneously released, soluble molecule carrying antigenic determinants of the CD4 T cell surface antigen.

27. A method for diagnosing a state of immune activation in a subject comprising detecting or measuring an increase, relative to a baseline level, in the amount in a sample from the subject of soluble molecule carrying antigenic determinants of the CD4 T cell surface antigen, according to the method of claim 1.

28. A method for diagnosing a state of immune activation in a subject comprising detecting or measuring an increase, relative to a baseline level, in the amount in a sample from the subject of soluble molecule carrying antigenic determinants of the CD4 T cell surface antigen, according to the method of claim 7.

29. A method for determining the phenotype of a T cell comprising first incubating the cell in a cell culture fluid, and subsequently detecting or measuring the amount, in a sample of the cell culture fluid, of a spontaneously released, soluble molecule carrying antigenic determinants of the CD4 T cell surface antigen, the presence of said spontaneously released, soluble molecule being indicative of the phenotype of the cell.

30. A method for staging adult T cell leukemia in a patient comprising measuring the amount of a spontaneously released, soluble molecule carrying antigenic determinants of the CD4 T cell surface antigen in a sample obtained from the patient, in which increases in amounts relative to healthy individuals or to the patient at an earlier time indicates more advanced stages of disease.

31. The method according to claim 30 in which the sample is serum.

32. A method for diagnosing rheumatoid arthritis in a patient comprising detecting or measuring an increase in the amount, relative to healthy individuals or to the patient at an earlier time, of a spontaneously released, soluble molecule carrying antigenic determinants of the CD4 T cell surface antigen in synovial fluid obtained from the patient.

33. A method for diagnosing rheumatoid arthritis in a patient comprising detecting an increase in the amount in synovial fluid of the patient relative to the amount in serum of the patient of a spontaneously released, soluble molecule carrying antigenic determinants of the CD4 T cell surface antigen.

34. A method for monitoring the treatment of a patient with a viral infection comprising measuring the level in a body fluid of the patient after treatment of a spontaneously released, soluble molecule carrying antigenic determinants of the CD4 T cell surface antigen.

35. The method according to claim 34 in which the viral infection is Human Immunodeficiency Virus infection.

36. A kit for detecting, monitoring the treatment of, or staging a disease or disorder in a patient comprising in one or more vials:
   (a) a pair of anti-interleukin-2 receptor monoclonal antibodies, which antibodies doe not compete for the same binding site on the interleukin-2 receptor; and
   (b) a pair of anti-CD4 monoclonal antibodies, which anti-CD4 monoclonal antibodies do not compete for the same binding site on the CD4 antigen,
in which both anti-CD4 monoclonal antibodies bind to a spontaneously released, soluble molecule carrying antigenic determinants of the CD4 T cell surface antigen.

37. A composition suitable for use in the detection or measurement of a spontaneously released soluble molecule carrying antigenic determinants of the CD4 T cell surface antigen comprising:
   (a) a first anti-CD4 monoclonal antibody; and
   (b) a second anti-CD4 monoclonal antibody that does not compete for the same binding site on the CD4 antigen as the first anti-CD4 antibody,
in which both the first and second monoclonal antibodies bind to a spontaneously released, soluble molecule carrying antigenic determinants of the CD4 T cell surface antigen.

* * * * *